(12) United States Patent
Tazume

(10) Patent No.: US 12,136,059 B2
(45) Date of Patent: Nov. 5, 2024

(54) DISTRIBUTION SYSTEM, INFORMATION PROCESSING DEVICE, AND METHOD

(71) Applicant: Rakuten Group, Inc., Tokyo (JP)

(72) Inventor: Toshiaki Tazume, Tokyo (JP)

(73) Assignee: Rakuten Group, Inc., Tokyo (JP)

(*) Notice: Subject to any disclaimer, the term of this patent is extended or adjusted under 35 U.S.C. 154(b) by 701 days.

(21) Appl. No.: 17/362,219

(22) Filed: Jun. 29, 2021

(65) Prior Publication Data

US 2022/0101251 A1    Mar. 31, 2022

(30) Foreign Application Priority Data

Sep. 30, 2020  (JP) .................................. 2020-164654

(51) Int. Cl.
*G06Q 10/0832* (2023.01)
*A47B 81/00* (2006.01)
*A61L 2/00* (2006.01)
*B65B 55/00* (2006.01)
*B65G 1/04* (2006.01)
*G06Q 10/083* (2024.01)

(52) U.S. Cl.
CPC ......... *G06Q 10/0832* (2013.01); *A47B 81/00* (2013.01); *A61L 2/00* (2013.01); *B65B 55/00* (2013.01); *B65G 1/04* (2013.01); *G06Q 10/0838* (2013.01)

(58) Field of Classification Search
CPC ............ G06Q 10/0832; G06Q 10/0838; A47B 81/00; B65G 1/04; A61L 2/00; B65B 55/00
See application file for complete search history.

(56) References Cited

U.S. PATENT DOCUMENTS

2014/0370167 A1*  12/2014  Garden ............ G06Q 10/08355
                                                              99/325

FOREIGN PATENT DOCUMENTS

CN    111994415 B  *  3/2022  ............... A61L 2/18
JP    2018-151923 A     9/2018
JP    2019191755 A  *  10/2019

* cited by examiner

*Primary Examiner* — Jacob S. Scott
*Assistant Examiner* — Erin Morris
(74) *Attorney, Agent, or Firm* — Sughrue Mion, PLLC

(57) ABSTRACT

A distribution system, an information processing device, and a method that can manage a last time at which a human touched an article prior to the article being received, or can manage an amount of elapsed time from that last time. The distribution system 1 includes a first distribution mechanism 10 that includes a first transporter 11 that transports an article to a destination of the article. The distribution system 1 also includes a manager that manages a first time that is a time earlier than a receiving time at which the article transported by the first transporter 11 is received and that is a last time at which a human contacted the article, or manages a first amount of elapsed time that is an amount of elapsed time from the first time.

18 Claims, 37 Drawing Sheets

FIG. 14

PROCEDURE TABLE

| | PROCEDURE ID | PROCEDURE NAME | INVOLVEMENT FLAG |
|---|---|---|---|
| 1 | P1 | UNDERTAKING PROCEDURE | TRUE |
| 2 | P2 | TRANSPORT TO DEPOSITORY PROCEDURE | FALSE |
| 3 | P3 | STORE IN DEPOSITORY PROCEDURE | FALSE |
| 4 | P4 | RETRIEVAL PROCEDURE | FALSE |
| 5 | P5 | TRANSPORT TO FIRST TRANSPORTER PROCEDURE | FALSE |
| 6 | P6 | HAND OVER PROCEDURE | FALSE |
| 7 | P7 | TRANSPORT TO LOCKER DEVICE PROCEDURE | FALSE |
| 8 | P8 | STORE IN LOCKER DEVICE PROCEDURE | FALSE |
| 9 | P9 | NOTIFICATION PROCEDURE | FALSE |

FIG. 15

SECOND TIME TABLE

| ARTICLE ID | | SECOND TIME |
|---|---|---|
| PRODUCT NUMBER | INDIVIDUAL IDENTIFICATION NUMBER | |
| G01 | S01 | 00:00 |
| G01 | S02 | 00:00 |
| ... | ... | ... |
| G02 | S01 | 12:00 |
| ... | ... | ... |

FIG. 16

DEPOSITORY TABLE

| BOX ID | ARTICLE ID | |
| --- | --- | --- |
| | PRODUCT NUMBER | INDIVIDUAL IDENTIFICATION NUMBER |
| B01 | G01 | S01 |
| B02 | G02 | S02 |
| ... | ... | ... |

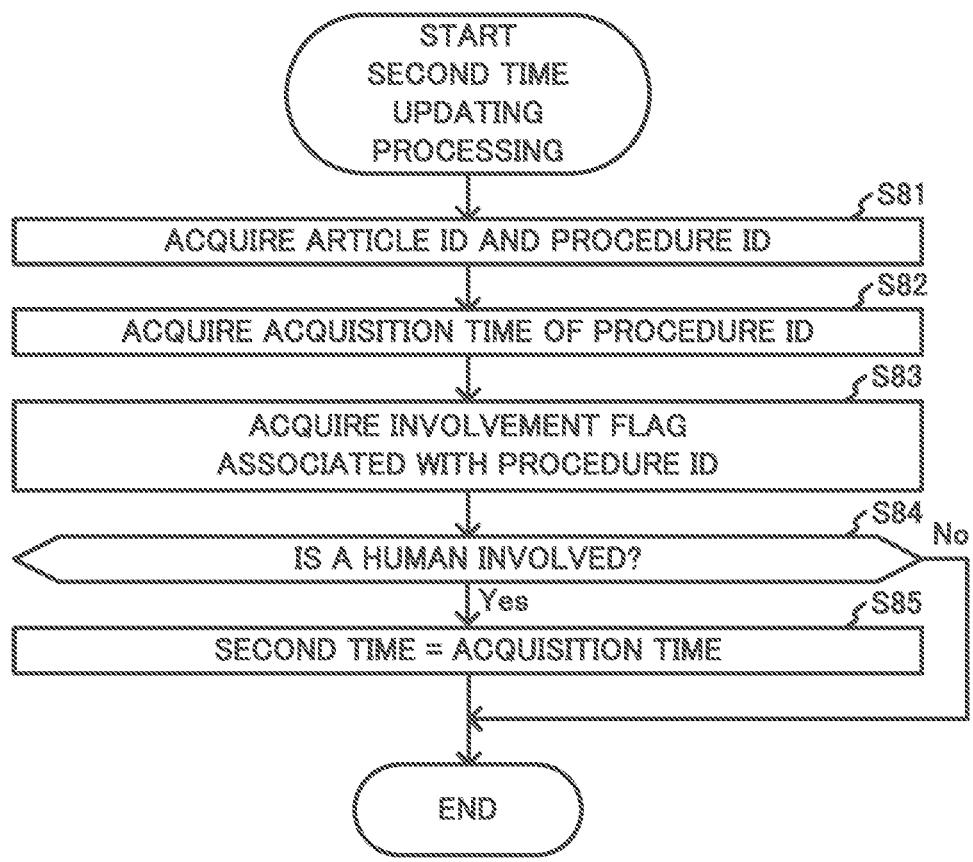

FIG. 20

ARTICLE TABLE

| ARTICLE ID | | DESTINATION | FIRST TIME | BOX ID | PASSWORD |
|---|---|---|---|---|---|
| PRODUCT NUMBER | INDIVIDUAL IDENTIFICATION NUMBER | | | | |
| G01 | S01 | ...SETAGATA-KU, TOKYO-TO | 12:00 AM | S1 | **** |
| G02 | S02 | ...CHIYODA-KU, TOKYO-TO | 08:00 AM | S2 | **** |
| ... | ... | ... | ... | ... | ... |

FIG. 31
PRODUCT NUMBER TABLE

| PRODUCT NUMBER | TYPE ID |
|---|---|
| G01 | T01 |
| G02 | T01 |
| ... | ... |
| G11 | T02 |
| ... | ... |

FIG. 32

TYPE TABLE

| TYPE ID | COEFFICIENT |
|---------|-------------|
| T01     | 1.2         |
| T02     | 0.9         |
| ...     | ...         |

FIG. 34

ENVIRONMENT TABLE

| RANGE | COEFFICIENT |
|---|---|
| ... | ... |
| 30° C to 39° C | 1.8 |
| 20° C to 29° C | 1.1 |
| 10° C to 19° C | 0.9 |
| ... | ... |

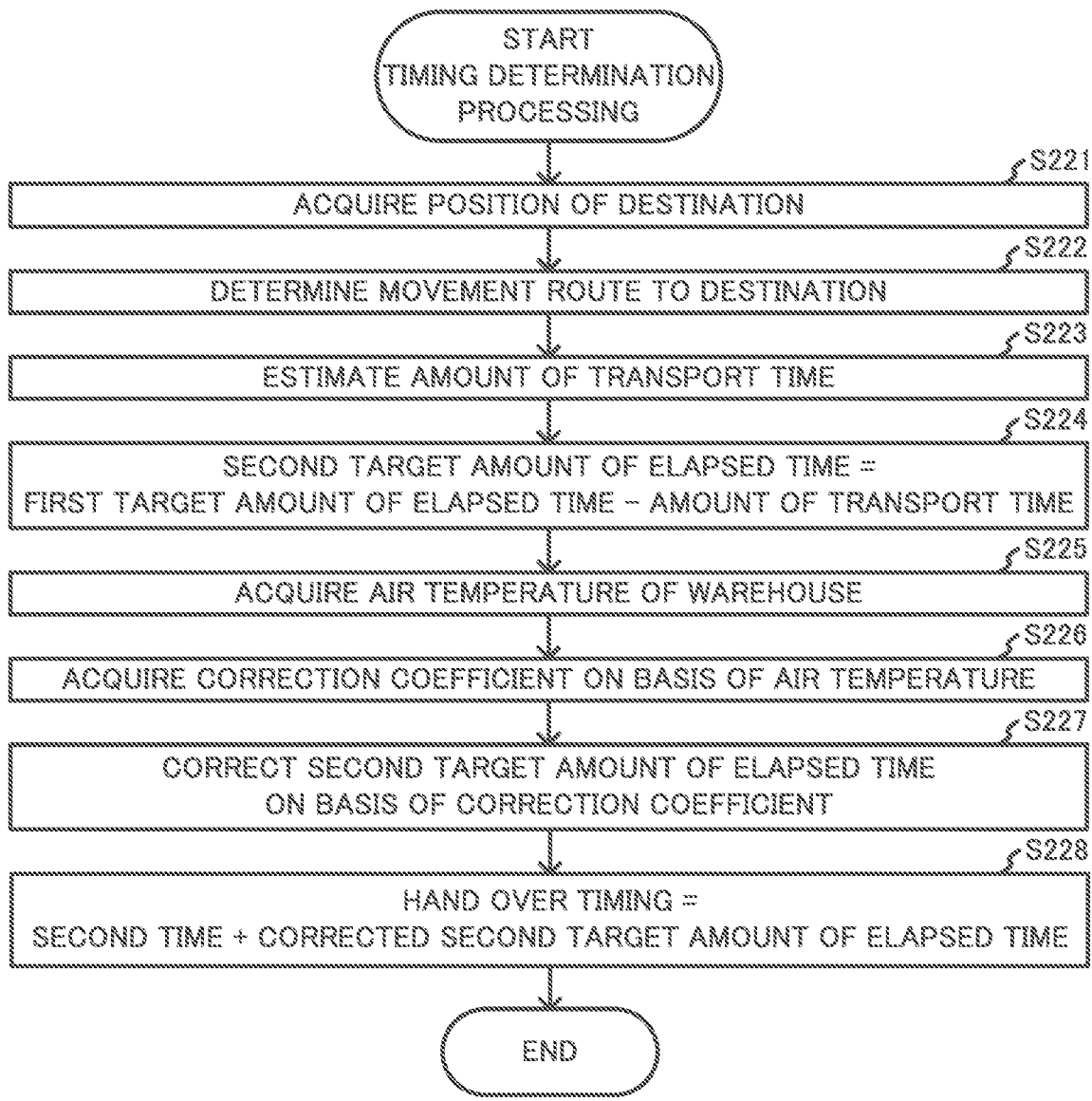

DISTRIBUTION SYSTEM, INFORMATION PROCESSING DEVICE, AND METHOD

TECHNICAL FIELD

The present disclosure relates to a distribution system, an information processing device, and a method.

BACKGROUND ART

In the related art, systems in which a robot is caused to deliver an article, and that are provided with a database for managing the inventory of articles are known (for example, Patent Literature 1).

CITATION LIST

Patent Literature

Patent Literature 1: Unexamined Japanese Patent Application Publication No. 2018-151923

SUMMARY OF INVENTION

Technical Problem

In the system described in Patent Literature 1, when a worker hands over an article to the robot, viruses or bacteria possessed by the worker may adhere to the article. The magnitude of infectivity of the viruses or bacteria adhered to the article decreases with the passage of time. As such, in order to prevent the recipient of the article from becoming infected with the viruses or bacteria, the last time at which the article is touched by a person including the worker prior to the article being received, or the amount of elapsed time from that last time must be managed. However, there is a problem in that the system of Patent Literature 1 can only manage the inventory of the article, and cannot manage the last time at which a human touched the article or the amount of elapsed time from that last time.

The present disclosure is made with the view of the above situation, and an objective of the present disclosure is to provide a distribution system, an information processing device, and a method that can manage a last time at which a human touched an article prior to the article being received, or an amount of elapsed time from that last time.

Solution to Problem

A distribution system according to a first aspect of the present disclosure that achieves the objective described above is characterized by including:
a first distribution mechanism that includes a transporter that transports an article to a destination of the article; and
a manager that manages a first time that is a time earlier than a receiving time at which the article transported by the transporter is received and that is a last time at which a human contacted the article, or manages a first amount of elapsed time that is an amount of elapsed time from the first time.

Advantageous Effects of Invention

According to the distribution system, the information processing device, and the method according to the present disclosure, it is possible to manage a last time at which a human touched an article before the article is received, or the amount of elapsed time from the last time.

BRIEF DESCRIPTION OF DRAWINGS

FIG. 14 is a drawing illustrating an example of a procedure table stored in the information processing device;

FIG. 15 is a drawing illustrating an example of a second time table stored in the information processing device;

FIG. 16 is a drawing illustrating an example of a depository table stored in the information processing device;

FIG. 18 is a flowchart illustrating an example of second time updating processing executed by the information processing device;

FIG. 20 is a drawing illustrating an example of an article table stored in the information processing device;

FIG. 31 is a drawing illustrating an example of a product number table stored in the information processing device;

FIG. 32 is a drawing illustrating an example of a type table stored in the information processing device;

FIG. 34 is a drawing illustrating an example of an environment table stored in the information processing device; and FIG. 35 is a flowchart illustrating an example of timing determination processing executed by the information processing device according to Modified Example 6 of Embodiment 2.

DESCRIPTION OF EMBODIMENTS

Embodiment 1

Hereinafter, Embodiment 1 of the present disclosure is described while referencing the drawings.

A distribution system 1 according to Embodiment 1 of the present disclosure transports a sold article to a destination specified by a buyer. As such, the distribution system 1 is also referred to as a "transport system."

Figure 1:
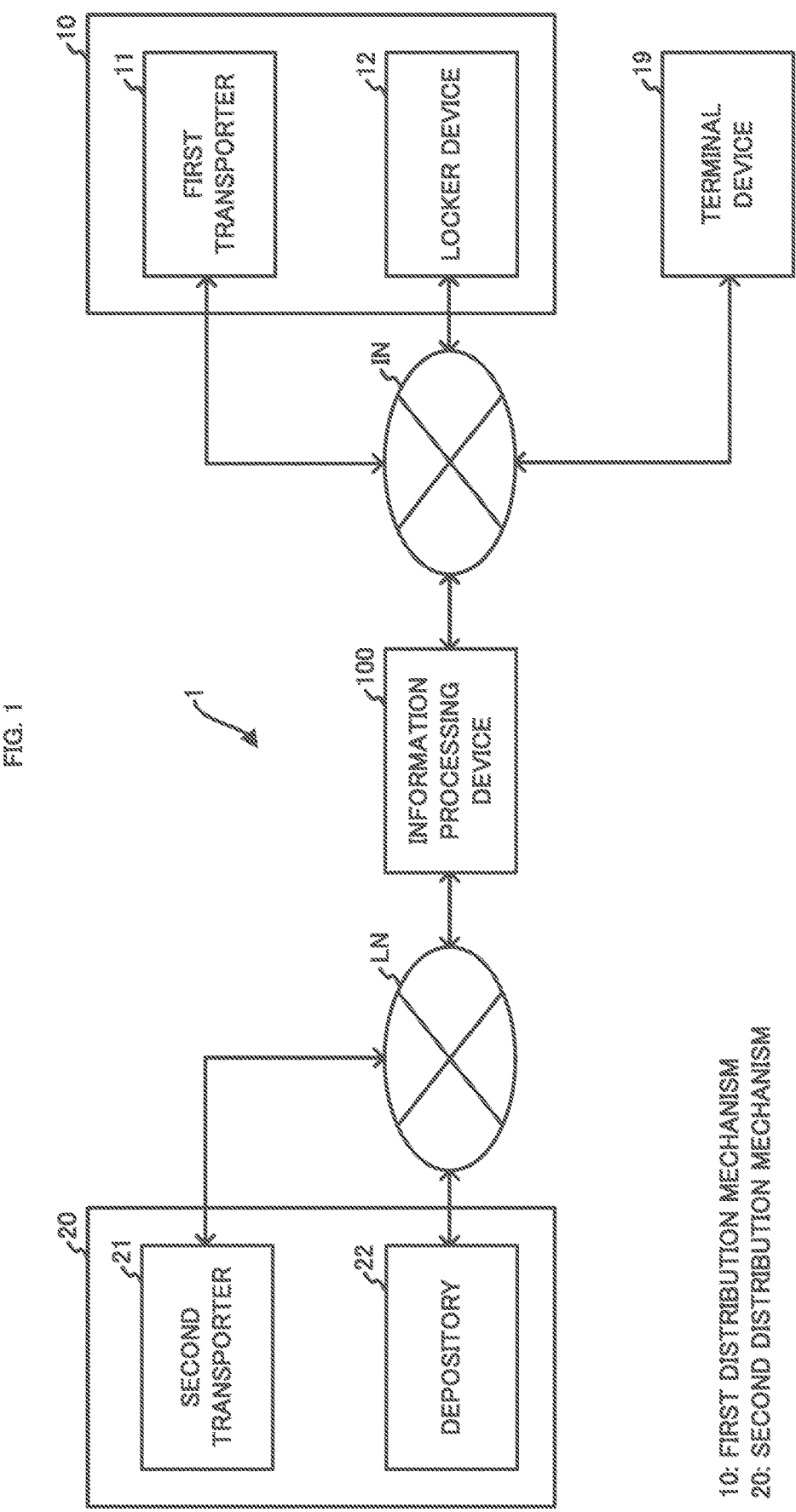
FIG. 1 is a system configuration drawing illustrating a configuration example of a distribution system according to Embodiment 1 of the present disclosure.

The distribution system 1 includes a first distribution mechanism 10 and a terminal device 19 carried by the buyer. The first transporter 11 includes a first transporter 11 such as illustrated in FIG. 1 that transports the sold article and a locker device 12 that is installed at the destination and that stores the transported article. In the present embodiment, to facilitate comprehension, a description is given in which the buyer and the recipient are the same person. However, the present embodiment is not limited thereto, and the buyer and the recipient may be different people.

The distribution system 1 further includes a second distribution mechanism 20. The second distribution mechanism 20 includes a second transporter 21 that undertakes the article from a carrier that transported the article from a factory, for example, and transports the undertaken article, and a depository 22 that stores the article transported by the second transporter 21. When the article is sold, the second transporter 21 of the second distribution mechanism 20 transports the sold article from the depository 22 to the first transporter 11 of the first distribution mechanism 10, and hands over the transported article to the first transporter 11.

Furthermore, the distribution system 1 includes an information processing device 100 that performs control for causing the first transporter 11 of the first distribution mechanism 10 and the second transporter 21 of the second distribution mechanism 20 to transport the sold article from the depository 22 to the destination. With the distribution system 1, the following nine procedures related to the delivery of the sold article are executed using the configuration described above.

The first procedure is an undertaking procedure in which the second transporter 21 undertakes an article from the carrier. The second procedure is a procedure in which the second transporter 21 transports the undertaken article to the depository 22 (hereinafter referred to as "transport to depository procedure"). The third procedure is a procedure in which the second transporter 21 stores the transported article in the depository 22 (hereinafter referred to as "store in depository procedure"). The first to the third procedures are performed on an unsold article and, as such, are referred to as "pre-sale procedures."

The fourth procedure is a retrieval procedure in which the second transporter 21 retrieves the sold article from the depository 22. The fifth procedure is a procedure in which the second transporter 21 transports the retrieved article to the first transporter 11 (hereinafter referred to as "transport to first transporter procedure"). The sixth procedure is a hand over procedure in which the second transporter 21 hands over the transported article to the first transporter 11. The seventh procedure is a procedure in which the first transporter 11 transports the handed over article to the locker device 12 installed at the destination of the article (hereinafter referred to as "transport to locker device procedure"). The eighth procedure is a procedure in which the first transporter 11 stores the transported article in the locker device 12 (hereinafter referred to as "store in locker device procedure"). The ninth procedure is a procedure in which the information processing device 100 sends, to the terminal device 19 carried by the recipient, a notification informing that the article has been delivered to the locker device 12 at the destination (hereinafter referred to as "notification procedure"). The fourth to the ninth procedures are performed on a sold article and are performed after the pre-sale procedures and, as such, are referred to as "post-sale procedures."

The information processing device 100 manages a time that is a time prior to a receiving time at which the delivered article is received by the recipient and is a last time at which a human contacted the article (hereinafter referred to as "first time"). The magnitude of the infectivity of viruses and bacteria expelled from humans and adhered to the article decreases with the passage of time. Accordingly, the information processing device 100 manages the first time so as to notify, on the basis of the first time, a recommended receiving start time at which receiving of the article is recommended to start.

In the present embodiment, a description is given in which times are expressed in terms of days, hours, and minutes, but the present embodiment is not limited thereto. The times may be expressed in terms of days, hours, minutes, and seconds, may be expressed in terms of days and hours, or may be expressed in terms of days. Additionally, the times may be expressed in terms of hours, minutes, and seconds, may be expressed in terms of hours and minutes, or may be expressed in terms of hours.

In the present embodiment, the phrase "a human contacts the article" means that a human physically touches the article. The phrase "a human physically touches the article" is not limited to the body of a human physically touching the article but, for example, also includes clothing worn by a human, such as a glove or a uniform, physically touching the article.

The information processing device 100 further manages a time that is a time prior to a hand over time at which the article is handed over from the second distribution mechanism 20 to the first transporter 11 of the first distribution mechanism 10, and is a last time at which a human contacted the article transported or stored by the second distribution mechanism 20 (hereinafter referred to as "second time"). The information processing device 100 manages the second time in order to enable setting of the initial first time on the basis of the second time.

Figure 2:
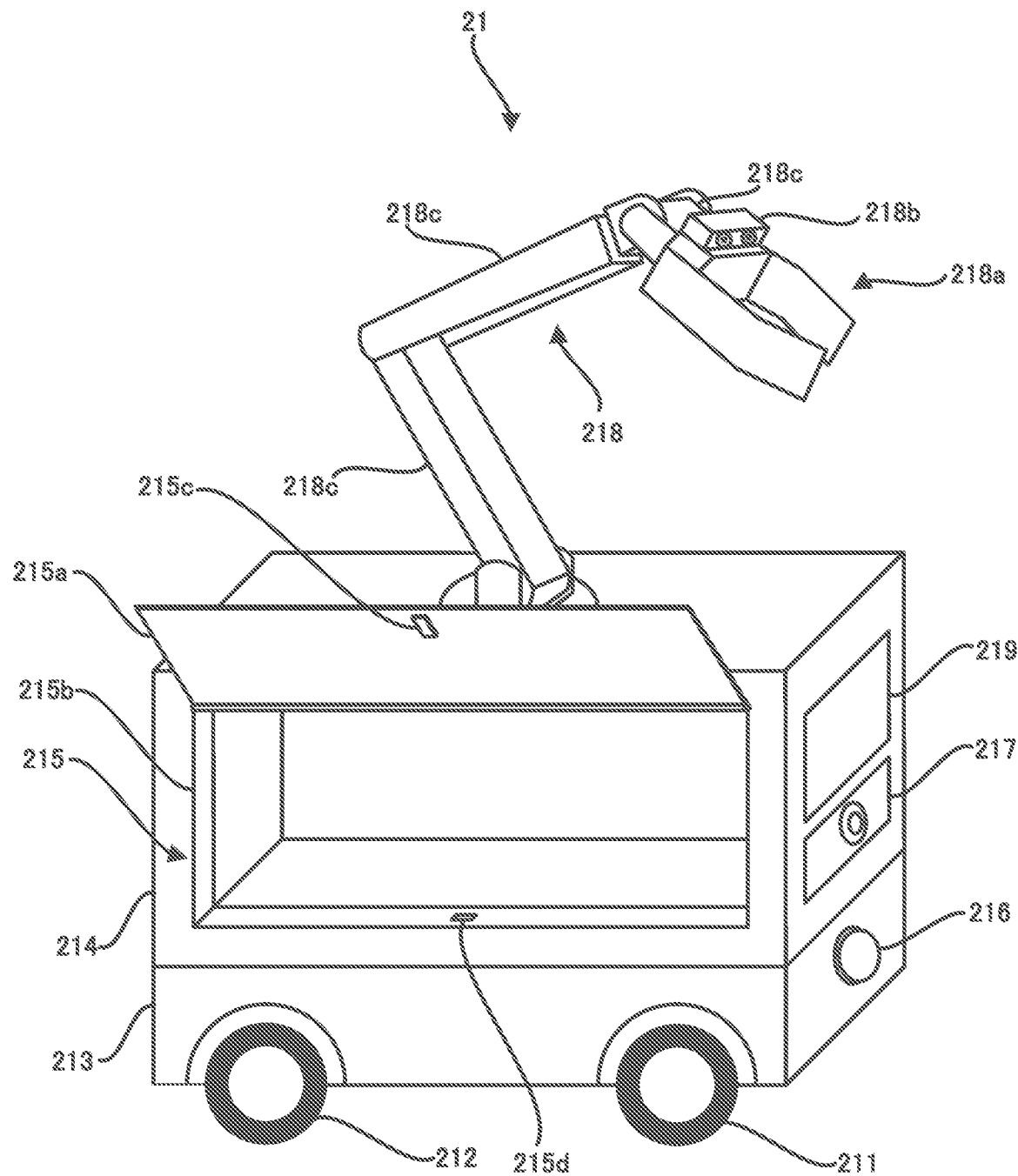
FIG. 2 is an appearance configuration drawing illustrating an example of the appearance of a second transporter according to Embodiment 1.

The second transporter 21 that executes the first procedure is implemented as an unmanned ground vehicle such as illustrated in FIG. 2, and is disposed at a warehouse of a distributor where entry by humans is forbidden. As such, a human does not ride the second transporter 21.

The second transporter 21 includes a chassis 213 including a plurality of wheels including wheels 211 and 212, a storage locker 214 arranged on a top surface of the chassis 213, and a control device 219 installed in the storage locker 214.

The storage locker 214 of the second transporter 21 includes one storage box 215. The storage box 215 includes one bottom plate, ceiling plate, and back plate, and two side plates that are non-illustrated. The storage box 215 has a box body that forms a space enclosed by these plates and that has an open front. A door frame 215b that receives a door 215a is installed in the opening of the box body. The door 215a includes a deadbolt 215c that is a bolt, and the door frame 215b includes a strike plate 215d that is a seat for the deadbolt 215c.

The door 215a of the storage locker 214 of the second transporter 21 further includes a non-illustrated motor that locks the door 215a by inserting the deadbolt 215c into the strike plate 215d in accordance with a signal output from the control device 219. The motor unlocks the door 215a by pulling the deadbolt 215c from the strike plate 215d in accordance with a signal output from the control device 219.

The second transporter 21 further includes a light detection and ranging (LiDAR) sensor 216 provided on the front surface of the chassis 213, and a non-illustrated LiDAR sensor provided on the back surface of the chassis 213.

The LiDAR sensor 216 on the front surface of the second transporter 21 emits laser light in a plurality of directions such that, when the forward direction of the second transporter 21 is used as a reference direction, an azimuth formed with that reference direction is in a range of −90 degrees to +90 degrees and an elevation angle formed with the forward direction of the second transporter 21 is in a range of −90 degrees to +90 degrees. The LiDAR sensor 216 on the front surface receives the reflected light of the emitted laser light, and measures the distance to a plurality of reflection points at which the laser light reflects. The distance is measured on the basis of an amount of time from the emission of the laser light to the receiving of the reflected light. Next, for the plurality of reflection points, the LiDAR sensor 216 calculates, on the basis of the emission direction of the laser light and the measured distance, coordinate values in a three-dimensional coordinate system of the second transporter 21 in which the center point of the second transporter 21 is used as the origin point. Thereafter, the LiDAR sensor 216 on the front surface outputs the calculated coordinate values of the plurality of reflection points to the control device 219.

The LiDAR sensor on the back surface of the second transporter 21 emits infrared laser light in a plurality of directions such that, when the backward direction of the second transporter 21 is used as the reference direction, an azimuth formed with that reference direction is in a range of −90 degrees to +90 degrees and an elevation angle formed with the backward direction of the second transporter 21 is in a range of −90 degrees to +90 degrees. Additionally, the LiDAR sensor on the back surface calculates the coordinate values in the three-dimensional coordinate system of the second transporter 21 for the plurality of reflection points of the emitted laser light, and outputs the calculated coordinate values of the plurality of reflection points to the control device 219.

The reason that LiDAR sensor 216 on the front surface and the LiDAR sensor on the back surface of the second transporter 21 output the coordinate values of the plurality of reflection points to the control device 219 is because the control device 219 identifies the coordinate values, the sizes, and the like in three-dimensional space of objects in all directions based on the second transporter 21 in order to travel while avoiding objects such as obstacles and the like, for example.

Furthermore, the second transporter 21 includes an imaging device 217 that is provided on the front surface of the storage locker 214 and of which the optical axis and angle of view are adjusted such that space in front of the second transporter 21 can be imaged. The imaging device 217 is implemented as a digital monaural camera. In one example, the imaging device 217 captures images in front of the second transporter 21 at a predetermined cycle such as one time every one second, and outputs image signals expressing the images obtained by the imaging to the control device 219.

The second transporter 21 further includes a robot arm 218 that is provided on the top surface of the storage locker 214. The robot arm 218 is implemented as a vertical articulated robot. The robot arm 218 includes a drive circuit that drives a non-illustrated motor in accordance with control signals output from the control device 219, and a two-claw-type gripper 218a that is opened and closed in parallel by the motor.

The robot arm 218 of the second transporter 21 also includes an imaging device 218b that is mounted on the gripper 218a and that has an optical axis and an angle of view that are adjusted such that the tips of the claws of the gripper 218a are included in the imaging range, a plurality of joint structures that can be moved by non-illustrated motors, and a plurality of arms 218c that move around the joint structures. The gripper 218a is not limited to two-claw-type grippers and may have three or more claws, or may include a plurality of fingers instead of the two claws.

The imaging device 218b of the robot arm 218 of the second transporter 21 is implemented as a digital stereo camera. The imaging device 218b performs imaging in accordance with signals output from the control device 219, and outputs, to the control device 219, a signal expressing two images that have parallax with each other. Such a signal is output to the control device 219 because the control device 219 identifies, on the basis of the parallax of the two images, the positional coordinates in three dimensional space, the size, and the like of the article to be gripped by the gripper 218a.

Figure 3:
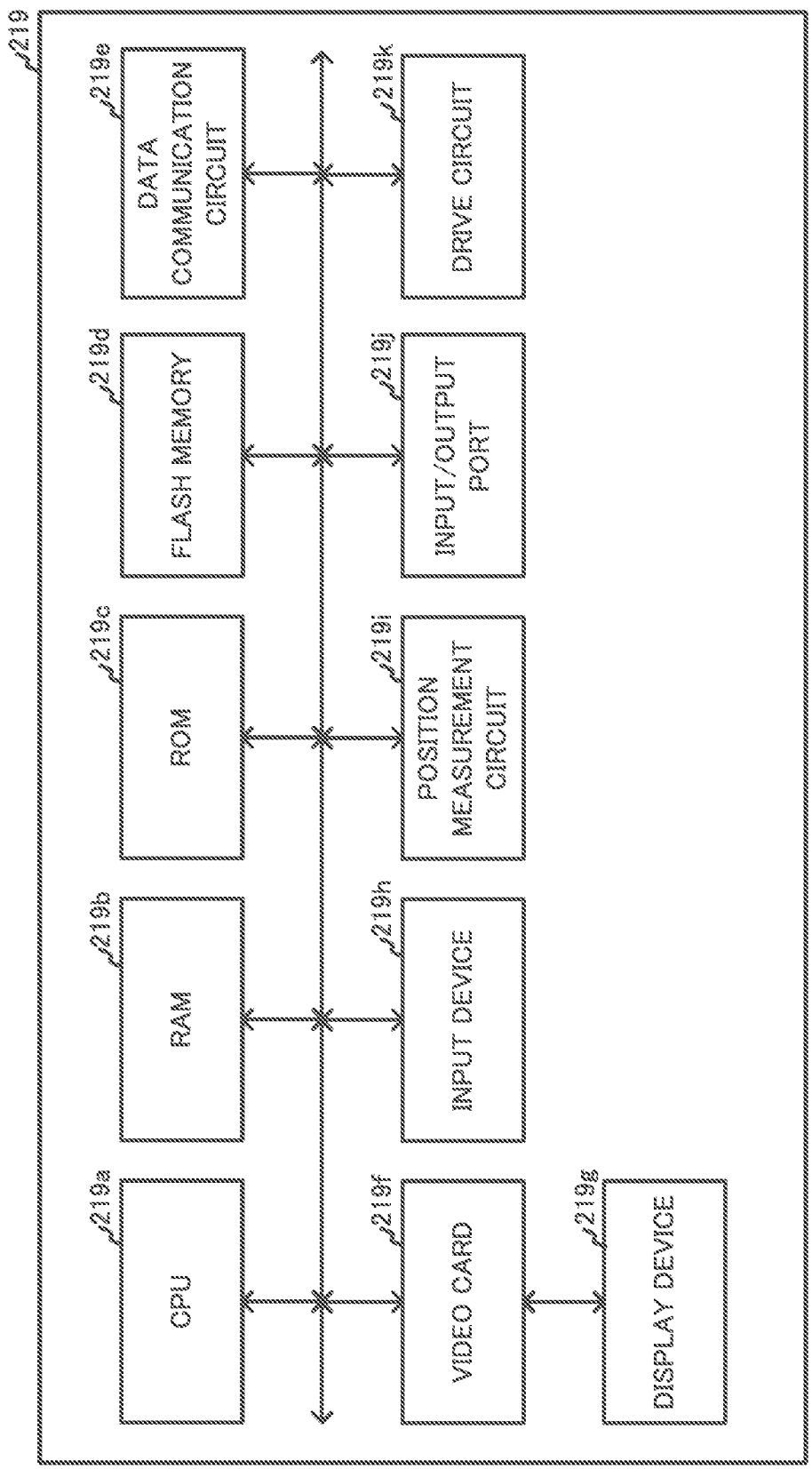
FIG. 3 is a hardware configuration drawing illustrating a configuration example of a control device of the second transporter.

The control device 219 of the second transporter 21 includes hardware such as illustrated in FIG. 3. The hardware of the control device 219 includes a central processing unit (CPU) 219a, a random access memory (RAM) 219b, a read-only memory (ROM) 219c, a flash memory 219d, a data communication circuit 219e, a video card 219f, a display device 219g, an input device 219h, a position measurement circuit 219i, an input/output port 219j, and a drive circuit 219k. In the present embodiment, the second transporter 21 includes one CPU 219a, but may include a plurality of CPUs. Additionally, the second transporter 21 may include a plurality of RAMs and flash memories.

The CPU 219a of the second transporter 21 carries out total control of the second transporter 21 by executing programs stored in the ROM 219c or the flash memory 219d. The RAM 219b temporarily stores data to be processed at the time of execution of the programs by the CPU 219a.

Various types of programs are stored in the ROM 219c and the flash memory 219d of the second transporter 21. The flash memory 219d also stores various types of data and tables in which data is stored that are used in the execution of the programs. The second transporter 21 may include a hard disk instead of the flash memory 219d.

In one example, the data communication circuit 219e of the second transporter 21 is implemented as a network interface card (NIC) and, in accordance with a communication standard such as transmission control protocol (TCP)/internet protocol (IP), carries out data communication using radio waves with a non-illustrated access point that is connected to a local area network LN. Thus, the data communication circuit 219e of the second transporter 21 carries out data communication with the depository 22 and the information processing device 100 that are connected to the local area network LN.

The video card 219f of the second transporter 21 renders images on the basis of digital signals output from the CPU 219a, and outputs image signals that represent the rendered images. The display device 219g is implemented as an electroluminescence (EL) display, and displays images in accordance with the image signals output from the video card 219f. The second transporter 21 may include a plasma display panel (PDP) or a liquid crystal display (LCD) instead of the EL display. The input device 219h is implemented as at least one of a keyboard, a mouse, a touch pad, or a button, and outputs signals corresponding to operations performed by a worker of the carrier.

The position measurement circuit 219i of the second transporter 21 is implemented as a quasi-zenith satellite system (QZSS) circuit. The position measurement circuit 219i receives a signal emitted from a quasi-zenith satellite, measures the latitude, longitude, and altitude expressing the position of the second transporter 21 on the basis of the received signal, and outputs a signal expressing the measured latitude, longitude, and altitude. A configuration is possible in which, instead of a QZSS circuit, the position measurement circuit 219i is implemented as a global positioning system (GPS) circuit that receives a GPS signal emitted from a GPS satellite, and measures the latitude, longitude, and altitude expressing the position of the second transporter 21 on the basis of the received GPS signal.

The input/output port 219j of the second transporter 21 is connected, via non-illustrated cables, to the LiDAR sensor 216 on the front surface and the LiDAR sensor on the back surface. The input/output port 219j inputs, to the CPU 219a, the signals expressing the coordinate values outputted by each of the LiDAR sensor 216 on the front surface and the LiDAR sensor on the back surface.

The input/output port 219j of the second transporter 21 is connected, via non-illustrated cables, to the imaging device 217 arranged on the front surface of the storage locker 214 and the imaging device 218b of the robot arm 218, and inputs, into the CPU 219a, image signals output by the imaging devices 217 and 218b.

Furthermore, the input/output port 219j of the second transporter 21 is connected to the robot arm 218 via a non-illustrated cable, and inputs, into the robot arm 218, control signals output by the CPU 219a.

The drive circuit 219k is connected to non-illustrated cables that are respectively connected to the non-illustrated motors that rotate the plurality of wheels. The drive circuit 219k causes the plurality of wheels to rotate by driving the motors in accordance with control signals output by the CPU 219a.

The drive circuit 219k is connected to a cable connected to the non-illustrated motor that pulls the deadbolt 215c of the door 215a out of the strike plate 215d or inserts the deadbolt 215c into the strike plate 215d, and drives the motor in accordance with signals output by the CPU 219a.

When the worker of the carrier arrives at the warehouse of the distributor, the worker operates a non-illustrated terminal device and, in accordance with the operation, the terminal device sends, to the information processing device 100, a notification informing of the arrival at the office. When the notification is received, the information processing device 100 sends, to the second transporter 21, an execution command commanding the execution of the undertaking procedure in which the article is undertaken from the carrier.

Figure 4:
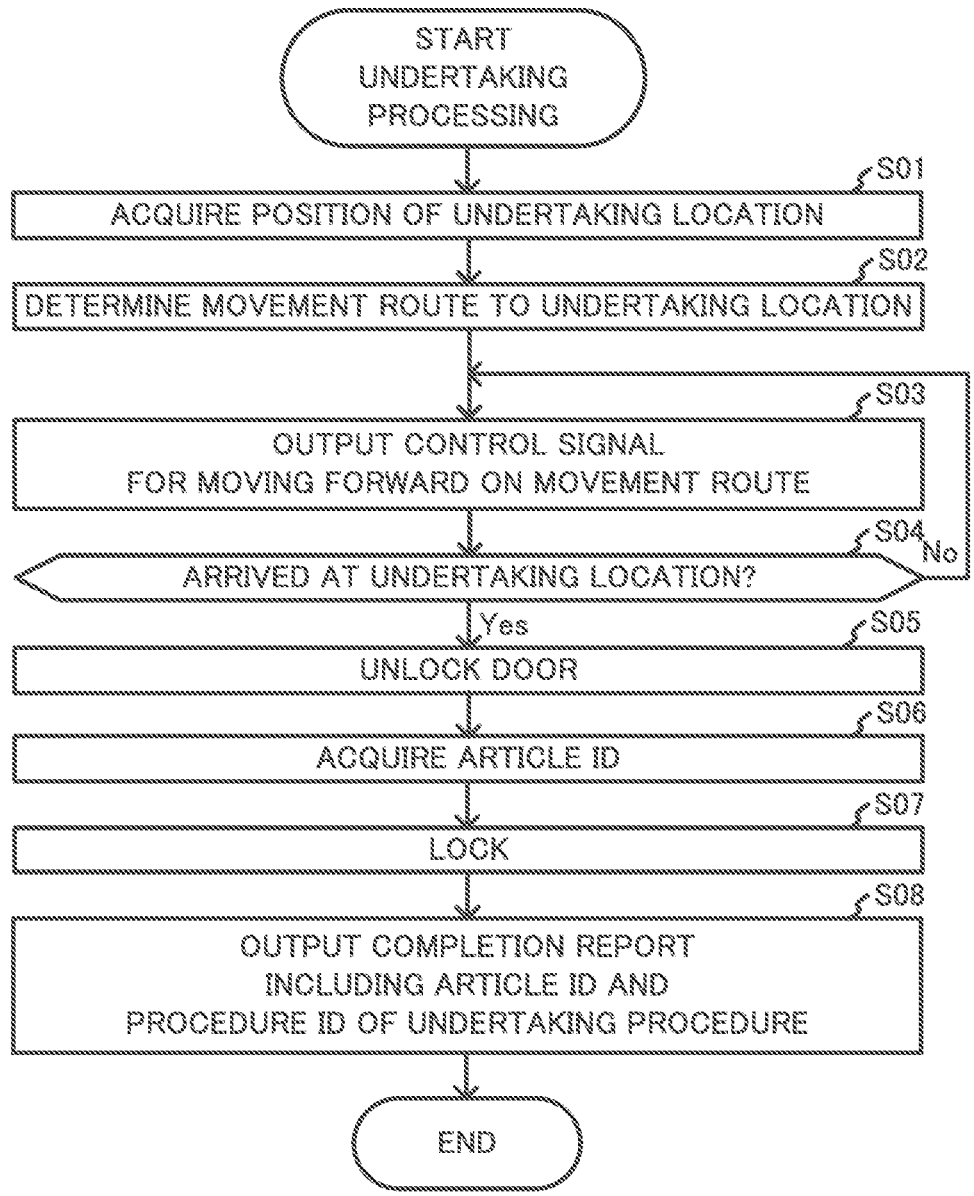
FIG. 4 is a flowchart illustrating an example of undertaking processing executed by the second transporter.

When the data communication circuit 219e of the second transporter 21 receives the execution command, the CPU 219a executes undertaking processing such as illustrated in FIG. 4 to perform the undertaking procedure in accordance with the execution command.

When the execution of the undertaking processing starts, the CPU 219a of the second transporter 21 acquires, from the flash memory 219d, information expressing, in terms of latitude, longitude, and altitude, the position of a predetermined undertaking location (step S01). In the present embodiment, the undertaking location is a loading bay of the warehouse, but is not limited thereto.

Next, the CPU 219a of the second transporter 21 identifies the latitude, longitude, and altitude of the second transporter 21 on the basis of a signal output from the position measurement circuit 219i. Then, the CPU 219a of the second transporter 21 reads, from the flash memory 219d, a non-illustrated partial route table in which information related to partial routes on which the second transporter 21 can move, such as the corridors of the warehouse, are stored in advance, and reads a plurality of records from the read partial route table. The latitude, longitude, and altitude of a start node of a partial route, the latitude, longitude, and altitude of an end node of the partial route, and a length of an edge that is the partial route are associated and stored in advance in each record of the partial route table.

The CPU 219a of the second transporter 21 executes a route search algorithm such as, for example, Dijkstra's algorithm using the identified latitude, longitude, and altitude of the second transporter 21, and the length of the edge that is the partial route, the latitude, longitude, and altitude of the nodes, and the latitude, longitude, and altitude of the undertaking location stored in each of the read plurality of records. As a result, the CPU 219a calculates the shortest overall route from the position of the second transporter 21 to the undertaking location, and determines the calculated overall route as a movement route (step S02).

Next, in order to move forward on the movement route, the CPU 219a of the second transporter 21 identifies the latitude, longitude, and altitude of the second transporter 21 on the basis of a signal output from the position measurement circuit 219i. Then, the CPU 219a generates a control signal for traveling so as to reduce the difference between the identified latitude, longitude, and altitude and the latitude, longitude, and altitude of the next closest node in an arrival order of the plurality of nodes not yet arrived at included in the flight route. Then, the CPU 219a outputs the generated control signal to the drive circuit 219k (step S03), and the drive circuit 219k causes the plurality of wheels to rotate in accordance with the control signal.

Thereafter, since the second transporter 21 has not arrived at all of the one or plurality of nodes included in the movement route, the CPU 219a of the second transporter 21 determines that the second transporter 21 has not arrived at the undertaking location (step S04; No), and repeats the processing described above from step S03. In contrast, when all of the one or plurality of nodes included in the movement route have been arrived at and, as such, the CPU 219a determines that the second transporter 21 has arrived at the undertaking location (step S04; Yes), the CPU 219a outputs, to the drive circuit 219k, a control signal for unlocking the door 215a of the storage locker 214 to cause the deadbolt 215c to be pulled out of the strike plate 215d (step S05).

Thereafter, the worker of the carrier moves to in front of the second transporter 21 while holding the article in their hands. When the imaging device 217 of the second transporter 21 images the article held by the worker and an image signal expressing the image obtained by the imaging is inputted by the input/output port 219j, the CPU 219a of the second transporter 21 performs pattern matching, for example. As a result, the CPU 219a detects, from the image expressed by the image signal, an image region corresponding to the imaged article. In the pattern matching, the CPU 219a uses information, stored in advance in the flash memory 219d, that expresses a pattern of the article. Next, the CPU 219a executes optical character recognition (OCR) processing, for example, on the detected image region to acquire an article identification (ID) that is printed on the article or on the packaging of the article (step S06).

In the present embodiment, the article ID identifying the article is a combination of a product number of the article and an individual identification number that is, for example, a serial number assigned to the article by the manufacturer or the seller of the article. However, the present embodiment is not limited thereto.

Next, the worker of the carrier places the article in the storage locker 214 of the second transporter 21 by hand and, then, performs an operation on the input device 219h for locking the door 215a of the storage locker 214. When the input device 219h of the second transporter 21 outputs a signal corresponding to the operation, the CPU 219a outputs, to the drive circuit 219k, a control signal for locking the door 215a of the storage locker 214, thereby causing the deadbolt 215c to be inserted into the strike plate 215d (step S07).

Thereafter, the CPU 219a of the second transporter 21 generates a completion report that includes the acquired article ID and a procedure ID identifying the undertaking procedure in which the article identified by the article ID is undertaken, and that informs that the undertaking procedure is completed. Next, the CPU 219a of the second transporter 21 outputs the generated completion report to the data communication circuit 219e with the information processing device 100 as the destination (step S08). After the data communication circuit 219e sends the completion report to the information processing device 100, the CPU 219a of the second transporter 21 ends the execution of the undertaking processing.

Thus, in the present embodiment, in order to perform the undertaking procedure, the worker of the carrier must use their hands to store the article in the second transporter 21 and, as such, a human is involved in the undertaking procedure. In the present embodiment, the phrase "a human is involved in the procedure" means that a human must physically touch the article to perform that procedure.

As such, when the information processing device 100 receives/acquires the completion report informing that the undertaking procedure is completed, the information processing device 100 manages the time at which the completion report is acquired as the second time. Then, the information processing device 100 sends, to the second transporter 21, an execution command commanding the execution of the transport to depository procedure in order to cause the second transporter 21 to transport the undertaken article to the depository 22.

Figure 5:
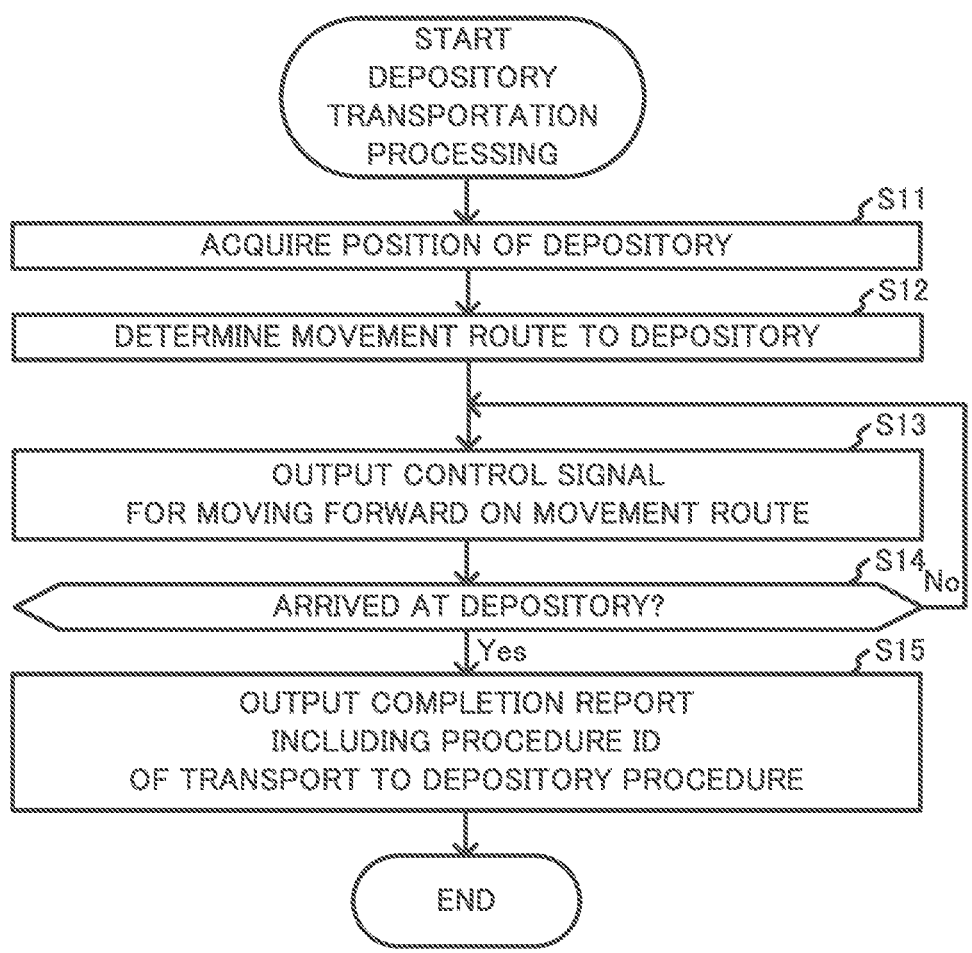
FIG. 5 is a flowchart illustrating an example of depository transportation processing executed by the second transporter.

When the data communication circuit 219e of the second transporter 21 receives this execution command, the CPU 219a executes depository transportation processing such as illustrated in FIG. 5 to perform the transport to depository procedure in accordance with the execution command.

When the execution of the depository transportation processing starts, the CPU 219a of the second transporter 21 acquires, from the flash memory 219d, the information expressing, in terms of latitude, longitude, and altitude, the position of the depository 22 (step S11). Next, the CPU 219a executes the same processing as steps S02 to S04 of FIG. 4 (steps S12 to S14), and transports the article to the depository 22. Then, the CPU 219a outputs, to the data communication circuit 219e with the information processing device 100 as the destination, a completion report that includes the procedure ID of the transport to depository procedure and that informs that the transport to depository procedure is completed (step S15). After the data communication circuit 219e sends the completion report to the information processing device 100, the CPU 219a of the second transporter 21 ends the execution of the depository transportation processing.

Thus, in the present embodiment, the second transporter 21 that is an unmanned ground vehicle performs the entire transport to depository procedure and, as such, a human is not involved in the transport to depository procedure. As such, the information processing device 100 maintains the second time without updating the second time, even when a completion report is received that informs that the transport to depository procedure is completed.

Figure 6:
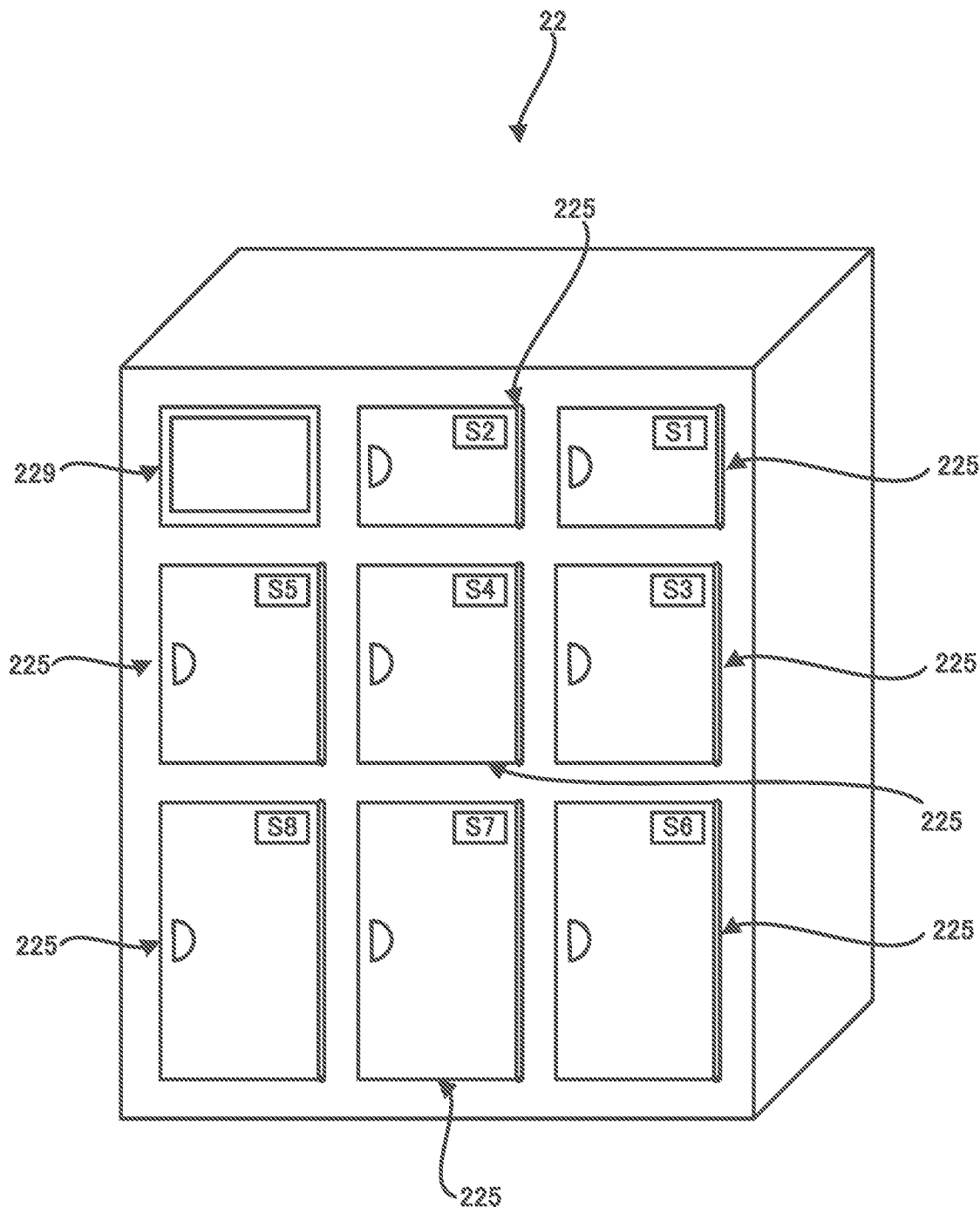
FIG. 6 is an appearance configuration drawing illustrating an example of the appearance of the depository.

The depository 22 includes a plurality of storage boxes 225 such as illustrated in FIG. 6 that is used to store the article, and a control device 229 that controls locking and unlocking of each of the plurality of storage boxes 225.

Each of the plurality of storage boxes 225 of the depository 22 includes a box body and a door that are non-illustrated, and a door frame installed in an opening of the box body. Each door includes a non-illustrated deadbolt that is a bolt, and each door frame includes a non-illustrated strike plate that is a seat for the deadbolt. The configurations and functions of the box body, the door, the door frame, the deadbolt, and the strike plate of each of the plurality of storage boxes 225 are the same as the configurations and functions of the box body, the door 215a, the door frame 215b, the deadbolt 215c, and the strike plate 215d of the storage box 215 of the second transporter 21.

The control device 229 of the depository 22 includes, as hardware, a CPU, a RAM, a ROM, a flash memory, a data communication circuit, a video card, a display device, an input device, an input/output port, and a drive circuit that are non-illustrated. The configurations and functions of the hardware of the control device 229 of the depository 22 are the same as the configurations and functions of the hardware of the control device 219 of the second transporter 21. In the present embodiment, the depository 22 includes one CPU, but may include a plurality of CPUs. Additionally, the depository 22 may include a plurality of RAMs and flash memories.

When the completion report informing that the transport to depository procedure is completed is received from the second transporter 21 that transports the article to the depository 22, the information processing device 100 sends, to the second transporter 21, an execution command commanding the execution of the store in depository procedure.

Figure 7:
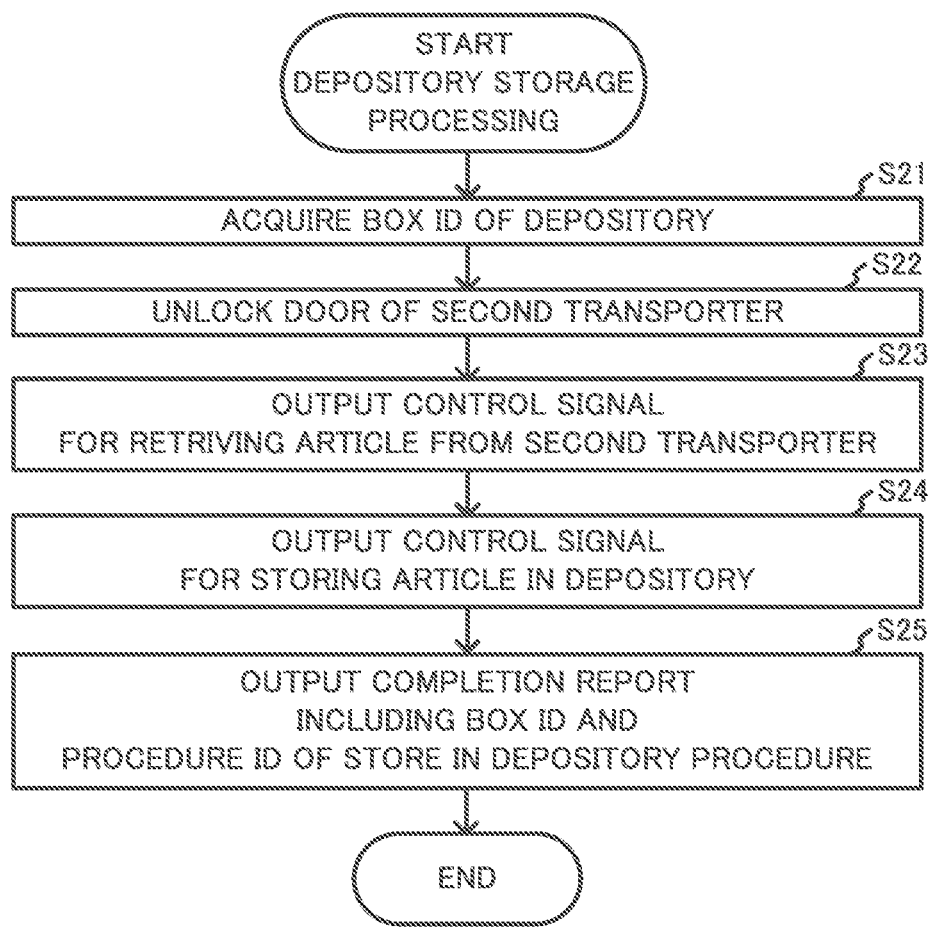
FIG. 7 is a flowchart illustrating an example of depository storage processing executed by the second transporter.

When the data communication circuit 219e of the second transporter 21 receives this execution command, the CPU 219a executes depository storage processing such as illustrated in FIG. 7 to perform the store in depository procedure in accordance with the execution command.

When the execution of the depository storage processing starts, the CPU 219a of the second transporter 21 generates, on the basis of the latitude, longitude, and altitude of the second transporter 21 and the latitude, longitude, and altitude of the depository 22, a control signal for changing the optical axis of the imaging device 218b of the robot arm 218 so as to enable imaging one of the plurality of storage boxes 225 of the depository 22. Next, the CPU 219a outputs, to the imaging device 218b via the input/output port 219j, the generated control signal and a control signal commanding imaging to be performed.

Next, the CPU 291a acquires two images on the basis of signals output from the imaging device 218b, and executes OCR processing, for example, on one of the two acquired images. As a result, the CPU 219a acquires a box ID that is a number displayed on the door of the imaged storage box 225, and that identifies that storage box 225 (step S21).

Next, the CPU 219a of the second transporter 21 calculates, on the basis of the parallax of the acquired two images, coordinate values expressing the position and the shape of the imaged door. In the present embodiment, the coordinate values calculated by the CPU 219a are coordinate values in a three-dimensional coordinate system that uses the center point of the second transporter 21 as the origin, but the present embodiment is not limited thereto.

Thereafter, the CPU 219a of the second transporter 21 outputs, on the basis of the calculated coordinate values, to the robot arm 218, a control signal for causing the robot arm 218 to open the imaged door. The robot arm 218 opens the door of the depository 22 in accordance with the control signal.

Next, the CPU 219a of the second transporter 21 outputs, to the drive circuit 219k, a control signal for unlocking the door 215a of the storage locker 214 of the second transporter 21 (step S22).

Thereafter, the CPU 219a of the second transporter 21 acquires, from the flash memory 219d, coordinate values expressing the position and the shape of the door 215a of the storage locker 214 of the second transporter 21. Then, the CPU 219a outputs, on the basis of the acquired coordinate values, to the robot arm 218, a control signal for causing the robot arm 218 to open the door 215a. The robot arm 218 opens the door 215a of the second transporter 21 in accordance with the control signal.

Thereafter, the CPU 219a of the second transporter 21 generates, on the basis of the coordinate values acquired from the flash memory 219d, a control signal for changing the optical axis of the imaging device 218b of the robot arm 218 so as to enable imaging the opening and interior of the box body of the storage locker 214 of the second transporter 21. Next, the CPU 219a outputs, to the robot arm 218, the generated control signal and a control signal commanding imaging to be performed. Then, the CPU 219a acquires two images on the basis of signals output from the imaging device 218b, and calculates, on the basis of the parallax of the two acquired images, coordinate values of the position and the shape of the article stored in the box body of the storage locker 214. Next, the CPU 219a outputs, on the basis of the calculated coordinate values, to the robot arm 218, a control signal for causing the robot arm 218 to grip the article stored in the storage locker 214 and retrieve the article from the storage locker 214 (step S23). The robot arm 218 grips the article stored in the storage locker 214 and retrieves the article from the storage locker 214 in accordance with the control signal.

Thereafter, the CPU 219a of the second transporter 21 generates a control signal for changing, on the basis of the coordinate values expressing the position of the unopened door of the depository 22, the optical axis of the imaging device 218b of the robot arm 218 so as to enable imaging the opening and interior of the storage box 215 after the door is opened. Next, the CPU 219a outputs, to the robot arm 218, the generated control signal and a control signal commanding imaging to be performed. Then, the CPU 219a calculates, on the basis of the parallax of the two images expressed by signals output from the imaging device 218b, coordinate values expressing the position and shape of the opening of the box body, and the depth of the box body. Next, the CPU 219a outputs, on the basis of the calculated coordinate values and depth, a control signal to the robot arm 218 for causing the robot arm 218 to insert the article retrieved from the second transporter 21 through the opening and into the storage box 225 of the depository 22 (step S24). The robot arm 218 stores the article in the depository 22 in accordance with the control signal.

Thereafter, the CPU 219a of the second transporter 21 outputs, to the robot arm 218, a control signal for closing the door 225a of the second transporter 21 and the door of the depository 22 that are opened by the robot arm 218.

Thereafter, the CPU 219a of the second transporter 21 generates a completion report that includes the box ID identifying the storage box 225 of the depository 22 in which the article is stored and the procedure ID of the store in depository procedure, and that informs that the store in depository procedure is completed. Next, the CPU 219a of the second transporter 21 outputs the generated completion report to the data communication circuit 219e with the information processing device 100 as the destination (step S25). After the data communication circuit 219e sends the completion report to the information processing device 100, the CPU 219a of the second transporter 21 ends the execution of the depository storage processing.

Thus, in the present embodiment, the second transporter 21 performs the entire store in depository procedure and, as such, a human is not involved in the store in depository procedure. As such, the information processing device 100 does not update the second time, even when a completion report is received that informs that the store in depository procedure is completed. Then, the information processing device 100 sends, to the depository 22, a locking command that includes the box ID included in the completion report and that commands locking of the storage box 225 identified by that box ID.

When the non-illustrated data communication circuit of the depository 22 receives the locking command, the CPU of the depository 22 acquires the box ID included in the locking command, and outputs, to the drive circuit, a control signal for locking the storage box 225 identified by the acquired box ID. As a result, the storage box 225 is locked.

Figure 8:
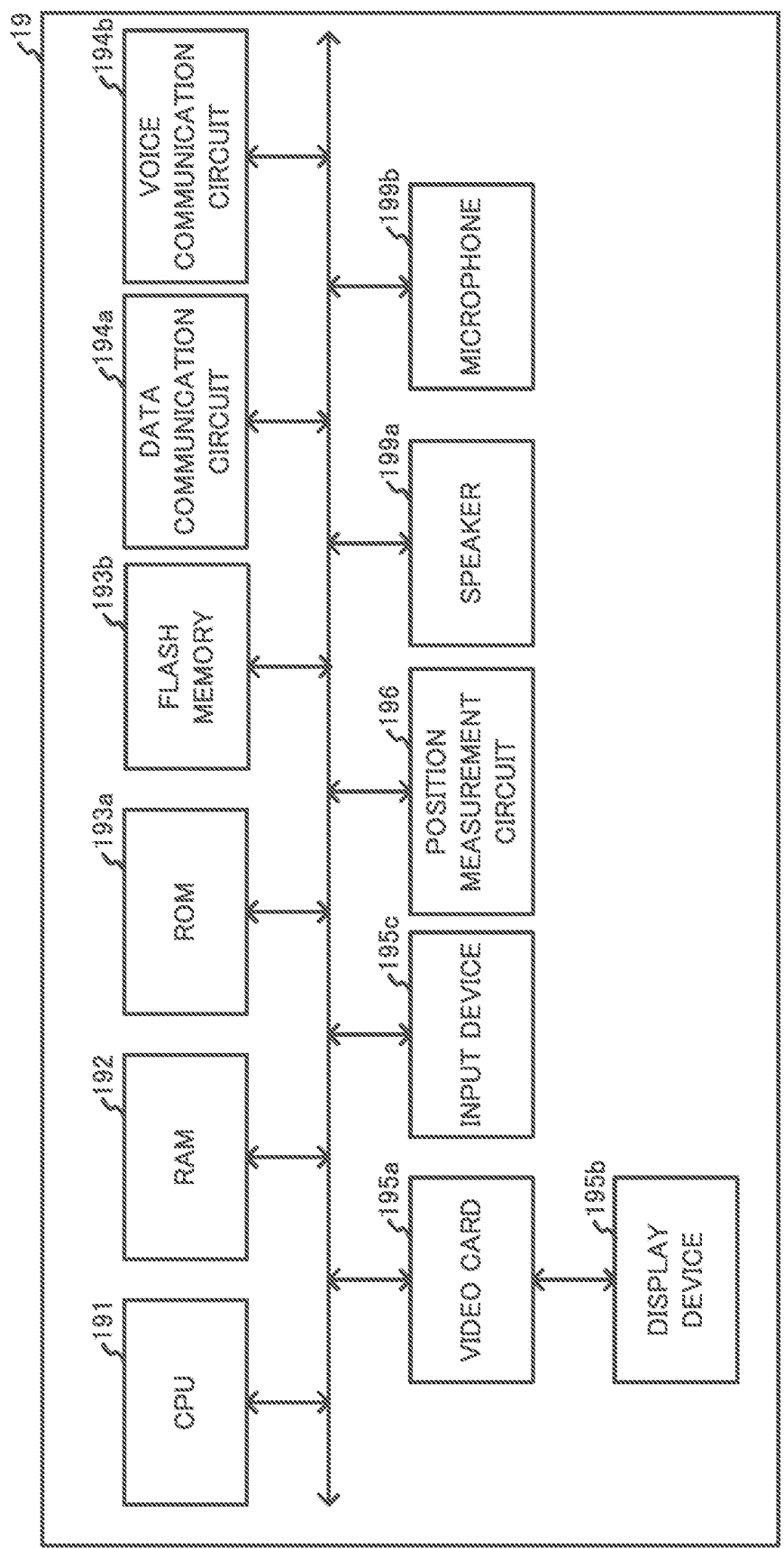
FIG. 8 is a hardware configuration diagram illustrating a configuration example of a terminal device.

The terminal device 19 carried by the buyer is implemented, for example, as a smartphone and, as illustrated in FIG. 8, includes a CPU 191, a RAM 192, a ROM 193a, a flash memory 193b, a data communication circuit 194a, a voice communication circuit 194b, a video card 195a, a display device 195b, an input device 195c, a position measurement circuit 196, a speaker 199a, and a microphone 199b. In the present embodiment, the terminal device 19 includes one CPU 191, but may include a plurality of CPUs. Additionally, the terminal device 19 may include a plurality of RAMs and flash memories.

The configurations and functions of the CPU 191, the RAM 192, the ROM 193a, the flash memory 193b, the data communication circuit 194a, the video card 195a, the display device 195b, the input device 195c, and the position measurement circuit 196 of the terminal device 19 are the same as the configurations and functions of the CPU 219a, the RAM 219b, the ROM 219c, the flash memory 219d, the data communication circuit 219e, the video card 219f, the display device 219g, the input device 219h, and the position measurement circuit 219i of the control device 219 of the second transporter 21 illustrated in FIG. 3.

The voice communication circuit 194b of the terminal device 19 carries out voice communication with a non-illustrated base station using radio waves. The speaker 199a outputs sound in accordance with signals output by the CPU 191, and the microphone 199b outputs signals expressing ambient sound of the terminal device 19.

The buyer operates the input device 195c of the terminal device 19 to buy an article. When the input device 195c of the terminal device 19 outputs a signal corresponding to that operation, the CPU 191 acquires, on the basis of that signal, the product number of the article being purchased, and information expressing the address of a destination specified by the buyer. Next, the CPU 191 generates a sale request that includes the product number and the information expressing the address of the destination, and that requests that the article to which that product number is assigned is sold and transported to the destination. Then, the CPU 191 of the terminal device 19 outputs the generated sale request to the data communication circuit 194a with the information processing device 100 as the destination.

When the information processing device 100 receives the sale request from the data communication circuit 194a of the terminal device 19, the information processing device 100 selects, from among one or a plurality of articles stored in the depository 22, one article to which the product number included in the sale request is assigned, and sells the selected article to the buyer. Next, the information processing device 100 sends, to the second transporter 21, an execution command that includes the box ID identifying the storage box 225 of the depository 22 in which the sold article is stored, and that commands the execution of the retrieval procedure.

Figure 9:
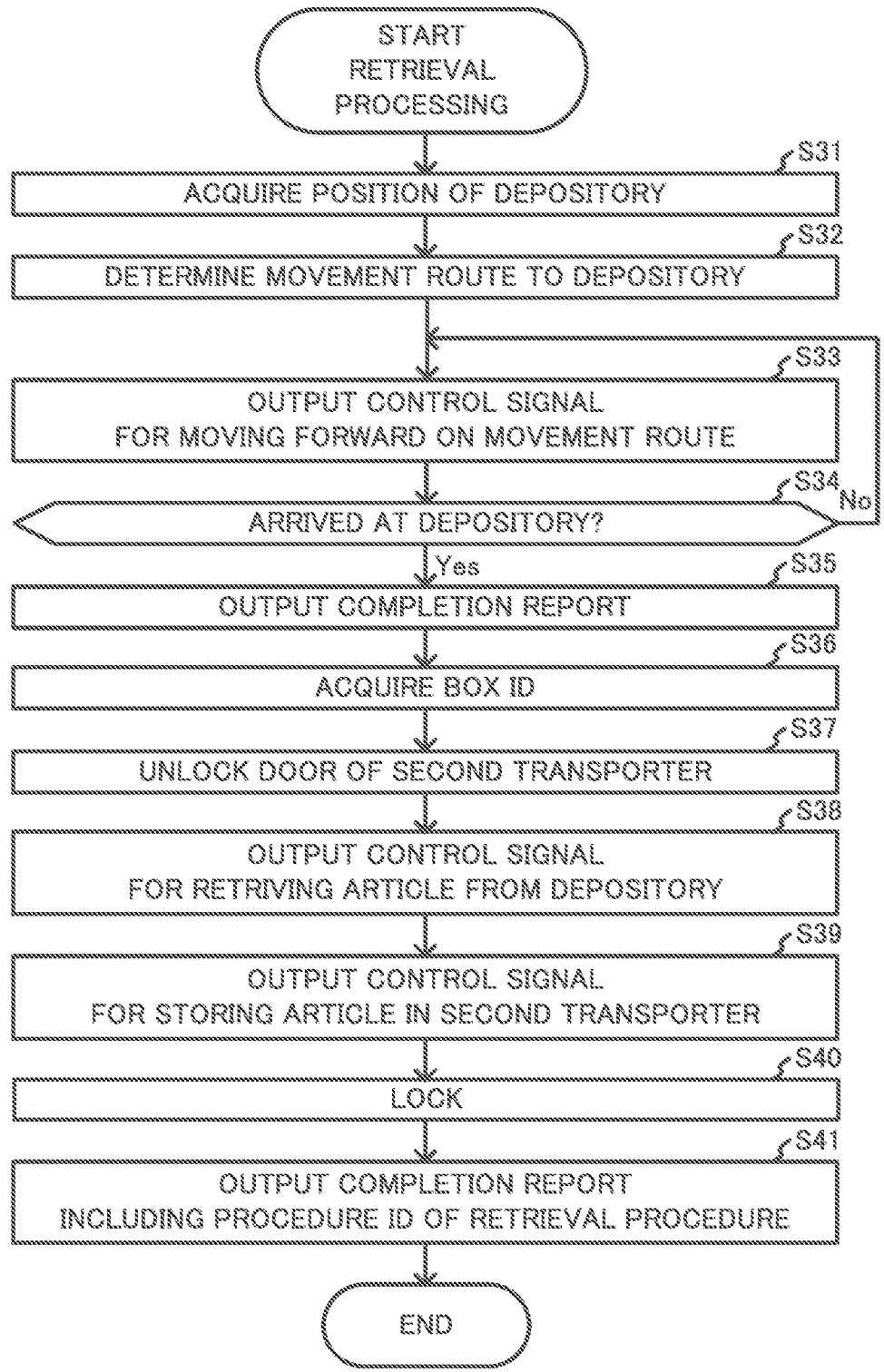
FIG. 9 is a flowchart illustrating an example of retrieval processing executed by the second transporter according to Embodiment 1.

When the data communication circuit 219e of the second transporter 21 receives the execution command, the CPU 219a executes retrieval processing such as illustrated in FIG. 9 to perform the retrieval procedure in accordance with the execution command.

When the execution of the retrieval processing starts, the CPU 219a of the second transporter 21 executes the same processing as steps S11 to S14 of FIG. 5 (steps S31 to S34). As a result, the second transporter 21 moves to the depository 22.

Thereafter, the CPU 219a of the second transporter 21 outputs, to the data communication circuit 219e with the information processing device 100 as the destination, an arrival report informing that the second transporter 21 has arrived at the depository 22 (step S35).

When the information processing device 100 receives the arrival report, the information processing device 100 sends, to the depository 22, an unlocking command that includes the box ID of the storage box 225 in which the sold article is stored, and that commands unlocking of that storage box 225. When the non-illustrated data communication circuit of the depository 22 receives the unlocking command, the CPU of the depository 22 outputs, to the drive circuit, a control signal for unlocking the storage box 225 identified by the box ID included in the unlocking command.

After the arrival report is output in step S35, the CPU 219a of the second transporter 21 acquires the box ID from the execution command received by the data communication circuit 219e (step S36).

The CPU 219a of the second transporter 21 generates a control signal for changing the optical axis of the imaging device 218b of the robot arm 218 so as to enable imaging of one of the plurality of storage boxes 225 of the depository 22. Next, the CPU 219a executes processing for outputting, to the imaging device 218b, the generated control signal and a control signal commanding imaging to be performed. Then, the CPU 219a acquires two images on the basis of signals output from the imaging device 218b, and acquires, from one of the two acquired images, the box ID displayed on the door of the imaged storage box 225.

Next, the CPU 219a of the second transporter 21 determines whether or not the box ID acquired from the execution command and the box ID acquired from the image match. At this time, when the CPU 219a determines that the two box IDs do not match, the CPU 219a generates a control signal for changing the optical axis of the imaging device 218b so as to enable imaging of one storage box 225 of the plurality of storage boxes 225 that has not been imaged. Then, the CPU 219a repeats the processing described above from the processing for outputting, to the imaging device 218b, the generated control signal and the control signal commanding imaging to be performed.

In contrast, when the CPU 219a of the second transporter 21 determines that the two box IDs match, the CPU 219a outputs, on the basis of the parallax of the acquired two images, a control signal to the robot arm 218 for opening the imaged door of the depository 22.

Next, the CPU 219a of the second transporter 21 outputs, to the drive circuit 219k, a control signal for unlocking the door 215a of the storage locker 214 of the second transporter 21 (step S37). Then, the CPU 219a of the second transporter 21 outputs, to the robot arm 218, a control signal for opening the door 215a of the second transporter 21.

Next, the CPU 219a of the second transporter 21 outputs a control signal for changing, on the basis of the coordinate values expressing the position of the unopened door of the depository 22, the optical axis of the imaging device 218b of the robot arm 218 so as to enable imaging of the opening and the interior of the storage box 225 after the door is opened. Thereafter, the CPU 219a outputs a control signal commanding imaging to be performed. Next, the CPU 219a outputs a control signal for gripping, on the basis of the parallax of the two images expressed in the signal output from the imaging device 218b, the article stored in the storage box 225 of the depository 22 and retrieving the article from the storage box 225 (step S38). The robot arm 218 grips the article stored in the storage box 225 and retrieves the article from the storage box 225 in accordance with the outputted control signal.

Next, the CPU 219a of the second transporter 21 acquires, from the flash memory 219d, coordinate values expressing the position and shape of the opening of the box body and the depth of the box body of the storage locker 214 of the second transporter 21. Next, the CPU 219a outputs a control signal for causing the article retrieved from the depository 22 to be inserted through the opening into the storage locker 214 of the second transporter 21 on the basis of the acquired coordinate values and depth (step S39). The robot arm 218 stores the article in the second transporter 21 in accordance with the outputted control signal.

Thereafter, the CPU 219a of the second transporter 21 outputs, to the robot arm 218, a control signal for closing the door 225a of the second transporter 21 and the door of the depository 22 that are opened by the robot arm 218. Then, the CPU 219a of the second transporter 21 outputs, to the drive circuit 219k, a control signal for locking the door 215a of the storage locker 214 of the second transporter 21 (step S40).

Next, the CPU 219a of the second transporter 21 outputs, to the data communication circuit 219e with the information processing device 100 as the destination, a completion report that includes the procedure ID of the retrieval procedure and that informs that that procedure is completed (step S41), and ends the execution of the retrieval processing.

Thus, in the present embodiment, the second transporter 21 performs the entire retrieval procedure and, as such, a human is not involved in the retrieval procedure. As such, the information processing device 100 does not update the second time, even when a completion report is received that informs that the retrieval procedure is completed.

Thereafter, the information processing device 100 sends, to the first transporter 11, a movement command commanding movement to a hand over location predetermined as a location where the article is to be handed over from the second transporter 21 to the first transporter 11. Additionally, the information processing device 100 sends, to the second transporter 21, an execution command commanding the execution of the transport to first transporter procedure. In the present embodiment, the hand over location is a loading bay of a warehouse, but is not limited thereto.

The first transporter 11 includes a non-illustrated plurality of wheels, a chassis including the plurality of wheels, a storage locker arranged on the top surface of the chassis, LiDAR sensors provided on each of the front surface and the back surface of the chassis, an imaging device provided on the front surface of the chassis, a robot arm provided on the top surface of the storage locker, and a control device installed in the storage locker. The configurations and functions of the plurality of wheels, the chassis, the storage locker, the LiDAR sensor on the front surface, the LiDAR sensor on the back surface, the imaging device, the robot arm, and the control device of the first transporter 11 are the same as the configurations and functions of the plurality of wheels, the chassis 213, the storage locker 214, the LiDAR sensor 216 on the front surface, the non-illustrated LiDAR sensor on the back surface, the imaging device 217, the robot arm 218, and the control device 219 of the second transporter 21.

The control device of the first transporter 11 includes, as hardware, a CPU, a RAM, a ROM, a flash memory, a data communication circuit, a video card, a display device, an input device, a position measurement circuit, an input/output port, and a drive circuit that are non-illustrated. The configurations and functions of the hardware of the control device of the first transporter 11 are the same as the configurations and functions of the hardware of the control device 219 of the second transporter 21 illustrated in FIG. 3. In the present embodiment, the first transporter 11 includes one CPU, but may include a plurality of CPUs. Additionally, the first transporter 11 may include a plurality of RAMs and flash memories.

When the data communication circuit of the first transporter 11 receives the movement command, the CPU of the first transporter 11 acquires, from the flash memory, information expressing the latitude, longitude, and altitude of the hand over location. Next, the CPU of the first transporter 11 executes the same processing as steps S02 to S04 of FIG. 4 to move to the hand over location.

When the data communication circuit 219e of the second transporter 21 receives the execution command commanding the transport to first transporter procedure, the CPU 219a of the second transporter 21 executes non-illustrated transport to first transporter processing.

When the transport to first transporter processing starts, the CPU 219a of the second transporter 21 acquires, from the flash memory 219d, information expressing the latitude, longitude, and altitude of the hand over location. Next, the CPU 219a executes the same processing as steps S02 to S04 of FIG. 4 to transport the article to the hand over location. Then, the CPU 219a outputs, to the data communication circuit 219e with the information processing device 100 as the destination, a completion report that includes the procedure ID of the transport to first transporter procedure and that informs that that procedure is completed, and then ends the execution of the transport to first transporter processing.

Thus, in the present embodiment, the second transporter 21 performs the entire transport to first transporter procedure and, as such, a human is not involved in the transport to first transporter procedure. As such, the information processing device 100 does not update the second time, even when a completion report is received that informs that the transport to first transporter procedure is completed. Then, the information processing device 100 sends, to the second transporter 21, an execution command commanding the execution of the hand over procedure in which the article is handed over from the second transporter 21 to the first transporter 11.

Figure 10:
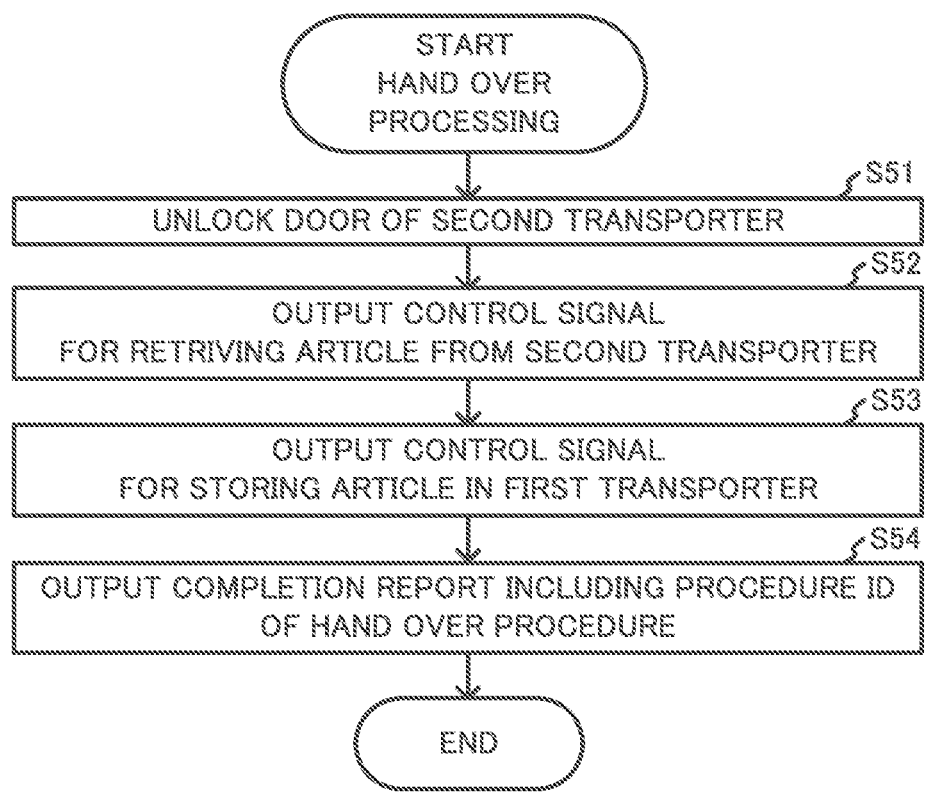
FIG. 10 is a flowchart illustrating an example of hand over processing executed by the second transporter.

When the data communication circuit 219e of the second transporter 21 receives the execution command, the CPU 219a executes hand over processing such as illustrated in FIG. 10 to perform the hand over procedure in accordance with the execution command.

When the execution of the hand over processing starts, the CPU 219a of the second transporter 21 outputs, to the drive circuit 219k, a control signal for unlocking the door 215a of the storage locker 214 of the second transporter 21 (step S51).

Next, the CPU 219a of the second transporter 21 outputs, to the robot arm 218, a control signal for opening the door 215a of the storage locker 214 of the second transporter 21 and the door of the storage locker of the first transporter 11. Then, the CPU 219a of the second transporter 21 executes the same processing as step S23 of FIG. 7 to output, to the robot arm 218, a control signal for retrieving the article stored in the storage locker 214 of the second transporter 21 (step S52).

Thereafter, the same processing as step S24 of FIG. 7 is executed to output, to the robot arm 218, a control signal for storing the article retrieved from the second transporter 21 in the storage locker of the first transporter 11 (step S53). The robot arm 218 stores the article in the storage locker of the first transporter 11 in accordance with the control signal.

Next, the CPU 219a of the second transporter 21 outputs, to the robot arm 218, a control signal for closing the door 225a of the second transporter 21 and the door of the first transporter 11 that the robot arm 218 opened.

Thereafter, the CPU 219a of the second transporter 21 outputs, to the data communication circuit 219e with the information processing device 100 as the destination, a completion report that includes the procedure ID of the hand over procedure and that informs that the hand over procedure is completed (step S25), and ends the execution of the hand over processing.

Thus, in the present embodiment, the second transporter 21 performs the entire hand over procedure and, as such, a human is not involved in the hand over procedure. As such, when the information processing device 100 receives the completion report informing that the hand over procedure is completed, the information processing device 100 manages the second time as the first time.

Next, the information processing device 100 sends, to the first transporter 11, a locking command commanding locking of the storage locker of the first transporter 11. When the data communication circuit of the first transporter 11 receives the locking command, the CPU of the first transporter 11 outputs, to the drive circuit, a control signal for locking the storage locker of the first transporter 11.

Thereafter, the information processing device 100 sends, to the first transporter 11, an execution command that includes the information expressing the address of the destination of the sold article, and that commands the execution of the transport to locker device procedure.

When the data communication circuit of the first transporter 11 receives the execution command, the CPU of the first transporter 11 executes non-illustrated transport to locker device processing.

When the transport to locker device processing starts, the CPU of the first transporter 11 acquires the execution command from the data communication circuit, and acquires the information expressing the address of the destination from the acquired execution command. Next, the CPU of the first transporter 11 acquires information expressing the latitude, longitude, and altitude that is associated in advance with the information expressing the address of the destination and that is stored in advance in the flash memory.

Next, the CPU of the first transporter 11 executes the same processing as steps S02 to S04 of FIG. 4 using the acquired information to transport the article to the destination of the article. Then, the CPU of the first transporter 11 outputs, to the data communication circuit 219e with the information processing device 100 as the destination, a completion report that includes the procedure ID of the transport to locker device procedure and that informs that the transport to locker device procedure is completed, and ends the execution of the transport to locker device processing.

Thus, in the present embodiment, the first transporter 11 performs the entire transport to locker device procedure and, as such, a human is not involved in the transport to locker device procedure. As such, the information processing device 100 does not update the first time, even when a completion report is received that informs that the transport to locker device procedure is completed.

The locker device 12 is a delivery box that is installed at the entrance of the apartment building where the recipient resides. The locker device 12 includes a plurality of non-illustrated storage boxes, and a control device that controls locking and unlocking of each of the plurality of storage boxes. The configurations and functions of the plurality of storage boxes and the control device of locker device 12 are the same as the configurations and functions of the plurality of storage boxes 225 and the control device 229 of the depository 22.

Each of the plurality of storage boxes of the locker device 12 includes a box body, a door, a door frame, a deadbolt, and a strike plate that are non-illustrated. The configurations and functions of the box body, the door, the door frame, the deadbolt, and the strike plate of the locker device 12 are the same as the configurations and functions of the box body, the door, the door frame, the deadbolt, and the strike plate that are non-illustrated of each of the plurality of storage boxes 225 of the depository 22.

The control device of the locker device 12 includes, as hardware, a CPU, a RAM, a ROM, a flash memory, a data communication circuit, a video card, a display device, an input device, an input/output port, and a drive circuit that are non-illustrated. The configurations and functions of the hardware of the control device of the locker device 12 are the same as the configurations and functions of the hardware of the control device 229 of the depository 22. In the present embodiment, the locker device 12 includes one CPU, but may include a plurality of CPUs. Additionally, the locker device 12 may include a plurality of RAMs and flash memories.

When the completion report informing that the transport to locker device procedure is completed is received from the first transporter 11 that transports the article to the locker device 12, the information processing device 100 sends, to the first transporter 11, an execution command commanding the execution of the store in locker device procedure.

When the data communication circuit of the first transporter 11 receives the execution command, the CPU of the first transporter 11 executes non-illustrated store in locker device processing to perform the store in locker device procedure in accordance with the execution command.

When the execution of the store in locker device processing starts, the CPU of the first transporter 11 executes the same processing as steps S21 to S24 of FIG. 7. As a result, the first transporter 11 uses the robot arm to retrieve the article from the storage locker of the first transporter 11 and store the retrieved article in one of the plurality of storage boxes of the locker device 12, thereby moving the article from the first transporter 11 to the locker device 12.

Thereafter, the CPU of the first transporter 11 generates a completion report that includes the box ID identifying the storage box of the locker device 12 in which the article is stored and the procedure ID of the store in locker device procedure, and that informs that the store in locker device procedure is completed. Next, the CPU of the first transporter 11 outputs the generated completion report to the data communication circuit with the information processing device 100 as the destination. After the data communication circuit sends the completion report to the information processing device 100, the CPU of the first transporter 11 ends the execution of the store in locker device processing. Then, the CPU of the first transporter 11 outputs a control signal for traveling back on the movement route, thereby returning to the undertaking location.

Thus, in the present embodiment, the first transporter 11 performs the entire store in locker device procedure and, as such, a human is not involved in the store in locker device procedure. As such, the information processing device 100 does not update the first time, even when a completion report is received that informs that the store in locker device procedure is completed.

Next, the information processing device 100 calculates, as the recommended receiving start time at which receiving is recommended to start, a time that is a target amount of elapsed time later than the first time. Then, the information processing device 100 sends, to the terminal device 19 of the recipient, a notification informing of the first time, the recommended receiving start time, the box ID, and the password to execute the notification procedure.

In the present embodiment, the target amount of elapsed time is set in advance to the amount of time from when a predetermined virus or bacterium is discharged from a human and adheres to the article to when the magnitude of the infectivity of that predetermined virus or bacterium is less than or equal to a predetermined magnitude. In the present embodiment, the phrase "the infectivity of a virus or bacterium adhered to the article" refers to the ability of the virus or bacterium to infect, and the ability of the virus or bacterium to infect is expressed in terms of infection probability of a human that physically touches the virus or bacterium to become infected with the virus or bacterium. However, the present embodiment is not limited thereto. Additionally, in the present embodiment, the phrase "a human that physically touches the virus or bacterium to become infected with the virus or bacterium" means that the virus or bacterium parasitizes and propagates in or on the surface of the human body, but is not limited thereto.

When the data communication circuit 194a of the terminal device 19 receives the notification, the CPU 191 acquires the notification from the data communication circuit 194a and displays the acquired notification on the display device 195b. The recipient that views the display moves so as to arrive at the locker device 12 at the recommended receiving start time or later, and performs an operation for inputting the box ID and the password on the input device of the locker device 12.

When the input device of the locker device 12 outputs a signal corresponding to that operation, the CPU of the locker device 12 acquires, on the basis of that signal, the box ID and information expressing the password. Next, the CPU of the locker device 12 generates an inquiry that includes the acquired box ID and information expressing the password, and that inquires whether or not unlocking of the storage box identified by the box ID is allowed. Then, the CPU of the locker device 12 outputs the generated inquiry to the data communication circuit of the locker device 12 with the information processing device 100 as the destination.

When the information processing device 100 receives the inquiry, the information processing device 100 determines whether or not the combination of the box ID and the password included in that inquiry matches the combination of the box ID and the password sent to the terminal device 19. When the information processing device 100 determines that these combinations match, the information processing device 100 returns a response that unlocking is allowed and, when the information processing device 100 determines that these combinations do not match, the information processing device 100 returns a response that unlocking is not allowed.

When the data communication circuit of the locker device 12 receives the response, the CPU of the locker device 12 acquires the received response from the data communication circuit. Next, when the acquired response is a response that unlocking is not allowed, the CPU causes the display device to display a message informing that at least one of the box ID and the password is incorrect. The recipient that views the display performs the operation for inputting the box ID and the password again.

In contrast, when the acquired response is a response that unlocking is allowed, the CPU of the locker device 12 outputs, to the drive circuit, a control signal for unlocking the storage box identified by the acquired box ID. The recipient opens the door of the unlocked storage box and receives the purchased article.

The information processing device 100 is implemented as a server device, and is installed at the warehouse or office of the distributor that sells the article. The information processing device 100 carries out control for causing the first distribution mechanism 10 and the second distribution mechanism 20 to execute the first to the ninth procedures.

Figure 11:
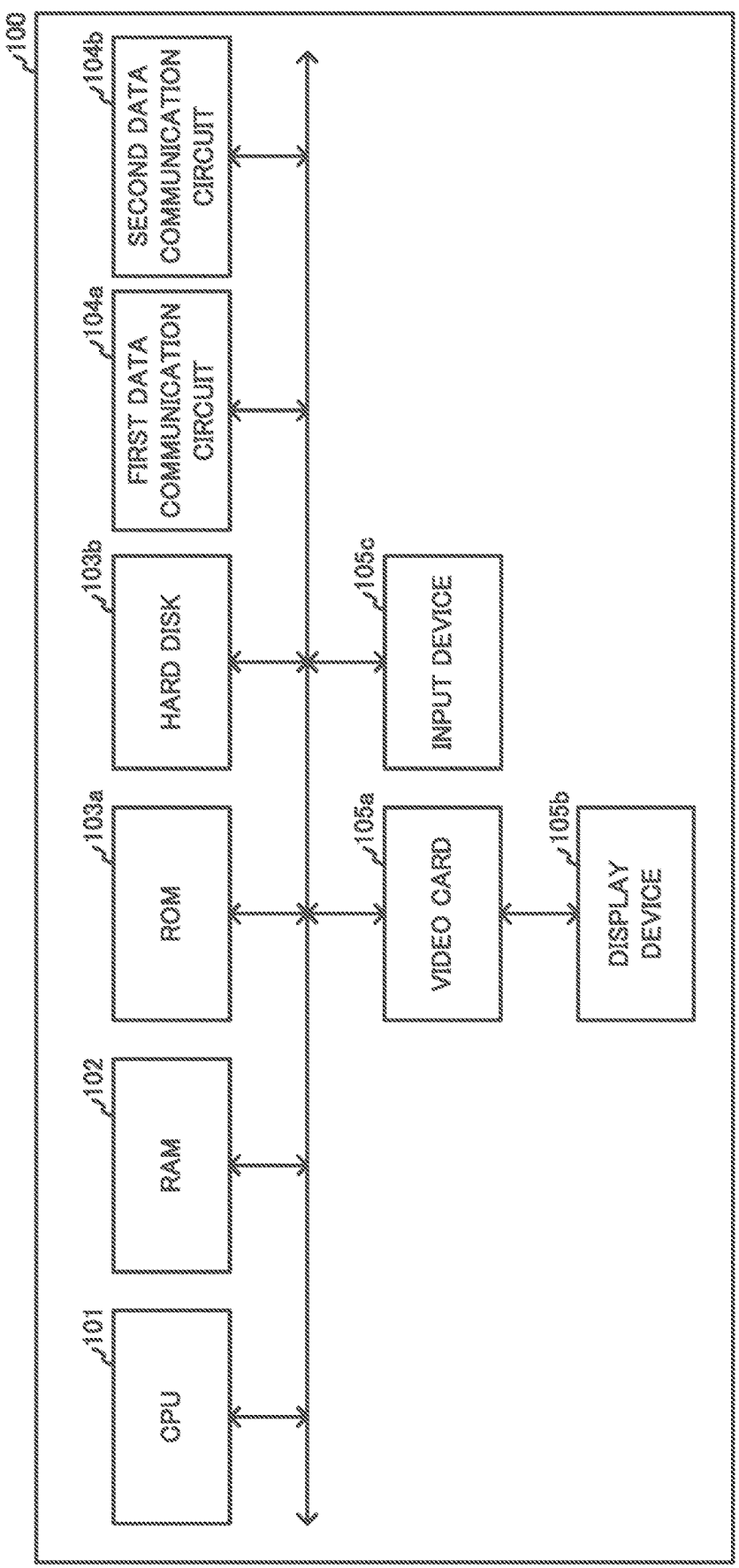
FIG. 11 is a hardware configuration drawing illustrating a configuration example of an information processing device.

As illustrated in FIG. 11, the information processing device 100 includes a CPU 101, a RAM 102, a ROM 103a, a hard disk 103b, a first data communication circuit 104a, a second data communication circuit 104b, a video card 105a, a display device 105b, and an input device 105c. The configurations and functions of the CPU 101, the RAM 102, the ROM 103a, the video card 105a, the display device 105b, and the input device 105c of the information processing device 100 are the same as the configurations and functions of the CPU 219a, the RAM 219b, the ROM 219c, the video card 219f, the display device 219g, and the input device 219h of the second transporter 21 illustrated in FIG. 3.

The hard disk 103b of the information processing device 100 stores various types of data and tables in which data is stored that are used in the execution of the programs. The information processing device 100 may include a flash memory instead of the hard disk 103b.

In one example, the first data communication circuit 104a of the information processing device 100 is implemented as an NIC and carries out, in accordance with a communication standard such as long term evolution (LTE) or 5th Generation (5G), data communication using radio waves with a non-illustrated base station that is connected to the internet IN. Thus, the first data communication circuit 104a of the information processing device 100 carries out data communication with the first transporter 11 and the locker device 12 of the first distribution mechanism 10, and the terminal device 19 that are connected to the internet IN.

In one example, the second data communication circuit 104b of the information processing device 100 is implemented as an NIC and, in accordance with a communication standard such as TCP/IP, carries out data communication using radio waves with a non-illustrated access point that is connected to the local area network LN. Thus, the second data communication circuit 104b of the information processing device 100 carries out data communication with the second transporter 21 and the depository 22 of the second distribution mechanism 20 that are connected to the local area network LN.

Figure 12:
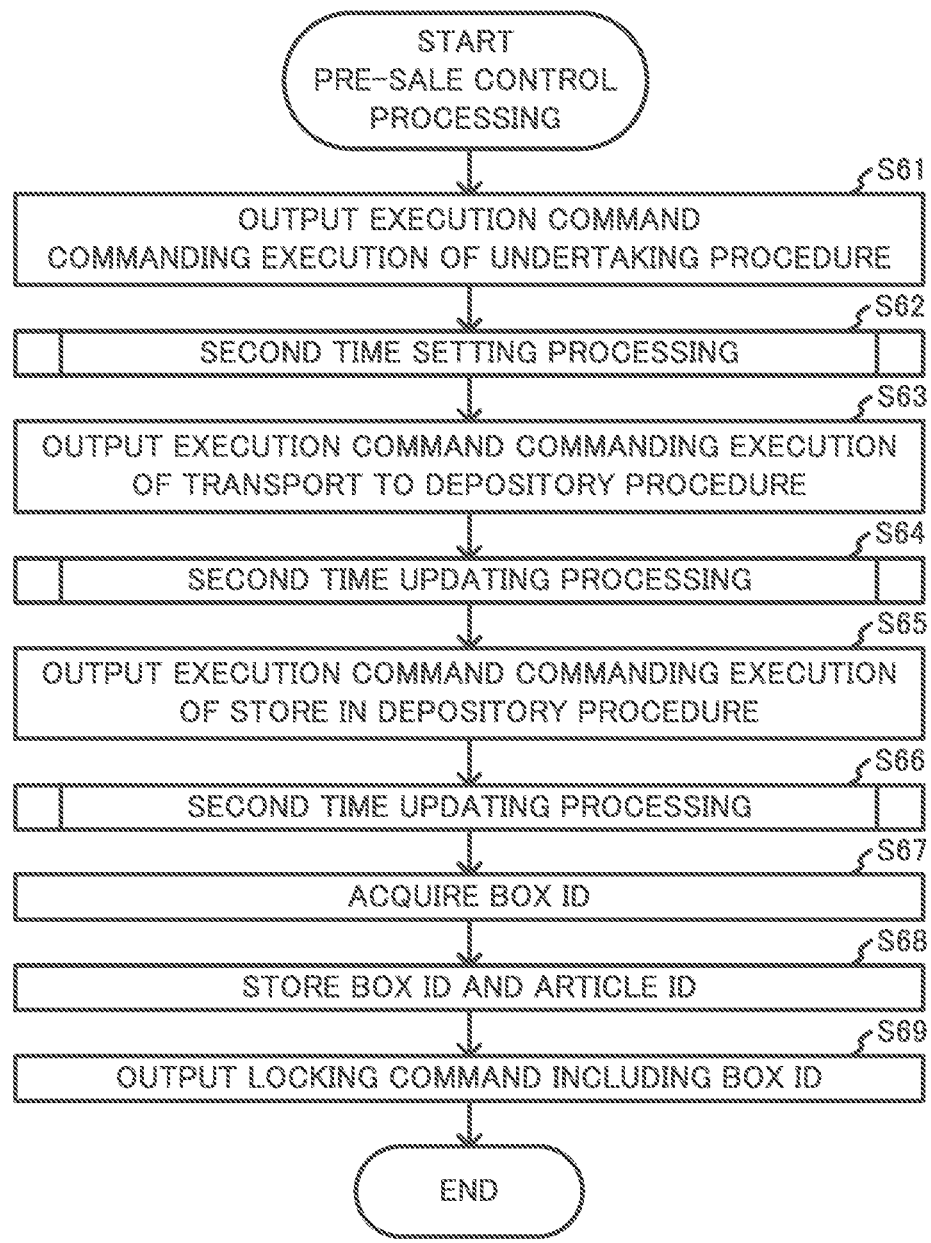
FIG. 12 is a flowchart illustrating an example of pre-sale control processing executed by the information processing device.

When the first data communication circuit 104a of the information processing device 100 receives a notification informing that the carrier has arrived at the office, the CPU 101 of the information processing device 100 executes pre-sale control processing such as illustrated in FIG. 12 for performing control for causing the second distribution mechanism 20 to execute the pre-sale procedures, which are performed on articles prior to being sold.

Figure 13:
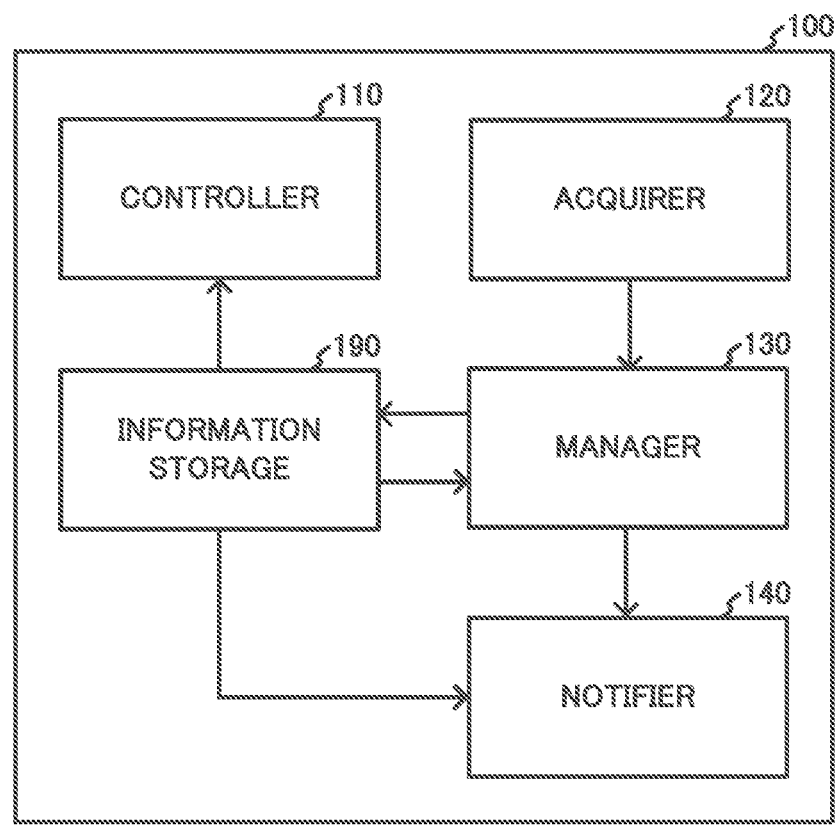
FIG. 13 is a functional block diagram illustrating an example of the functions of the information processing device according to Embodiment 1.

As a result, the CPU 101 of the information processing device 100 functions as a controller 110 such as illustrated in FIG. 13 that performs control for causing the first distribution mechanism 10 and the second distribution mechanism 20 to execute delivery procedures. Additionally, the CPU 101 functions as an acquirer 120 that acquires the procedure IDs identifying the procedures executed by the first distribution mechanism 10 and the second distribution mechanism 20.

Furthermore, the CPU 101 of the information processing device 100 functions as a manager 130 that manages the first time that is a time prior to the receiving time at which the recipient receives the article, and that is the last time at which a human contacts the article on which the delivery procedures of the article are performed. The manager 130 also manages the second time that is a time before the hand over time at which the article is handed over from the second distribution mechanism 20 to the first distribution mechanism 10, and that is the last time at which a human contacted the article.

In the present embodiment, the management of the times including the first time and the second time includes, for example, storing information expressing a time in volatile memory, namely the RAM 102 of the information processing device 100, or in non-volatile memory, namely the hard disk 103b of the information processing device 100, and reading the stored information expressing the time.

The hard disk 103b of the information processing device 100 functions as an information storage 190 in which various tables are stored in advance. Data used in the execution of the pre-sale control processing is stored in these various tables.

A procedure table such as illustrated in FIG. 14 is stored in advance in the information storage 190 of the information processing device 100. Information related to the delivery procedures is stored in advance in the procedure table. A plurality of records is stored in advance in the procedure table. A procedure ID identifying a procedure, information expressing the name of that procedure, and an involvement flag expressing whether or not a human is involved in that procedure are associated and stored in advance in each record of the procedure table.

In the present embodiment, information related to the undertaking procedure in which the article is undertaken from the carrier is stored in the first record of the procedure table. As such, the procedure ID "P1" identifying the undertaking procedure, information expressing the name "undertaking procedure", and an involvement flag having a value of "TRUE" expressing that a human is involved in the undertaking procedure are associated and stored in advance in the first record. In the present embodiment, a human is involved in the undertaking procedure because the worker of the carrier stores the article in the second transporter 21 by hand.

Additionally, the procedure ID "P2" and information expressing the name of the transport to depository procedure, and an involvement flag having a value of "FALSE" expressing that a human is not involved in the transport to depository procedure are associated and stored in advance in the second record of the procedure table. In the present embodiment, a human is not involved in the transport to depository procedure because the second transporter 21 that transports the article moves to the depository 22 by traveling unmanned and autonomously on the ground.

The procedure ID "P3" and information expressing the name of the store in depository procedure, and an involvement flag having a value of "FALSE" expressing that a human is not involved in the store in depository procedure are associated and stored in advance in the third record of the procedure table. In the present embodiment, a human is not involved in the store in depository procedure because the second transporter 21 uses the robot arm 218 to store the article in the depository 22.

The procedure ID "P4" and information expressing the name of the retrieval procedure whereby the sold article is retrieved from the depository 22, and an involvement flag having a value of "FALSE" expressing that a human is not involved in the retrieval procedure are associated and stored in advance in the fourth record of the procedure table. In the present embodiment, a human is not involved in the retrieval procedure because the second transporter 21 uses the robot arm 218 to retrieve the article from the depository 22.

The procedure ID "P5" and information expressing the name of the transport to first transporter procedure, and an involvement flag having a value of "FALSE" expressing that a human is not involved in the transport to first transporter procedure are associated and stored in advance in the fifth record of the procedure table.

The procedure ID "P6" and information expressing the name of the hand over procedure whereby the retrieved article is handed over from the second distribution mechanism 20 to the first distribution mechanism 10, and an involvement flag having a value of "FALSE" expressing that a human is not involved in the hand over procedure are associated and stored in advance in the sixth record of the procedure table. In the present embodiment, a human is not involved in the hand over procedure because the second transporter 21 of the second distribution mechanism 20 uses the robot arm 218 to hand over the article to the first transporter 11 of the first distribution mechanism 10.

The procedure ID "P7" and information expressing the name of the transport to locker device procedure, and an involvement flag having a value of "FALSE" expressing that a human is not involved in the transport to locker device procedure are associated and stored in advance in the seventh record of the procedure table. In the present embodiment, a human is not involved in the transport to locker device procedure because the first transporter 11 that transports the article moves to the locker device 12 by traveling unmanned and autonomously on the ground.

The procedure ID "P8" and information expressing the name of the store in locker device procedure, and an involvement flag having a value of "FALSE" expressing that a human is not involved in the store in locker device procedure are associated and stored in advance in the eighth record of the procedure table. In the present embodiment, a human is not involved in the store in locker device procedure because the first transporter 11 uses the non-illustrated robot arm to store the article in the locker device 12.

The procedure ID "P9" and information expressing the name of the notification procedure, and an involvement flag having a value of "FALSE" expressing that a human is not involved in the notification procedure are associated and stored in advance in the ninth record of the procedure table.

A second time table such as illustrated in FIG. 15 is stored in advance in the information storage 190 of the information processing device 100. Information related to the second time is stored in the second time table. One or a plurality of an article ID of an article and information expressing the second time of that article are associated and stored in the second time table.

Additionally, a depository table such as illustrated in FIG. 16 is stored in advance in the information storage 190 of the information processing device 100. Information related to articles stored in the depository 22 is stored in the depository table. A box ID identifying a storage box 225 of the depository 22 and the article ID of the article stored in that storage box 225 are associated and stored in the depository table.

When the execution of the pre-sale control processing of FIG. 12 starts, the controller 110 of the information processing device 100 outputs, to the second data communication circuit 104b with the second transporter 21 as the destination, an execution command commanding the execution of the undertaking procedure in which an article is undertaken from the carrier (step S61). The second data communication circuit 104b of the information processing device 100 sends the execution command to the second transporter 21 that is connected to the second data communication circuit 104b via the local area network LN.

Figure 17:
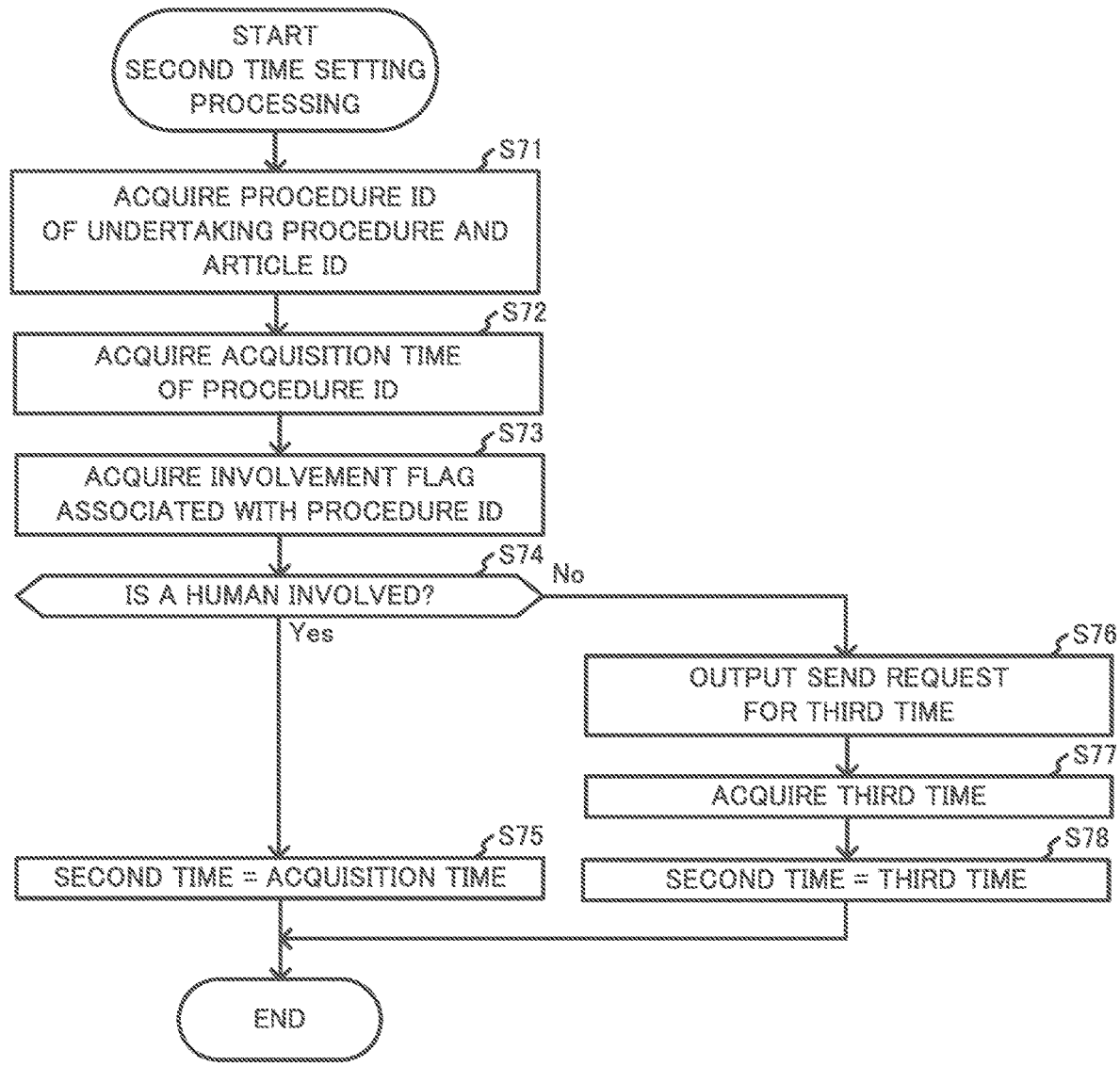
FIG. 17 is a flowchart illustrating an example of second time setting processing executed by the information processing device.

Thereafter, when the second data communication circuit 104b of the information processing device 100 receives, from the second transporter 21 that executes the undertaking procedure in accordance with the execution command, a completion report informing that the undertaking procedure is completed, second time setting processing such as illustrated in FIG. 17 for setting the second time is executed (step S62).

When the execution of the second time setting processing starts, the acquirer 120 of the information processing device 100 acquires the completion report from the second data communication circuit 104b, and acquires, from the completion report, the procedure ID "P1" of the undertaking procedure and the article ID of the article undertaken due to the execution of the undertaking procedure (step S71). Next, the acquirer 120 acquires, as the time at which the undertaking of the article is performed, an acquisition time at which the procedure ID "P1" is acquired. To realize this, the acquirer 120 acquires, as the acquisition time of the procedure ID "P1", a system time managed by an operating system (OS), for example (step S72). The acquisition time is acquired in this manner because, in the present embodiment, the "time at which the undertaking of the article is performed" means the time at which the undertaking procedure is completed. Additionally, in the present embodiment, a length of time, from the time at which the execution of the undertaking procedure is completed to the acquisition time at which the information processing device 100 receives the completion report of the undertaking procedure and acquires the procedure ID "P1" of the undertaking procedure from the completion report, is a predetermined length such as, for example, "1" minute or shorter and, as such, the time at which the undertaking of the article is performed can be equated with the acquisition time at which the procedure ID "P1" of the undertaking procedure is acquired.

Next, the acquirer 120 of the information processing device 100 acquires, from the procedure table of FIG. 14, the involvement flag associated with the procedure ID "P1" of the undertaking procedure (step S73), and the manager 130 determines that the value of the acquired involvement flag is the value "TRUE" expressing that a person is involved in the undertaking procedure (step S74; Yes).

Thereafter, the manager 130 of the information processing device 100 initializes the second time to the acquisition time (step S75). Then, the manager 130 associates and stores, in the second time table of FIG. 15, the article ID acquired in step S71 and the second time initialized using the acquisition time to manage, as the second time, the acquisition time acquired as the time at which the undertaking of the article is performed. Then, the manager 130 ends the execution of the second time setting processing.

After the second time setting processing is executed in step S62 of FIG. 12, the controller 110 of the information processing device 100 outputs, to the second data communication circuit 104b with the second transporter 21 as the destination, an execution command commanding the execution of the transport to depository procedure (step S63).

Thereafter, when the information processing device 100 receives the completion report, the information processing device 100 executes second time updating processing such as illustrated in FIG. 18 for updating the second time, with the article ID acquired in step S71 of FIG. 17 as an argument (step S64).

When the execution of the second time update processing starts, the acquirer 120 of the information processing device 100 acquires, from the argument, the article ID of the article on which the transport to depository procedure is performed. Additionally, the acquirer 120 acquires, from the second data communication circuit 104b, the completion report sent from the second transporter 21, and acquires the procedure ID "P2" of the transport to depository procedure from the completion report (step S81). Next, the acquirer 120 acquires the acquisition time of the procedure ID "P2" as the time at which the transportation to the depository 22 is performed. To realize this, the acquirer 120 acquires the system time managed by the OS, for example, as the acquisition time of the procedure ID "P2" (step S82). The acquisition time is acquired in this manner because, in the present embodiment, the "time at which the transportation to the depository 22 is performed" means the time at which the transport to depository procedure is completed, and the time at which the transport to depository procedure is completed can be equated with the acquisition time at which the procedure ID "P2" of the transport to depository procedure is acquired from the completion report.

Next, the acquirer 120 of the information processing device 100 acquires, from the procedure table of FIG. 14, the involvement flag associated with the procedure ID "P2" of the transport to depository procedure (step S83). Then, the manager 130 determines that the value of the acquired involvement flag is the value "FALSE" expressing that a person is not involved in the transport to depository procedure (step S84; No), and ends the execution of the second time updating processing without updating the second time.

After the execution of the second time updating processing in step S64 of FIG. 12, the controller 110 of the information processing device 100 outputs, to the second data communication circuit 104b with the second transporter 21 as the destination, an execution command commanding the execution of the store in depository procedure (step S65).

Thereafter, when the information processing device 100 receives the completion report, the information processing device 100 executes second time updating processing (step S66). As a result, the manager 130 of the information processing device 100 determines that the value of the involvement flag associated with the procedure ID "P3" of the store in depository procedure is the value "FALSE" expressing that a person is not involved, and maintains the second time without updating the second time.

Next, the acquirer 120 of the information processing device 100 acquires, from the completion report received by the second data communication circuit 104b, the box ID identifying the storage box 225 of the depository 22 in which the article is stored by the store in depository procedure (step S67). Next, the manager 130 associates and stores, in the depository table of FIG. 16, the acquired box ID, and the article ID of the article stored in the storage box 225 identified by that box ID (step S68).

Thereafter, the controller 110 of the information processing device 100 outputs, to the second data communication circuit 104b with the depository 22 as the destination, a locking command that includes the box ID acquired in step S67 and that commands locking of the storage box 225 identified by that box ID (step S69), and ends the execution of the pre-sale control processing.

Figure 19A:
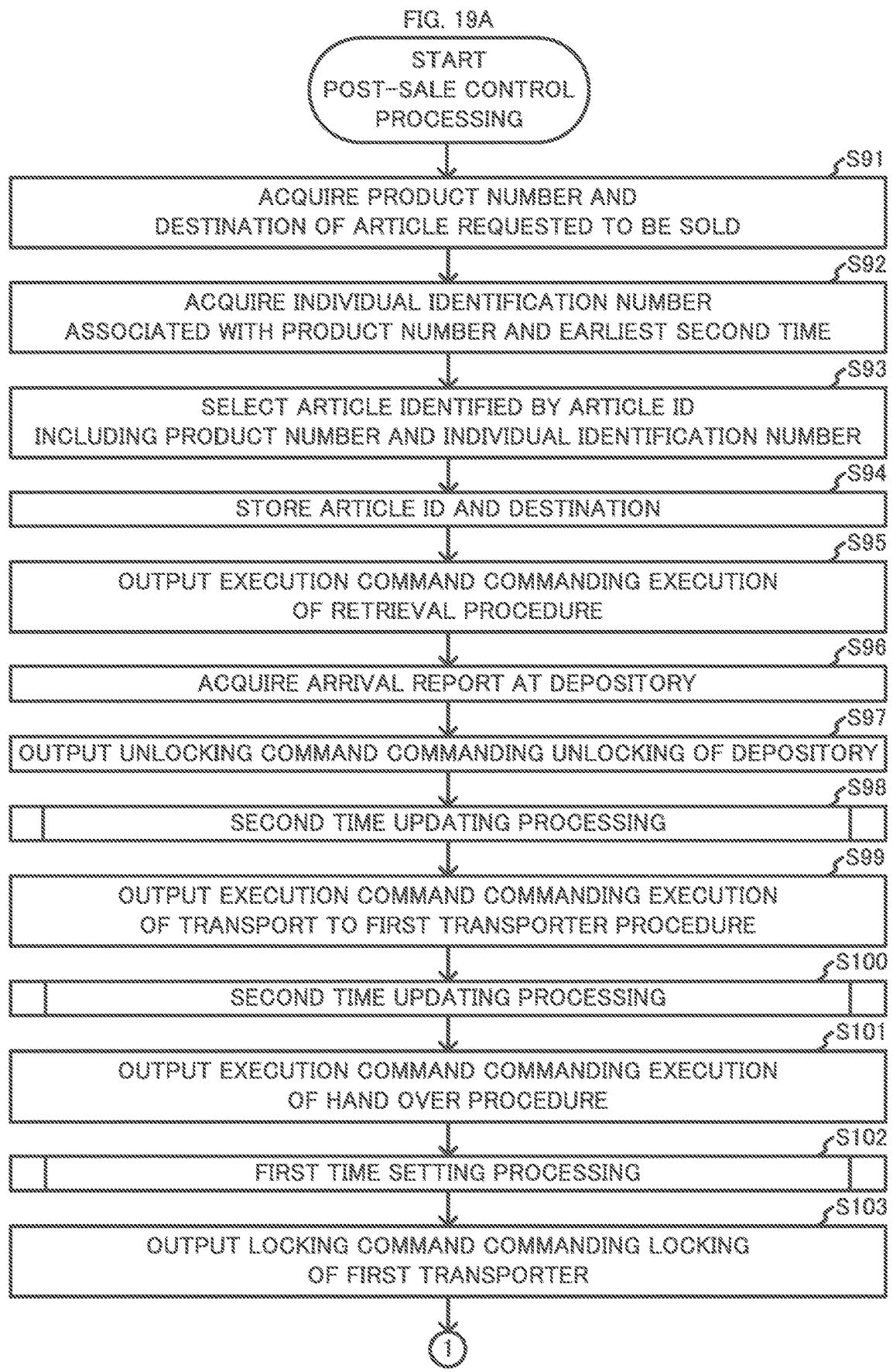
FIGS. 19A and 19B are each flowcharts illustrating an example of post-sale control processing executed by the information processing device according to Embodiment 1.
Figure 19B:
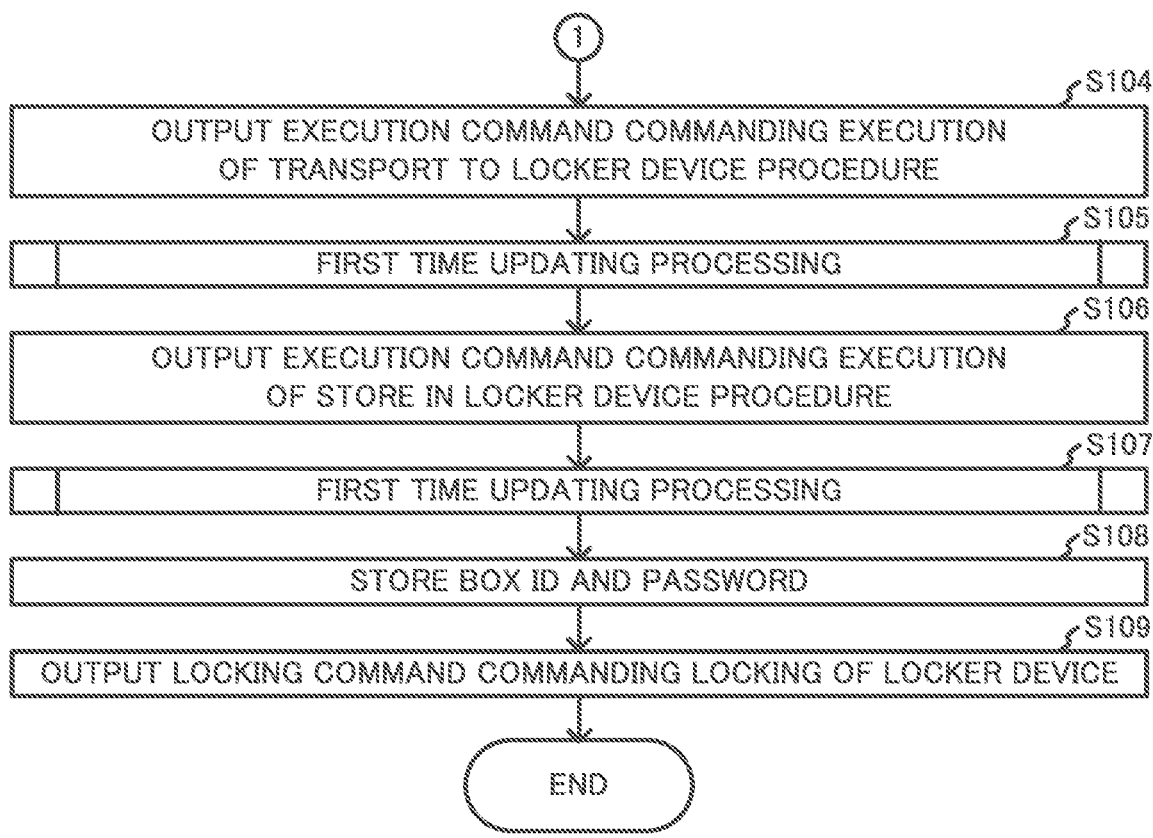

When the first data communication circuit 104a of the information processing device 100 receives, from the terminal device 19, the sale request that includes the product number and the information expressing the address of the destination, the CPU 101 of the information processing device 100 executes post-sale control processing such as illustrated in FIGS. 19A and 19B in which control is performed for causing the first distribution mechanism 10 and the second distribution mechanism 20 to execute the post-sale procedures.

An article table such as illustrated in FIG. 20 is stored in advance in the information storage 190 of the information processing device 100. Information related to the sold article is stored in the article table. The article ID of a sold article, the information expressing the destination of that article, the first time, the box ID identifying the storage box of the locker device 12 in which the article is stored, and information expressing a password used to authenticate the recipient of that article are associated and stored in the article table.

When the execution of the post-sale control processing of FIGS. 19A and 19B starts, the acquirer 120 of the information processing device 100 acquires the sale request from the first data communication circuit 104a, and acquires the product number and the information expressing the destination of the article requested to be sold (step S91). Next, the acquirer 120 acquires the earliest second time from among the one or plurality of second times associated with the acquired product number in the second time table of FIG. 15. Then, the acquirer 120 acquires the individual identification number associated with the acquired product number and the acquired earliest second time (step S92).

Next, the controller 110 of the information processing device 100 generates an article ID including the acquired product number and the individual identification number, and selects the article identified by the generated article ID as the article to be sold in response to the sale request (step S93). The article identified by the product number included in the sale request and the individual identification number associated with the earliest second time is selected as the article to be sold in order to sell the article for which the most time has elapsed since being touched by a human.

Next, the manager 130 of the information processing device 100 stores, in the article table of FIG. 20, the generated article ID, and the information expressing the destination of the article identified by that article ID (step S94).

Thereafter, the acquirer 120 of the information processing device 100 acquires, from the depository table of FIG. 16, the box ID associated with the article ID of the sold article. Then, the controller 110 generates an execution command that includes the acquired box ID and that commands the execution of the retrieval procedure in which the article stored in the storage box 225 of the depository 22 identified by that box ID is retrieved. Next, the controller 110 outputs the generated execution command to the second data communication circuit 104b with the second transporter 21 as the destination (step S95).

When the second data communication circuit 104b of the information processing device 100 receives an arrival report informing that the second transporter 21 has arrived at the depository 22 to retrieve the article (step S96), the controller 110 of the information processing device 100 generates an unlocking command commanding unlocking of the storage box 225 in which the sold article is stored. Next, the controller 110 adds the box ID of the storage box 225 in which the sold article is stored to the generated unlocking command and, then, outputs the unlocking command to the second data communication circuit 104b with the depository 22 as the destination (step S97).

Thereafter, when the information processing device 100 receives the completion report informing that the retrieval procedure is completed, the information processing device 100 executes the second time updating processing illustrated in FIG. 18 (step S98). As a result, the manager 130 of the information processing device 100 determines that the value of the involvement flag associated with the procedure ID "P4" of the retrieval procedure is the value "FALSE" expressing that a person is not involved, and maintains the second time without updating the second time.

Next, the controller 110 of the information processing device 100 outputs, to the second data communication circuit 104b with the second transporter 21 as the destination, an execution command commanding the execution of the transport to first transporter procedure (step S99). Then, when the information processing device 100 receives the completion report, the information processing device 100 executes the second time updating processing illustrated in FIG. 18 (step S100). At this time, the manager 130 determines that the value of the involvement flag associated with the procedure ID "P5" of the transport to first transporter procedure is "FALSE", and does not update the second time.

Next, the controller 110 of the information processing device 100 outputs, to the second data communication circuit 104b with the second transporter 21 as the destination, an execution command commanding the execution of the hand over procedure in which the article is handed over from the second transporter 21 to the first transporter 11 (step S101).

Figure 21:
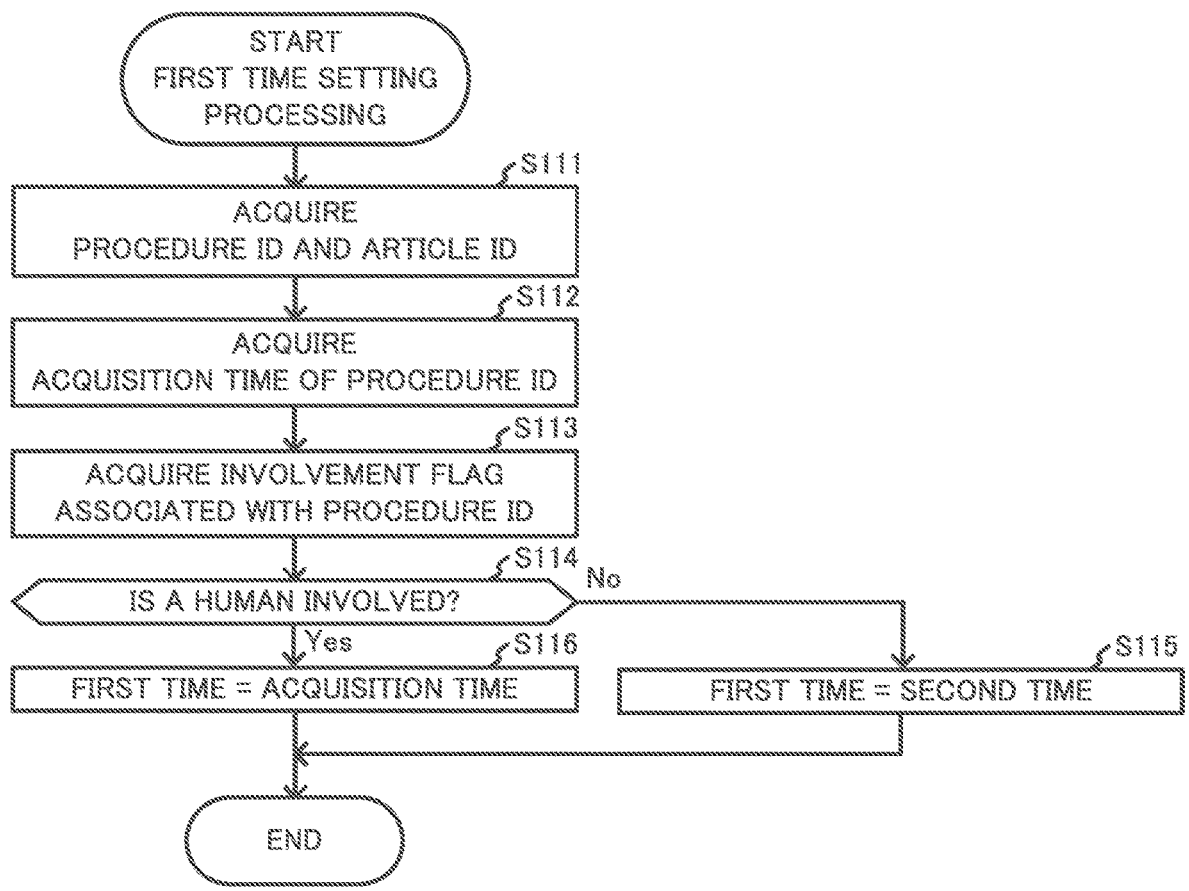
FIG. 21 is a flowchart illustrating an example of first time setting processing executed by the information processing device.

Thereafter, when the information processing device 100 receives the completion report, the information processing device 100 executes first time setting processing such as illustrated in FIG. 21 in which setting of the first time is performed, with the article ID generated in step S93 of FIG. 19A as an argument (step S102).

When the execution of the first time setting processing starts, the acquirer 120 of the information processing device 100 acquires, from the argument, the article ID of the article on which the hand over procedure is performed. Additionally, the acquirer 120 acquires, from the second data communication circuit 104b, the completion report sent from the second transporter 21, and acquires the procedure ID "P6" of the hand over procedure from the completion report (step S111). Next, the acquirer 120 acquires, as the time at which the handing over of the article is performed, the acquisition time at which the procedure ID "P6" is acquired (step S112).

Next, the acquirer 120 of the information processing device 100 acquires, from the procedure table of FIG. 14, the involvement flag associated with the procedure ID "P6" of the hand over procedure (step S113). Then, the manager 130 determines that the value of the acquired involvement flag is "FALSE" (step S114; No), and initializes the first time to the second time that is the time that a human last contacted the article prior to the hand over being performed (step S115). Then, the manager 130 searches the article table of FIG. 20 for a record in which the acquired article ID is stored, and associates the first time initialized using the second time with that article ID and stores the associated information in the found record to manage the second time as the first time. Then, the manager 130 ends the execution of the first time setting processing.

Thereafter, the controller 110 of the information processing device 100 outputs, to the first data communication circuit 104a with the first transporter 11 as the destination, a locking command commanding locking of the storage locker of the first transporter 11 (step S103).

Next, the controller 110 of the information processing device 100 outputs, to the first data communication circuit 104a with the first transporter 11 as the destination, an execution command commanding the execution of the transport to locker device procedure (step S104).

Figure 22:
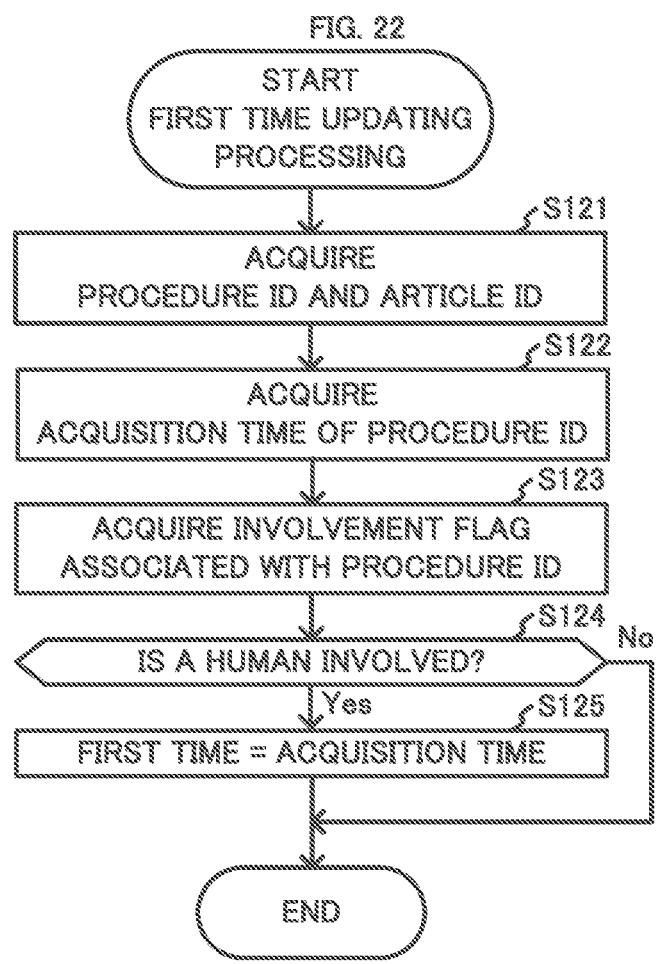
FIG. 22 is a flowchart illustrating an example of first time updating processing executed by the information processing device.

Thereafter, when the information processing device 100 receives the completion report, the information processing device 100 executes first time updating processing such as illustrated in FIG. 22 for updating the first time, with the article ID as an argument (step S105).

When the execution of the first time updating processing starts, the acquirer 120 of the information processing device 100 acquires, from the argument, the article ID of the article on which the transport to locker device procedure is performed. Additionally, the acquirer 120 acquires, from the first data communication circuit 104a, the completion report sent from the first transporter 11, and acquires the procedure ID "P7" of the transport to locker device procedure from the completion report (step S121). Next, the acquirer 120 acquires, as the time at which the transportation to the locker device 12 is performed, the acquisition time at which the procedure ID "P7" is acquired (step S122).

Next, the acquirer 120 of the information processing device 100 acquires, from the procedure table of FIG. 14, the involvement flag associated with the procedure ID "P7" of the transport to locker device procedure (step S123). Then, the manager 130 determines that the value of the acquired involvement flag is "FALSE" (step S124; No), and ends the execution of the first time updating processing without updating the first time.

After the execution of the first time updating processing in step S105 of FIG. 19B, the controller 110 of the information processing device 100 outputs, to the first data communication circuit 104a with the first transporter 11 as the destination, an execution command commanding the execution of the store in locker device procedure (step S106).

Thereafter, when the information processing device 100 receives the completion report, the information processing device 100 executes first time updating processing (step S107). As a result, the acquirer 120 of the information processing device 100 acquires, from the completion report sent from the first transporter 11, the procedure ID "P8" of the store in locker device procedure. Additionally, the manager 130 determines that the value of the involvement flag associated with the procedure ID "P8" is "FALSE", and maintains the first time without updating the first time.

Thereafter, the acquirer 120 of the information processing device 100 acquires, from the completion report sent from the first transporter 11, the box ID identifying the storage box of the locker device 12 in which the article is stored. Next, the controller 110 generates, on the basis of software random numbers or a predetermined rule for example, a password to be used in the authentication of the recipient of the article. Then, the manager 130 searches the article table of FIG. 20 for a record in which the article ID generated in step S93 is stored, associates the acquired box ID and information expressing the generated password with that article ID, and stores the associated information in the found record (step S108).

Next, the controller 110 of the information processing device 100 outputs, to the first data communication circuit 104a with the locker device 12 as the destination, a locking command that includes the acquired box ID and that commands locking of the storage box identified by that box ID (step S109), and ends the execution of the post-sale control processing.

Figure 23:
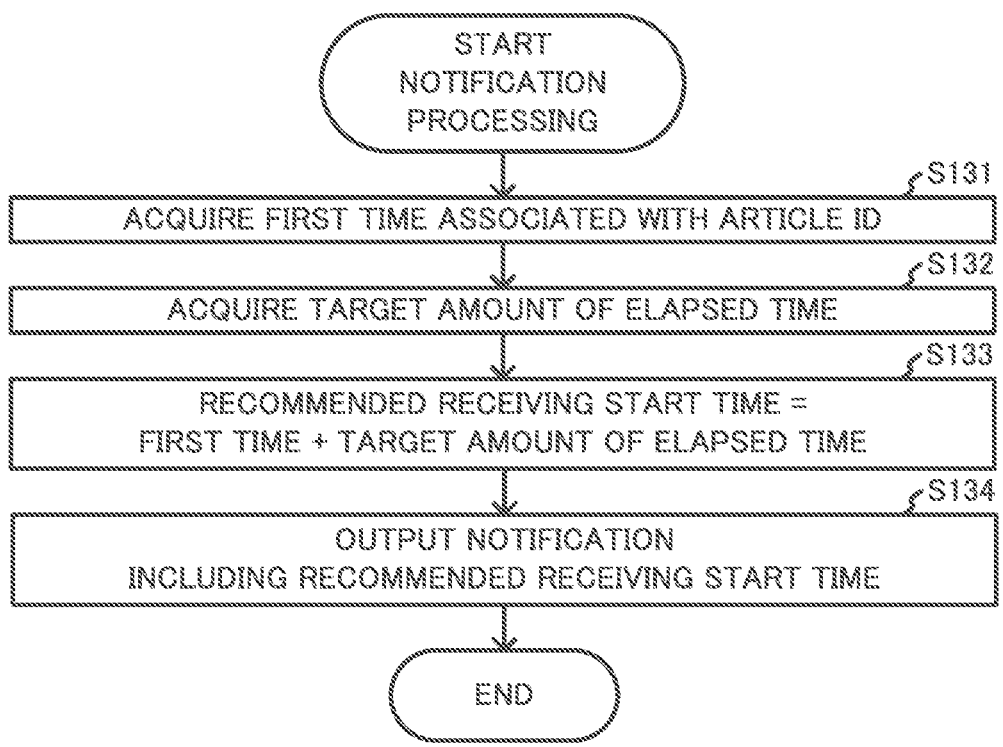
FIG. 23 is a flowchart illustrating an example of notification processing executed by the information processing device.

When the execution of the post-sale control processing is ended, the CPU 101 of the information processing device 100 executes notification processing such as illustrated in FIG. 23 with the article ID as an argument in order to execute a notification procedure in which a notification, informing that the article is delivered to the locker device 12 at the destination, is performed. As a result, the CPU 101 of the information processing device 100 functions as a notifier 140 such as illustrated in FIG. 13.

When the execution of the notification processing starts, the acquirer 120 of the information processing device 100 acquires, from the argument, the article ID of the article stored in the locker device 12. Next, the acquirer 120 acquires, from the article table of FIG. 20, the first time associated with the acquired article ID (step S131).

Thereafter, the acquirer 120 of the information processing device 100 acquires information expressing the target amount of elapsed time that is stored in advance in the information storage 190 (step S132). Next, the notifier 140 calculates, as the recommended receiving start time, a time obtained by adding the target amount of elapsed time expressed in the acquired information to the acquired first time (step S133). A configuration is possible in which the acquirer 120 further acquires information expressing a time margin stored in advance in the information storage 190, and the notifier 140 calculates, as the recommended receiving start time, a value obtained by adding the target amount of elapsed time and the time margin to the first time.

Thereafter, the acquirer 120 of the information processing device 100 acquires, from the article table of FIG. 20, the box ID and information expressing the password associated with the acquired article ID. Next, the notifier 140 generates a notification including the box ID and the password, the acquired first time, and the calculated recommended receiving start time. The generated notification includes a message informing that the article is delivered to the storage box identified by the box ID of the locker device 12 at the destination, the password is required to receive the article, and a human has not contacted the article later than the first time, and informing of the recommended receiving start time at which receiving is recommended to start. Then, the notifier 140 outputs the generated notification to the first data communication circuit 104a with the terminal device 19 carried by the recipient as the destination (step S134), and ends the execution of the notification processing.

When the first data communication circuit 104a of the information processing device 100 receives, from the locker device 12 that is operated by the recipient that views the notification, an inquiry inquiring whether or not unlocking of the locker device 12 is allowed, the CPU 101 of the information processing device 100 executes non-illustrated unlock permission processing.

When the execution of the unlock permission processing starts, the acquirer 120 of the information processing device 100 acquires the inquiry from the first data communication circuit 104a, and acquires the box ID and the information expressing the password from the acquired inquiry. Then, the acquirer 120 acquires, from the article table of FIG. 20, information expressing the password associated with the acquired box ID. Next, when the controller 110 determines that the password expressed in the information acquired from the inquiry and the password expressed in the information acquired from the article table match, the controller 110 outputs, to the first data communication circuit 104a with the locker device 12 as the destination, a response that unlocking is allowed. In contrast, when the controller 110 determines that these passwords do not match, the controller 110 outputs, to the first data communication circuit 104a with the locker device 12 as the destination, a rejection response that unlocking is not allowed. Then, the controller 110 ends the execution of the unlock permission processing.

According to these configurations, the distribution system 1 includes the first distribution mechanism 10 including the first transporter 11 that transports an article to the destination of the article, and the manager 130 that manages the first time that is a time earlier than the receiving time at which the article transported by the first transporter 11 is received and that is the last time at which a human contacted the article. As such, the distribution system 1 can manage the first time that is the last time at which a human touched the article prior to the article being received by the recipient.

According to these configurations, the distribution system 1 further includes the second distribution mechanism 20 that is a mechanism different than the first distribution mechanism 10 and that transports or stores the article. The manager 130 of the information processing device 100 further manages the second time that is a time earlier than the hand over time at which the second distribution mechanism 20 hands over the article to the first distribution mechanism 10 and that is the last time at which a human contacted the article that the second distribution mechanism 20 transports or stores. As such, the distribution system 1 can manage the second time that is the last time at which a human touched the article prior to the article being handed over to the first distribution mechanism 10.

According to these configurations, when a human is not involved in the hand over of the article to the first transporter 11, the manager 130 of the distribution system 1 manages, as the first time, the second time at which a human last contacted the article prior to the hand over being performed. That is, in a case in which a human is not involved in the hand over of the article from the second distribution mechanism 20 to the first distribution mechanism 10, the manager 130 manages the second time as the first time. As such, the distribution system 1 can manage, on the basis of the second time that is the last time at which a human contacted the article prior to the article being handed over to the first transporter 11 that transports the article, the first time that is the last time at which a human touched the article prior to the article being received by the recipient.

According to these configurations, the first distribution mechanism 10 further includes the locker device 12 that stores the article, and the first transporter 11 moves the article from the first transporter 11 to the locker device 12. As such, the distribution system 1 can move the article from the first transporter 11 to the locker device 12 without involving a person. Therefore, the distribution system 1 can maintain the first time at an earlier time compared to when a person is involved in the moving of the article from the first transporter 11 to the locker device 12. As such, even when a virus or bacterium is adhered to the article at the first time, the distribution system 1 can transport the article to the destination while further reducing the magnitude of infectivity of the virus or bacterium. Therefore, the distribution system 1 can suppress the recipient of the article from becoming infected with the virus or bacterium, even when the virus or bacterium is adhered to the article.

According to these configurations, the distribution system 1 further includes the notifier 140 that performs a notification to the recipient on the basis of the first time. The notification performed by the notifier 140 informs that a human has not contacted the article later than the first time. Due to these configurations, as long as the recipient receives the article on the basis of the notification after a sufficient amount of time has elapsed from the first time, even if a virus or bacterium is adhered to article due to contact with a human, it is possible to suppress the recipient of that article from being infected with that virus or bacterium.

According to these configurations, the target amount of elapsed time is the time from when the predetermined virus or bacterium is discharged from the body of a human to when the magnitude of infectivity of that virus or bacterium is less than or equal to a predetermined magnitude. Additionally, the notifier 140 of the information processing device 100 performs a notification for informing of the recommended receiving start time that is a time that is the target amount of elapsed time later than the first time, or a time later than that time. Here, the recommended receiving start time is a time at which receiving of the article is recommended to start. As such, as long as the recipient that views the notification receives the article at a time later than the recommended receiving start time, even if a virus or bacterium is adhered to the article due to contact with a human, it is possible to suppress the recipient of that article from being infected with that virus or bacterium.

Modified Example 1 of Embodiment 1

In Embodiment 1, a description is given in which a human is involved in the undertaking procedure in which the article is undertaken from the carrier. However, the present disclosure is not limited thereto. A human is not involved in the undertaking procedure according to the present modified example.

In the present modified example, the carrier transports the article using a non-illustrated third distribution mechanism including a non-illustrated third transporter that has the same configuration and functions as the configuration and functions of the second transporter 21 and that is an unmanned ground vehicle. The third distribution mechanism further includes a non-illustrated information processing device that manages a third time that is a time prior to the undertaking time at which the second transporter 21 undertakes the article from the third transporter and that is the last time that a human touched the article. The configuration and functions of the information processing device of the third distribution mechanism are the same as the configuration and functions of the information processing device 100.

When the third transporter of the carrier arrives at the undertaking location while storing the article, the second transporter 21 uses the robot arm 218 of the second transporter 21 to retrieve the article stored in the third transporter and, then, stores the article in the storage locker 214 of the second transporter 21, thereby executing the undertaking procedure.

The procedure ID "P1" and information expressing the name of the undertaking procedure, and a flag having a value of "FALSE" expressing that a human is not involved in the undertaking procedure are associated and stored in advance in the first record of the procedure table according to the present modified example.

When the execution of the pre-sale control processing illustrated in FIG. 12 is started using the procedure table according to the present modified example, the information processing device 100 executes the processing of step S61 (step S61). As a result, the information processing device 100 sends, to the second transporter 21 of the second distribution mechanism 20, an execution command commanding the execution of the undertaking procedure.

Thereafter, when the information processing device 100 receives, from the second transporter 21, a completion report informing of the completion of the execution of the undertaking procedure, the information processing device 100 executes the second time setting processing illustrated in FIG. 17 (step S62). When the execution of the second time setting processing starts, the information processing device 100 executes the processing of steps S71 to S74 (steps S71 to S74). As a result, the acquirer 120 of the information processing device 100 acquires the procedure ID "P1" of the undertaking procedure, and the manager 130 determines that the value of the involvement flag associated, in the procedure table according to the present modified example, with the procedure ID "P1" of the undertaking procedure is the value "FALSE" expressing that a person is not involved in the undertaking procedure (step S74; No).

Next, the manager 130 of the information processing device 100 outputs, to the first data communication circuit 104a with the information processing device of the third distribution mechanism as the destination, a send request requesting the sending of information expressing the third time (step S76).

Thereafter, when the first data communication circuit 104a of the information processing device 100 receives the information expressing the third time from the information processing device of the third distribution mechanism, the acquirer 120 of the information processing device 100 acquires the information expressing the third time from the first data communication circuit 104a (step S77).

Thereafter, the manager 130 of the information processing device 100 initializes the second time to the third time expressed in the acquired information (step S78). Next, the manager 130 associates the article ID acquired in step S71 and the second time initialized using the third time and stores the associated information in the second time table of FIG. 15 to manage the third time as the second time. Then, the manager 130 ends the execution of the second time setting processing.

After the execution of the second time setting processing in step S62 of FIG. 12, the processing of steps S63 to S69 is executed (steps S63 to S69) to execute the transport to depository procedure and the store in depository procedure. In the present modified example, a human is not involved in these procedures and, as such, the second time is maintained and is not updated. Then, the execution of the pre-sale control processing is ended.

Thereafter, the post-sale control processing illustrated in FIGS. 19A and 19B is executed. In the present modified example, a human is not involved in the post-sale procedures and, as such, after the first time is set to the second time, the first time is maintained and is not updated.

Modified Example 2 of Embodiment 1

In Embodiment 1, a description is given in which a human is not involved in the transport to depository procedure. However, the present disclosure is not limited thereto. A human is involved in the transport to depository procedure according to the present modified example.

In the present modified example, the transport to depository procedure is performed by the worker of the carrier instead of by the second transporter 21 that is an unmanned ground vehicle. The worker carries a non-illustrated terminal device that has the same configuration and functions as the configuration and functions of the terminal device 19 carried by the recipient.

When the terminal device of the worker receives, from the information processing device 100, an execution command commanding the execution of the transport to depository procedure, the terminal device displays a message commanding the execution of the transport to depository procedure. When the worker views that message, the worker moves to the undertaking location, retrieves the article by hand from the storage locker 214 of the second transporter 21 that is stopped at the undertaking location, and transports the article by hand to the depository 22.

When the worker arrives at the depository 22, the worker operates the input device of the terminal device of the worker or the input device of the depository 22. In accordance with that operation, the terminal device or the depository 22 sends, to the information processing device 100, a completion report that includes the procedure ID "P2" of the transport to depository procedure and that informs that the transport to depository procedure is completed.

The procedure ID "P2" and information expressing the name of the transport to depository procedure, and a flag having a value of "TRUE" expressing that a human is involved in the transport to depository procedure are associated and stored in advance in the second record of the procedure table according to the present modified example.

When the execution of the pre-sale control processing illustrated in FIG. 12 is started using the procedure table according to the present modified example, the information processing device 100 executes the processing of steps S61 and S62 (steps S61 and S62) to set the second time. Next, the controller 110 of the information processing device 100 outputs, to the first data communication circuit 104a with the terminal device of the worker as the destination, an execution command commanding the execution of the transport to depository procedure (step S63).

Thereafter, when the information processing device 100 receives the completion report from the terminal device or the depository 22, the information processing device 100 executes the second time updating processing illustrated in FIG. 18 (step S64). When the execution of the second time updating processing starts, the information processing device 100 executes the processing of steps S81 and S82 (steps S81 and S82). As a result, the acquirer 120 of the information processing device 100 acquires the procedure ID "P2" of the transport to depository procedure, and acquires the acquisition time of the procedure ID "P2" as the time at which the transportation to the depository 22 is performed. The acquisition time is acquired in this manner because, in the present embodiment, the "time at which the transportation to the depository 22 is performed" means the time at which the transport to depository procedure is completed, and the time at which the transport to depository procedure is completed can be equated with the acquisition time at which the procedure ID "P2" of the transport to depository procedure is acquired from the completion report.

Next, the information processing device 100 executes the processing of step S83 (step S83). Thereafter, the manager 130 of the information processing device 100 determines that the value of the involvement flag associated, in the procedure table according to the present modified example, with the procedure ID "P2" of the transport to depository procedure is the value "TRUE" expressing that a person is involved in the transport to depository procedure (step S84; Yes).

Next, the manager 130 of the information processing device 100 updates the second time associated, in the second time table of FIG. 15, with the article ID acquired in step S81 to the acquisition time to manage, as the second time, the acquisition time acquired as the time at which the transportation to the depository 22 is performed (step S85). Then, the manager 130 ends the execution of the second time updating processing.

After the execution of the second time updating processing in step S64 of FIG. 12, the information processing device 100 executes the processing of steps S65 to S69 (steps S65 to S69) and, then, ends the execution of the pre-sale control processing.

In the present modified example, a description is given in which the worker of the carrier performs the entire transport to depository procedure, but the present modified example is not limited thereto and a configuration is possible in which the worker performs a portion of the transport to depository procedure. In such a case, it is sufficient that the second transporter 21 transports the article partway along a movement route from the undertaking location to the depository 22 and, then, the worker retrieves the article by hand from the storage locker 214 of the second transporter 21 and transports the article by hand to the depository 22.

In the present modified example, a description is given in which a human is involved in the transport to depository procedure, but the present modified example is not limited thereto. A configuration is possible in which a human is not involved in the transport to depository procedure, but a human is involved in any one of the store in depository procedure, the retrieval procedure in which the article is retrieved from the depository 22, and the transport to first transporter procedure. In such a case, it is sufficient that the worker of the carrier performs the entirety or a portion of any one of the store in depository procedure, the retrieval procedure, and the transport to first transporter procedure.

Modified Example 3 of Embodiment 1

In Embodiment 1, a description is given in which a human is not involved in the hand over procedure in which the article is handed over to the first transporter 11. However, the present disclosure is not limited thereto. A human is involved in the hand over procedure according to the present modified example.

In the present modified example, the hand over procedure is performed by the worker of the carrier instead of by the second transporter 21. The worker carries the terminal device described in Modified Example 2 of Embodiment 1. As in Modified Example 2 of Embodiment 1, when the terminal device of the worker receives an execution command commanding the execution of the hand over procedure, the terminal device displays a message commanding execution of the hand over procedure. When the worker views that message, the worker moves to the hand over location, retrieves the article by hand from the storage locker 214 of the second transporter 21 that is stopped at the hand over location, and stores the article by hand in the storage locker of the first transporter 11 that is stopped at the hand over location.

When the hand over procedure is completed, the worker operates the input device of the terminal device or the input device of the first transporter 11. In accordance with that operation, the terminal device of the worker or the first transporter 11 sends, to the information processing device 100, a completion report that includes the procedure ID "P6" of hand over procedure and that informs that the hand over procedure is completed.

The procedure ID "P6" and information expressing the name of the hand over procedure, and a flag having a value of "TRUE" expressing that a human is involved in the hand over procedure are associated and stored in advance in the sixth record of the procedure table according to the present modified example.

When the execution of the post-sale control processing illustrated in FIGS. 19A and 19B is started using the procedure table according to the present modified example, the information processing device 100 executes the processing of steps S91 to S100 (steps S91 to S100). Then, the controller 110 of the information processing device 100 outputs, to the first data communication circuit 104a with the terminal device of the worker as the destination, an execution command commanding the execution of hand over procedure (step S101).

Thereafter, when the information processing device 100 receives the completion report from the terminal device or the first transporter 11, the information processing device 100 executes the first time setting processing illustrated in FIG. 21 (step S102). When the execution of the first time setting processing starts, the information processing device 100 executes the processing of steps S111 and S112 (steps S111 and S112). As a result, the acquirer 120 of the information processing device 100 acquires the procedure ID "P6" of hand over procedure, and acquires the acquisition time of the procedure ID "P6" as the time at which the hand over of the article is performed. The acquisition time is acquired in this manner because, in the present embodiment, the "time at which the hand over procedure is performed" means the time at which the hand over procedure is completed, and the time at which the hand over procedure is completed can be equated with the acquisition time at which the procedure ID "P6" of the hand over procedure is acquired from the completion report.

Next, the information processing device 100 executes the processing of step S113 (step S113). Thereafter, the manager 130 of the information processing device 100 determines that the value of the involvement flag associated, in the procedure table according to the present modified example, with the procedure ID "P6" of hand over procedure is the value "TRUE" expressing that a person is involved in the hand over procedure (step S114; Yes).

Next, the manager 130 of the information processing device 100 initializes the first time to the acquisition time (step S116). Next the manager 130 searches the article table of FIG. 20 for a record in which the article ID acquired in step S111 is stored, and associates the first time initialized using the acquisition time with the article ID and stores the associated information in the found record to manage, as the first time, the acquisition time acquired as the time at which the hand over is performed. Then, the manager 130 ends the execution of the first time setting processing.

After the execution of the first time setting processing in step S102 of FIG. 19A, the information processing device 100 executes the processing of steps S103 to S109 (steps S103 to S109). Then, the information processing device 100 ends the execution of the post-sale control processing.

In the present modified example, a description is given in which the worker of the carrier performs the entirety of the hand over procedure, but the present modified example is not limited thereto and a configuration is possible in which the worker performs a portion of the hand over procedure. In such a case, it is sufficient that the worker receives, by hand, the article that the second transporter 21 uses the robot arm 218 to retrieve from the storage locker 214 of the second transporter 21, and stores the received article in the storage locker of the first transporter 11 by hand. Additionally, in such a case, the first transporter 11 may use the robot arm to receive the article that the worker retrieves, by hand, from the storage locker 214 of the second transporter 21, and to store the received article in the storage locker of the first transporter 11.

Modified Example 4 of Embodiment 1

In Embodiment 1, a description is given in which a human is not involved in the transport to locker device procedure. However, the present disclosure is not limited thereto. A human is involved in the transport to locker device procedure according to the present modified example.

In the present modified example, the transport to locker device procedure is performed by the worker of the carrier instead of by the first transporter 11 that is an unmanned ground vehicle. When the transport to locker device procedure is completed, the worker operates the input device of the terminal device described in Modified Example 2 of Embodiment 1 or the input device of the locker device 12. In accordance with that operation, the terminal device of the worker or the locker device 12 sends, to the information processing device 100, a completion report that includes the procedure ID "P7" of the transport to locker device procedure and that informs that the transport to locker device procedure is completed.

The procedure ID "P7" and information expressing the name of the transport to locker device procedure, and a flag having a value of "TRUE" are associated and stored in advance in the seventh record of the procedure table according to the present modified example.

Next, when the execution of the post-sale control processing illustrated in FIGS. 19A and 19B is started using the procedure table according to the present modified example, the processing of steps S91 to S103 is executed (steps S91 to S103) and, then, the controller 110 of the information processing device 100 outputs, to the first data communication circuit 104a with the terminal device of the worker as the destination, an execution command commanding the execution of the transport to locker device procedure (step S104).

Thereafter, when the information processing device 100 receives a completion report from the terminal device or the locker device 12, the information processing device 100 executes the first time updating processing illustrated in FIG. 22 (step S105). When the execution of the first time updating processing starts, the information processing device 100 executes the processing of steps S121 to S124 (steps S121 to S124). As a result, the acquirer 120 of the information processing device 100 acquires the procedure ID "P7" of the transport to locker device procedure, and acquires the acquisition time of the procedure ID "P7" as the time at which the transportation to the locker device 12 is performed. Additionally, the manager 130 determines that the value of the involvement flag associated, in the procedure table according to the present modified example, with the procedure ID "P7" of the transport to locker device procedure is "TRUE" (step S124; Yes).

Next, the manager 130 of the information processing device 100 updates the first time associated, in the article table of FIG. 20, with the article ID acquired in step S121 to the acquisition time (step S125) to manage, as the first time, the acquisition time acquired as the time at which the transportation to the locker device 12 is performed. Then, the manager 130 ends the execution of the first time updating processing.

After the execution of the first time updating processing in step S105 of FIG. 19B, the information processing device 100 executes the processing of steps S106 to S109 (steps S106 to S109). Then, the information processing device 100 ends the execution of the post-sale control processing.

In the present modified example, a description is given in which the worker of the carrier performs the entire transport to locker device procedure, but the present modified example is not limited thereto and a configuration is possible in which the worker performs a portion of the transport to locker device procedure.

Additionally, in the present modified example, a description is given in which a human is involved in the transport to locker device procedure, but the present modified example is not limited thereto. A human is not involved in the transport to locker device procedure, but a person may be involved in the store in locker device procedure. In such a case, it is sufficient that the worker performs the entirety or a portion of the store in locker device procedure.

According to these configurations, in a case in which a human is involved in the hand over of the article to the first transporter 11, the manager 130 of the distribution system 1 manages, as the first time, the time at which the hand over is performed. Additionally, according to these configurations, the information processing device 100 of the distribution system 1 further includes an acquirer 120 that acquires procedure IDs identifying procedures that are related to the delivery of the article and that are performed on that article. Moreover, in a case in which, in the information storage 190 in which a procedure ID identifying a procedure and a flag expressing whether or not a human is involved in that procedure are associated and stored in plurality, the flag associated with the acquired procedure ID expresses that a human is involved, the manager 130 of the information processing device 100 updates the first time using the time at which the procedure ID is acquired. As such, the distribution system 1 can update the first time with a lighter calculation load than when updating the first time by analyzing an image obtained from an imaging device, for example, to detect that a human has touched the article and the time when the article has been touched by a human. Additionally, the configuration of the distribution system 1 can be simplified compared to such cases and, as such, the manufacturing cost and installation cost of the distribution system 1 can be reduced.

Modified Example 5 of Embodiment 1

In Embodiment 1 and Modified Examples 2 to 4 of Embodiment 1, descriptions are given in which a human is involved in any one procedure of the undertaking procedure to the store in locker device procedure. However, the present disclosure is not limited thereto. Configurations are possible in which a human is involved in two or more procedures of the undertaking procedure to the store in locker device procedure.

Modified Example 6 of Embodiment 1

In Embodiment 1, a description is given in which the second transporter 21 includes the robot arm 218. Additionally, in Embodiment 1, a description is given in which, in the store in depository procedure, the second transporter 21 uses the robot arm 218 to move the article from the second transporter 21 to the depository 22. However, Embodiment 1 is not limited thereto, and a configuration is possible in which the depository 22 includes a non-illustrated robot arm that has the same configuration and functions as the configuration and functions of the robot arm 218 of the second transporter 21. Additionally, a configuration is possible in which, in the store in depository procedure, the depository 22 uses the robot arm of the depository 22 to move the article from the second transporter 21 to the depository 22.

Additionally, a configuration is possible in which, in the store in depository procedure, the second transporter 21 and the depository 22 move the article from the second transporter 21 to the depository 22. In such a case, it is sufficient that the second transporter 21 uses the robot arm 218 to retrieve the article from the second transporter 21 and, then, the depository 22 uses the robot arm of the depository 22 to receive the retrieved article from the second transporter 21 and uses the robot arm of the depository 22 to store the received article in the depository 22.

In Embodiment 1, a description is given in which, in the hand over procedure in which the article is handed over from the second transporter 21 to the first transporter 11, the second transporter 21 uses the robot arm 218 to move the article from the second transporter 21 to the first transporter 11, but Embodiment 1 is not limited thereto. A configuration is possible in which, in the hand over procedure, the first transporter 11 uses the non-illustrated robot arm of the first transporter 11 to move the article from the second transporter 21 to the first transporter 11.

Additionally, a configuration is possible in which, in the hand over procedure, the first transporter 11 and the second transporter 21 move the article from the second transporter 21 to the first transporter 11. In such a case, it is sufficient that the second transporter 21 uses the robot arm 218 to retrieve the article from the second transporter 21 and, then, the first transporter 11 uses the robot arm of the first transporter 11 to receive the retrieved article from the second transporter 21 and uses the robot arm of the first transporter 11 to store the received article in the first transporter 11.

In Embodiment 1, a description is given in which the first transporter 11 includes a non-illustrated robot arm. Additionally, in Embodiment 1, a description is given in which, in the store in locker device procedure, the first transporter 11 uses the robot arm of the first transporter 11 to move the article from the first transporter 11 to the locker device 12. However, Embodiment 1 is not limited thereto, and a configuration is possible in which the locker device 12 includes a non-illustrated robot arm having the same configuration and functions as the configuration and functions of the robot arm 218 of the second transporter 21. Additionally, a configuration is possible in which, in the store in locker device procedure, the locker device 12 uses the robot arm of the locker device 12 to move the article from the first transporter 11 to the locker device 12.

Moreover, a configuration is possible in which, in the store in locker device procedure, the first transporter 11 and the locker device 12 move the article from the first transporter 11 to the locker device 12. In such a case, it is sufficient that the first transporter 11 uses the robot arm of the first transporter 11 to retrieve the article from the first transporter 11 and, then, the locker device 12 uses the robot arm of the locker device 12 to receive the retrieved article from the first transporter 11 and uses the robot arm of the locker device 12 to store the received article in the locker device 12.

Modified Example 7 of Embodiment 1

In Embodiment 1, a description is given in which the manager 130 of the information processing device 100 manages the first time and the second time. Additionally, a description is given in which the notifier 140 of the information processing device 100 performs a notification informing that a human has not touched the article later than the first time.

However, Embodiment 1 is not limited thereto and the manager 130 of the information processing device 100 according to the present modified example manages a first amount of elapsed time that is an amount of elapsed time from the first time, and a second amount of elapsed time that is an amount of elapsed time from the second time. Additionally, the notifier 140 according to the present modified example performs a notification informing that a human has not contacted the article throughout the first amount of elapsed time.

To realize this, the information storage 190 of the information processing device 100 according to the present modified example stores, in advance, a non-illustrated second amount of elapsed time table instead of the second time table illustrated in FIG. 15. The article ID identifying the article, and a thread ID identifying a thread in which a timekeeping program is executed are associated and stored in the second amount of elapsed time table. The timekeeping program measures the second amount of elapsed time of the article.

When the execution of the timekeeping program is started, processing is performed for sleeping for one minute and, then, a counter expressing the amount of elapsed time is incremented by a value of "1." Then, the timekeeping program repeats the processing described above from the processing for sleeping.

Figure 24:
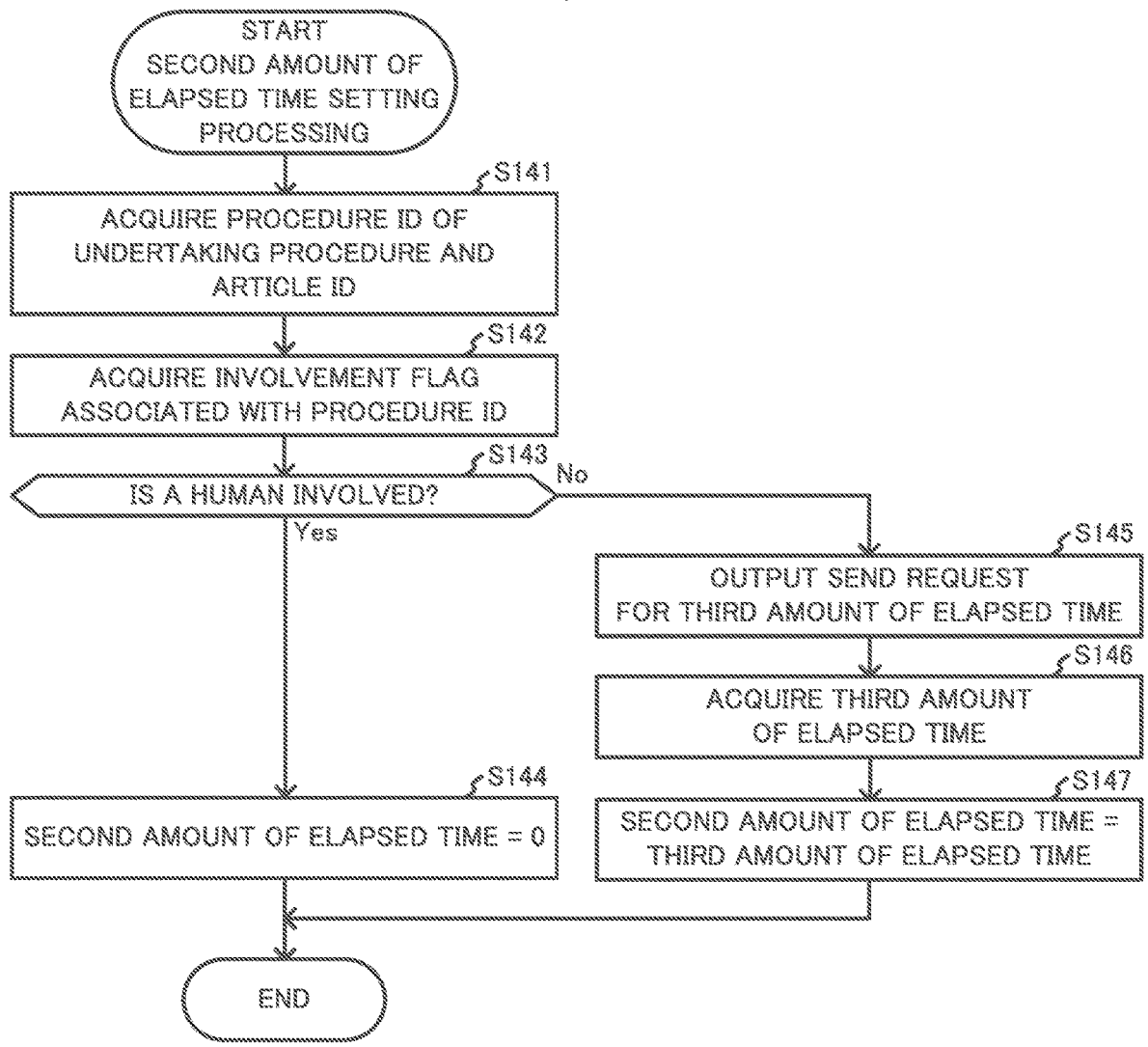
FIG. 24 is a flowchart illustrating an example of second amount of elapsed time setting processing executed by the information processing device.

In step S62 of FIG. 12, instead of the second time setting processing illustrated in FIG. 17, the information processing device 100 according to the present modified example executes a second amount of elapsed time setting processing such as illustrated in FIG. 24 for setting the second amount of elapsed time.

When the execution of the second amount of elapsed time setting processing starts, the acquirer 120 of the information processing device 100 executes the same processing as steps S71 and S73 of FIG. 17 (steps S141 and S142) to acquire the article ID of the article on which the undertaking procedure is performed and the procedure ID "P1" of the undertaking procedure, and acquire the involvement flag associated with the acquired procedure ID "P1" of the undertaking procedure.

Next, when the manager 130 of the information processing device 100 determines that the value of the acquired involvement flag is the value "TRUE" expressing that a person is involved (step S143; Yes), the manager 130 generates a thread in which the timekeeping program for measuring the second amount of elapsed time is executed, and the acquirer 120 acquires a thread ID identifying the generated thread from the OS.

Thereafter, the manager 130 of the information processing device 100 initializes, to "0" minutes, a counter that is used by the timekeeping program executed in the generated thread and that is a counter that expresses the second amount of elapsed time (step S144) and, then, starts the execution of the timekeeping program. As a result, the manager 130 causes the timekeeping program to measure the amount of elapsed time from the time at which the undertaking of the article is performed or from the acquisition time at which the procedure ID "P1" of the undertaking procedure is acquired. Such measurement is performed because, in the present embodiment, the "time at which the undertaking is performed" means the time at which the undertaking procedure is completed, and a time length is less than or equal to a predetermined time length such as "1" minute, for example. Here the time length is a time length from the time at which the execution of the undertaking procedure is completed to a time at which the information processing device 100 acquires the procedure ID "P1" of the undertaking procedure from the completion report of the undertaking procedure, initializes the counter on the basis of the value of the involvement flag associated with the procedure ID, and finishes restarting the execution of the timekeeping program. That is, such measurement is performed because the time at which the undertaking of the article is performed, the acquisition time at which the procedure ID "P1" of the undertaking procedure is acquired, and the time at which the execution of the timekeeping program is restarted can be equated with each other.

Thereafter, the manager 130 of the information processing device 100 associates the article ID acquired in step S141 and the acquired thread ID and stores the associated information in the second amount of elapsed time table to manage the time measured by the timekeeping program as the second amount of elapsed time. Then, the manager 130 ends the execution of the second amount of elapsed time setting processing.

In step S143, when the manager 130 of the information processing device 100 determines that the value of the acquired involvement flag is the value "FALSE" expressing that a person is not involved (step S143; No), the manager 130 generates a send request requesting the sending of information expressing a third amount of elapsed time that is an amount of elapsed time from a third time. Then, the manager 130 outputs the generated send request to the first data communication circuit 104a with the information processing device of the third distribution mechanism as the destination (step S145).

When the first data communication circuit 104a of the information processing device 100 receives the information expressing the third amount of elapsed time, the acquirer 120 of the information processing device 100 acquires the information expressing the third amount of elapsed time from the first data communication circuit 104a (step S146).

Thereafter, the manager 130 of the information processing device 100 generates a thread, and the acquirer 120 acquires a thread ID identifying the generated thread. Next, the manager 130 initializes, to the third amount of elapsed time, the counter that expresses the second amount of elapsed time that is used in the timekeeping program executed in the generated thread (step S147) and, then, starts the execution of the timekeeping program. Then, the manager 130 associates the article ID and the thread ID and stores the associated information in the second amount of elapsed time table to manage the third amount of elapsed time as the second amount of elapsed time. Then, the manager 130 ends the execution of the second amount of elapsed time setting processing.

Figure 25:
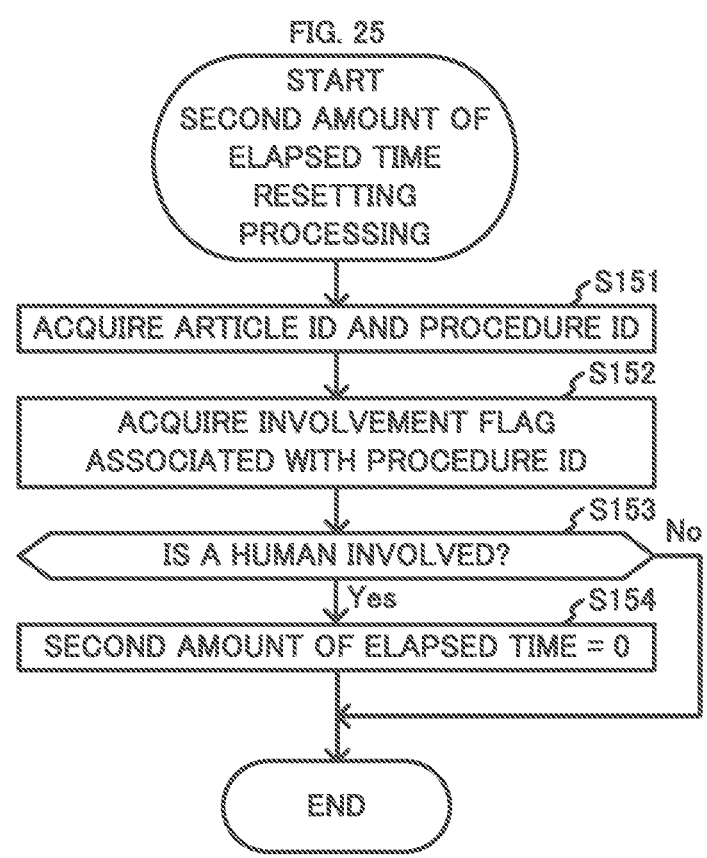
FIG. 25 is a flowchart illustrating an example of second amount of elapsed time resetting processing executed by the information processing device.

In steps S64 and S66 of FIG. 12, and in steps S98 and S100 of FIG. 19A, instead of the second time updating processing illustrated in FIG. 18, the information processing device 100 according to the present modified example executes second amount of elapsed time resetting processing such as illustrated in FIG. 25 for resetting the second amount of elapsed time.

When the execution of the second amount of elapsed time resetting processing starts, the acquirer 120 of the information processing device 100 executes the same processing as steps S81 and S83 of FIG. 18 (steps S151 and S152), and acquires one of the procedure IDs "P2" to "P5" of the executed procedure and the article ID of the article on which that procedure is performed. Additionally, the acquirer 120 acquires the involvement flag associated with the acquired one of the procedure IDs "P2" to "P5."

Next, when the manager 130 of the information processing device 100 determines that the value of the acquired involvement flag is the value "FALSE" expressing that a person is not involved (step S153; No), the manager 130 ends the execution of the second amount of elapsed time resetting processing without resetting the second amount of elapsed time.

In contrast, when the manager 130 of the information processing device 100 determines that the value of the acquired involvement flag is the value "TRUE" expressing that a person is involved (step S153; Yes), the acquirer 120 acquires the thread ID associated with the article ID in the non-illustrated second amount of elapsed time table. Then, the manager 130 ends the execution of the timekeeping program executed in the thread identified by the acquired thread ID and, then, initializes the counter expressing the second amount of elapsed time of the timekeeping program to "0" minutes (step S154). Next, the manager 130 restarts the execution of the timekeeping program. As a result, the manager 130 causes the timekeeping program to measure the amount of elapsed time from the time at which the transportation of the article to the depository 22, the storage of the article in the depository 22, the retrieval of the article from the depository 22, or the transportation of the article to the first transporter 11 is performed or from the acquisition time at which the one of the procedure IDs "P2" to "P5" is acquired. Additionally, as a result, the manager 130 manages the amount of time measured by the timekeeping program as the second amount of elapsed time. Then, the manager 130 ends the execution of the second amount of elapsed time resetting processing.

Furthermore, instead of the article table illustrated in FIG. 20, a non-illustrated article table is stored in advance in the information storage 190 of the information processing device 100 according to the present modified example. The article ID of a sold article, the information expressing the destination of that article, the box ID identifying the storage box of the locker device 12 in which that article is stored, information expressing a password used to authenticate the recipient of that article, and the thread ID of the thread in which the timekeeping program is executed that measures the first amount of elapsed time of that article are associated and stored in the article table according to the present modified example.

In step S101 of FIG. 19A, the information processing device 100 according to the present modified example outputs an execution command commanding the execution of the hand over procedure and, then, in step S102, instead of the first time setting processing illustrated in FIG. 21, the information processing device 100 according to the present modified example executes non-illustrated first amount of elapsed time setting processing for setting the first amount of elapsed time.

When the execution of the first amount of elapsed time setting processing starts, the information processing device 100 executes the same processing as steps S141 to S147 of FIG. 24. As a result, the acquirer 120 of the information processing device 100 acquires the article ID of the article on which the hand over procedure is performed, and the procedure ID "P6" of the hand over procedure. Next, when the manager 130 of the information processing device 100 determines that the value of the involvement flag associated with the procedure ID "P6" of the hand over procedure is the value "TRUE" expressing that a person is involved, the manager 130 generates a thread in which the timekeeping program for measuring the first amount of elapsed time is executed. Then, the manager 130 initializes the counter expressing the first amount of elapsed time to "0" minutes and, then, starts the execution of the timekeeping program in that thread. As a result, the manager 130 causes the timekeeping program to measure the amount of elapsed time from the time at which the handing over is performed or the acquisition time at which the procedure ID "P6" of the hand over procedure is acquired.

Such a measurement is performed because, in the present embodiment, the "time at which the hand over is performed" means the time at which the hand over procedure is completed, and a time length is less than or equal to a predetermined time length. Here the time length is a time length from the time at which the execution of the hand over procedure is completed to a time at which the information processing device 100 that receives the completion report of the hand over procedure acquires the procedure ID "P6" of the hand over procedure from the completion report, initializes the counter on the basis of the procedure ID, and finishes restarting the execution of the timekeeping program. That is, such a measurement is performed because the time at which the handing over is performed, the acquisition time at which the procedure ID "P6" of the hand over procedure is acquired, and the time at which the execution of the timekeeping program is restarted can be equated with each other.

Thereafter, the manager 130 of the information processing device 100 associates the thread ID of the generated thread with the article ID of the sold article, and stores the associated information in the article table according to the present modified example. As a result, the manager 130 manages the amount of elapsed time measured by the timekeeping program as the first amount of elapsed time. Then, the manager 130 ends the execution of the first amount of elapsed time setting processing.

In contrast, when the manager 130 of the information processing device 100 determines that the value of the acquired involvement flag is the value "FALSE" expressing that a person is not involved, the manager 130 generates a thread, initializes, the counter expressing the first amount of elapsed time to the second amount of elapsed time and, then, starts the execution of the timekeeping program in that thread. Next, the manager 130 associates the thread ID with the article ID and stores the associated information in the article table to manage the second amount of elapsed time as the first amount of elapsed time. Then, the manager 130 ends the execution of the first amount of elapsed time setting processing.

In steps S105 and S107 of FIG. 19B, instead of the first time updating processing illustrated in FIG. 22, the information processing device 100 according to the present modified example executes non-illustrated first amount of elapsed time resetting processing for resetting the first amount of elapsed time.

When the execution of the first amount of elapsed time resetting processing starts, the information processing device 100 executes the same processing as steps S151 to S154 of FIG. 25. As a result, the information processing device 100 acquires the procedure ID identifying the completed procedure, and the article ID of the article on which that procedure is performed, and acquires the involvement flag associated with the acquired procedure ID. Next, when the manager 130 of the information processing device 100 determines that the value of the acquired involvement flag is "FALSE" expressing that a person is not involved, the manager 130 continues the measuring without resetting the first amount of elapsed time. Then, the manager 130 ends the execution of the first amount of elapsed time resetting processing.

In contrast, when the information processing device 100 determines that the value of the acquired involvement flag is the value "TRUE" expressing that a person is involved, the information processing device 100 acquires the thread ID associated with the acquired article ID. Next, the manager 130 of the information processing device 100 ends the execution of the timekeeping program executed in the thread identified by the acquired thread ID and, then, initializes, to "0" minutes, the counter that expresses the first amount of elapsed time of the timekeeping program. Then, the manager 130 restarts the execution of the timekeeping program. As a result, the manager 130 causes the timekeeping program to measure the amount of elapsed time from the time at which the article is transported to or stored in the locker device 12, or from the acquisition time at which the procedure ID "P7" of the transport to locker device procedure or the procedure ID "P8" of the store in locker device procedure is acquired. Additionally, as a result, the manager 130 manages the amount of elapsed time measured by the timekeeping program as the first amount of elapsed time. Then, the manager 130 ends the execution of the first amount of elapsed time resetting processing.

Additionally, instead of the notification processing illustrated in FIG. 23 in which the notification to the recipient is performed on the basis of the first time, the notifier 140 of the information processing device 100 according to the present modified example executes non-illustrated notification processing for performing a notification to the recipient on the basis of the first amount of elapsed time.

When the execution of the non-illustrated notification processing starts, the acquirer 120 of the information processing device 100 acquires, from the article table according to the present modified example, the box ID and the information expressing the password associated with the article ID of the article that is delivered to the locker device 12, and the thread ID. Next, the acquirer 120 acquires the first amount of elapsed time by referencing the value of the counter used in the timekeeping program executed in the thread identified by the thread ID.

Thereafter, the notifier 140 of the information processing device 100 generates a notification that includes the box ID, the password, and the first amount of elapsed time, and that informs that the article is delivered to the storage box identified by the box ID of the locker device 12 at the destination, the password is required to retrieve the article, and a human has not contacted the article throughout the first amount of elapsed time. Then, the notifier 140 outputs the generated notification to the first data communication circuit 104a with the terminal device 19 carried by the recipient as the destination and, then, ends the execution of the notification processing.

According to these configurations, the distribution system 1 includes the first distribution mechanism 10 including the first transporter 11 that transports an article to the destination of the article, and the manager 130 that manages the first amount of elapsed time that is an amount of elapsed time from the first time, the first time being a time earlier than the receiving time at which the article transported by the first transporter 11 is received and being the last time at which a human contacted the article. As such, the distribution system 1 can manage the first amount of elapsed time that is the amount of elapsed time from the last time at which a human touched the article prior to the article being received by the recipient.

According to these configurations, the distribution system 1 further includes the second distribution mechanism 20 that is a mechanism different than the first distribution mechanism 10 and that transports or stores the article. The manager 130 of the information processing device 100 further manages the second amount of elapsed time that is an amount of elapsed time from the second time, the second time being a time earlier than the hand over time at which the second distribution mechanism 20 hands over the article to the first distribution mechanism 10 and being the last time at which a human contacted the article that the second distribution mechanism 20 transports or stores. As such, the distribution system 1 can manage the second amount of elapsed time that is the amount of elapsed time from the last time at which a human touched the article prior to the article being handed over to the first distribution mechanism 10.

According to these configurations, the distribution system 1 further includes the notifier 140 that performs a notification to the recipient on the basis of the first amount of elapsed time. The notification performed by the notifier 140 informs that a human has not contacted the article throughout the first amount of elapsed time. Due to these configurations, as long as the recipient receives the article after waiting the time difference between the target amount of elapsed time and the first amount of elapsed time, even if a virus or bacterium is adhered to article due to contact with a human, it is possible to suppress the recipient of that article from being infected with that virus or bacterium.

Modified Example 8 of Embodiment 1

Modified Example 3 of Embodiment 1 and Modified Example 7 of Embodiment 1 can be combined. In such a configuration, in a case in which a human is involved in the hand over of the article to the first transporter 11, the manager 130 of the information processing device 100 can manage, as the first amount of elapsed time, the amount of elapsed time from the time at which the hand over is performed.

Modified Example 9 of Embodiment 1

In Embodiment 1, a description is given in which the operation for inputting the box ID and the password on the input device of the locker device 12 is performed by the recipient at or after the recommended receiving start time, but Embodiment 1 is not limited thereto. In the present modified example, the recipient performs the operation for inputting the box ID and the password on the input device of the locker device 12 at a time earlier than the recommended receiving start time.

As described in Embodiment 1, in accordance with that operation, the locker device 12 according to the present modified example sends an inquiry that includes the box ID and the password to the information processing device 100. Even when the inquiry is received at a time earlier than the recommended receiving start time, when the combination of the box ID and the password included in the inquiry matches the combination of the box ID and the password sent to the terminal device 19, the information processing device 100 returns a response that unlocking is allowed. In contrast, when these combinations do not match, the information processing device 100 returns a response that unlocking is not allowed.

Modified Example 10 of Embodiment 1

In Modified Example 9 of Embodiment 1, a description is given in which, even when an inquiry is received at a time earlier than the recommended receiving start time, when the combination of the box ID and the password included in the inquiry matches the combination of the box ID and the password sent to the terminal device 19, the information processing device 100 returns a response that unlocking is allowed. However, Embodiment 1 is not limited thereto and, when an inquiry is received at a time earlier than the recommended receiving start time, the information processing device 100 returns a response that unlocking is not allowed.

To realize this, instead of the article table illustrated in FIG. 20, a non-illustrated article table is stored in advance in the information storage 190 of the information processing device 100 according to the present modified example. The article ID of a sold article, the information expressing the destination of that article, the first time of that article, the box ID identifying the storage box of the locker device 12 in which that article is stored, information expressing the password used to authenticate the recipient of that article, and the recommended receiving start time of that article are associated and stored in the article table according to the present modified example.

Instead of the notification processing of FIG. 23, the information processing device 100 according to the present modified example executes non-illustrated notification processing. When the execution of the notification processing according to the present modified example starts, the same processing as steps S131 to S133 of FIG. 23 is executed. As a result, the first time of the article stored in the locker device 12 is acquired, and the recommended receiving start time is calculated on the basis of the acquired first time.

Thereafter, the manager 130 of the information processing device 100 searches the article table according to the present modified example for a record in which the article ID of that article is stored, and stores the calculated recommended receiving start time in association with that article ID in the found record.

Thereafter, the information processing device 100 executes the same processing as step S134 of FIG. 23 to send, to the terminal device 19 carried by the recipient, a notification including the first time, the recommended receiving start time, the box ID, and the password and, then, ends the execution of the notification processing.

When the first data communication circuit 104a of the information processing device 100 receives the inquiry from the locker device 12 that is operated by the recipient that views the notification, the CPU 101 of the information processing device 100 executes non-illustrated unlock permission processing.

When the execution of the unlock permission processing starts, the acquirer 120 of the information processing device 100 acquires the box ID and the information expressing the password from the received inquiry, and acquires, from the article table according to the present modified example, the recommended receiving start time associated with the box ID acquired from the inquiry. Next, the acquirer 120 acquires the system time from the OS, for example, and when the controller 110 determines that the acquired system time is a time that is earlier than the acquired recommended receiving start time, the controller 110 outputs, to the first data communication circuit 104a with the locker device 12 as the destination, a response that unlocking is not allowed.

In contrast, when the controller 110 determines that the acquired system time is a time that is equal to or later than the acquired recommended receiving start time, as described in Embodiment 1, the acquirer 120 of the information processing device 100 acquires, from the article table according to the present modified example, the information expressing the password associated with the acquired box ID. Next, when the controller 110 determines that the password expressed in the information acquired from the inquiry and the password expressed in the information acquired from the article table match, the controller 110 outputs a response that unlocking is allowed to the first data communication circuit 104a with the locker device 12 as the destination. In contrast, when the controller 110 determines that these passwords do not match, the controller 110 outputs, to the first data communication circuit 104a with the locker device 12 as the destination, a response that unlocking is not allowed. Then, the controller 110 ends the execution of the unlock permission processing.

According to these configurations, the target amount of elapsed time is the time from when the predetermined virus or bacterium is discharged from the body of a human to when the magnitude of infectivity of that virus or bacterium is less than or equal to a predetermined magnitude. Additionally, the distribution system 1 further includes the controller 110 that performs control for causing the first transporter 11 of the first distribution mechanism 10 to transport the article to the locker device 12 installed at the destination and, then, control for unlocking the locked locker device 12 storing the transported article at the recommended receiving start time that is the target amount of elapsed time after the first time, or later. As such, since the receiving time of the article can be set to the recommended receiving start time or later, even if a virus or bacterium is adhered to the article due to contact with a human, the distribution system 1 can suppress the recipient of the article from becoming infected with that virus or bacterium.

Modified Example 11 of Embodiment 1

Modified Example 7 of Embodiment 1 and Modified Example 10 of Embodiment 1 can be combined. The controller 110 of the information processing device 100 according to the present modified example that is a combination of Modified Example 7 of Embodiment 1 and Modified example 10 of Embodiment 1 performs control for unlocking the locker device 12 at a time at which the first amount of elapsed time is the target amount of elapsed time, or later.

To realize this, the acquirer 120 of the information processing device 100 acquires the box ID and the information expressing the password from the inquiry received from the terminal device 19 of the recipient, and acquires, from the article table according to the present modified example, the thread ID associated with the box ID acquired from the inquiry. Next, the acquirer 120 acquires the first amount of elapsed time by referencing the counter of the timekeeping program executed in the thread identified by the acquired thread ID. Then, the acquirer 120 acquires the information expressing the target amount of elapsed time from the information storage 190.

Next, when the controller 110 of the information processing device 100 determines that the length of the acquired first amount of elapsed time is less than the length of the acquired target amount of elapsed time, the controller 110 determines that the system time is a time earlier than the recommended receiving start time at which the first amount of elapsed time is the target amount of elapsed time. Then, the controller 110 outputs a response that unlocking is not allowed to the first data communication circuit 104a with the locker device 12 as the destination.

In contrast, when the controller 110 of the information processing device 100 determines that the length of the acquired first amount of elapsed time is greater than or equal to the length of the acquired target amount of elapsed time, the controller 110 determines that the system time is the time of the recommended receiving start time, or later. Then, when the controller 110 determines that the password expressed in the information acquired from the inquiry and the password expressed in the information acquired from the article table match, the controller 110 outputs a response that unlocking is allowed, and when the controller 110 determines that these passwords do not match, the controller 110 outputs a response that unlocking is not allowed.

Modified Example 12 of Embodiment 1

In Embodiment 1, a description is given in which, when the article is stored in the locker device 12, the notifier 140 of the information processing device 100 performs a notification informing that the article is delivered to the locker device 12. However, Embodiment 1 is not limited thereto. The notifier 140 of the information processing device 100 according to the present modified example performs the notification informing that the article is delivered to the locker device 12 when the recommended receiving start time passes.

To realize this, instead of the article table illustrated in FIG. 20, a non-illustrated article table is stored in advance in the information storage 190 of the information processing device 100 according to the present modified example. The article ID, the information expressing the destination, the first time, the box ID, the information expressing the password, the recommended receiving start time, and a flag expressing whether or not the notification is performed are associated and stored in the article table according to the present modified example.

When an article is stored in the locker device 12 due to the execution of the post-sale control processing illustrated in FIGS. 19A and 19B being completed, the CPU 101 of the information processing device 100 according to the present modified example executes non-illustrated time calculation processing for calculating the recommended receiving start time of that article.

When the execution of the time calculation processing starts, the information processing device 100 executes the same processing as steps S131 to S133 of FIG. 23. As a result, the first time of the article stored in the locker device 12 is acquired, and the recommended receiving start time is calculated on the basis of the acquired first time. Thereafter, the manager 130 of the information processing device 100 searches the article table according to the present modified example for a record in which the article ID of that article is stored, and stores the calculated recommended receiving start time and a flag expressing that a notification is not performed in association with that article ID in the found record. Then, the manager 130 ends the execution of the time calculation processing.

When the CPU 101 of the information processing device 100 according to the present modified example is started up, instead of the notification processing illustrated in FIG. 23, the CPU 101 executes non-illustrated notification processing at a predetermined interval such as one minute, for example.

When the execution of the notification processing according to the present modified example starts, the acquirer 120 of the information processing device 100 acquires the system time from the OS, for example. Next, the notifier 140 determines whether or not a record exists, in the article table according to the present modified example, in which a recommended receiving start time at or earlier than the acquired system time and the flag expressing that a notification is not performed are stored. At this time, when the notifier 140 determines that no such record exists, the notifier 140 ends the execution of the notification processing.

In contrast, when the notifier 140 of the information processing device 100 determines that such a record exists, the acquirer 120 selects one of the records and acquires the box ID and the password from the selected record.

Thereafter, the notifier 140 generates a notification informing that an article is delivered to the storage box identified by the box ID of the locker device 12 at the destination, the password is required to receive that article, and the target amount of elapsed time has elapsed since a human last touched that article.

Next, the notifier 140 of the information processing device 100 outputs the generated notification to the first data communication circuit 104*a* with the terminal device 19 carried by the recipient as the destination. Then, the notifier 140 updates the flag of the selected record to a flag expressing that a notification is performed and, then, ends the execution of the notification processing.

According to these configurations, the notifier 140 of the distribution system 1 further performs a notification informing that the target amount of elapsed time has elapsed since a human last touched the article. This notification is performed at the recommended receiving start time, which is a time the target amount of elapsed time after the first time, or later. As such, as long as the recipient receives the article after viewing that notification, even if a virus or bacterium is adhered to the article due to contact with a human, it is possible to suppress the recipient of the article from becoming infected with that virus or bacterium. Additionally, even if the recipient does not know the target amount of elapsed time, as long as the recipient views that notification, the recipient can ascertain that the magnitude of infectivity of that virus or bacterium is less than or equal to the predetermined magnitude due to the target amount of elapsed time passing since a human last touched the article. As such, the convenience of the recipient is improved.

According to these configurations, the notifier 140 of the distribution system 1 performs, at the recommended receiving start time or later, a notification informing that an article is delivered to the locker device 12 at the destination, and does not perform that notification earlier than the recommended receiving start time. As such, even when, for example, unlocking of the locker device 12 is not restricted at times earlier than the recommended receiving start time, the distribution system 1 can set the receiving time to a time at the recommended receiving start time or later. As such, even if a virus or bacterium is adhered to the article due to contact with a human, it is possible to suppress the recipient of the article from becoming infected with that virus or bacterium.

Modified Example 13 of Embodiment 1

Modified Example 7 of Embodiment 1 and Modified Example 12 of Embodiment 1 can be combined. To realize this, the notifier 140 of the information processing device 100 according to the present modified example that is a combination of Modified Example 7 of Embodiment 1 and Modified Example 12 of Embodiment 1 performs a notification informing that the target amount of elapsed time has elapsed since a human last touched the article. This notification is performed at a time at which the first amount of elapsed time is the target amount of elapsed time, or later.

Modified Example 14 of Embodiment 1

In Embodiment 1, a description is given in which the first distribution mechanism 10 of the distribution system 1 includes the first transporter 11 and the locker device 12. However, Embodiment 1 is not limited thereto. The first distribution mechanism 10 according to the present modified example includes the first transporter 11 but does not include the locker device 12. When the first transporter 11 according to the present modified example transports an article to a destination of that article, the first transporter 11 stops at that destination.

The first transporter 11 may travel around or travel back and forth in the vicinity of the destination at a speed that is less than or equal to a predetermined speed. The vicinity of the destination is an area that is more to the destination side than a boundary line that is a predetermined distance from the destination.

The recipient performs an operation for inputting the password on the non-illustrated input device of the first transporter 11. The non-illustrated CPU of the first transporter 11 acquires information expressing the password on the basis of a signal outputted from the input device, and outputs an inquiry including the acquired information to the data communication circuit with the information processing device 100 as the destination.

Thereafter, when the data communication circuit of the first transporter 11 receives, from the information processing device 100, a response that unlocking is not allowed, the CPU of the first transporter 11 displays, on the non-illustrated display device, a message informing that the password is incorrect. In contrast, when a response that unlocking is allowed is received, the CPU of the first transporter 11 outputs, to the drive circuit, a control signal for unlocking the storage locker. The recipient opens the door of the unlocked storage locker and receives the purchased article.

Modified Example 15 of Embodiment 1

In Embodiment 1, a description is given in which the locker device 12 is installed at the entrance of the apartment building where the recipient resides. However, Embodiment 1 is not limited thereto. The locker device 12 may be installed at an entrance of an apartment complex including apartments, an office building, a hotel, a commercial facility such as a convenience store, a shopping mall, and a department store, or a public facility such as a train station, an airport, and a bus stop, or on the doorstep of a house. Additionally, the locker device 12 may be installed in a lobby of an apartment complex, an office building, a hotel, a commercial facility, or a public facility. Furthermore, the locker device 12 may be installed in a yard or a parking lot of a house, an apartment complex, an office building, a hotel, a commercial facility, or a public facility. Moreover, the locker device 12 may be installed in a corridor of an apartment complex, an office building, a hotel, a commercial facility, or a public facility.

In Modified Example 14 of Embodiment 1, a description is given in which the first transporter 11 stops at the destination or travels around or travels back and forth in the vicinity of the destination. The location of the destination where the first transporter 11 stops, or the vicinity of the destination where the first transporter 11 travels around or the like may be the entrance of an apartment complex, an office building, a hotel, a commercial facility, or a public facility, or the doorstep of a house. Additionally, the location of the destination where the first transporter 11 stops, or the vicinity of the destination where the first transporter 11 travels around or the like may be a lobby of an apartment complex, an office building, a hotel, a commercial facility, or a public facility, a yard or a parking lot of a house, an apartment complex, an office building, a hotel, a commercial facility, or a public facility, or a corridor of an apartment complex, an office building, a hotel, a commercial facility, or a public facility.

Modified Example 16 of Embodiment 1

Figure 26:
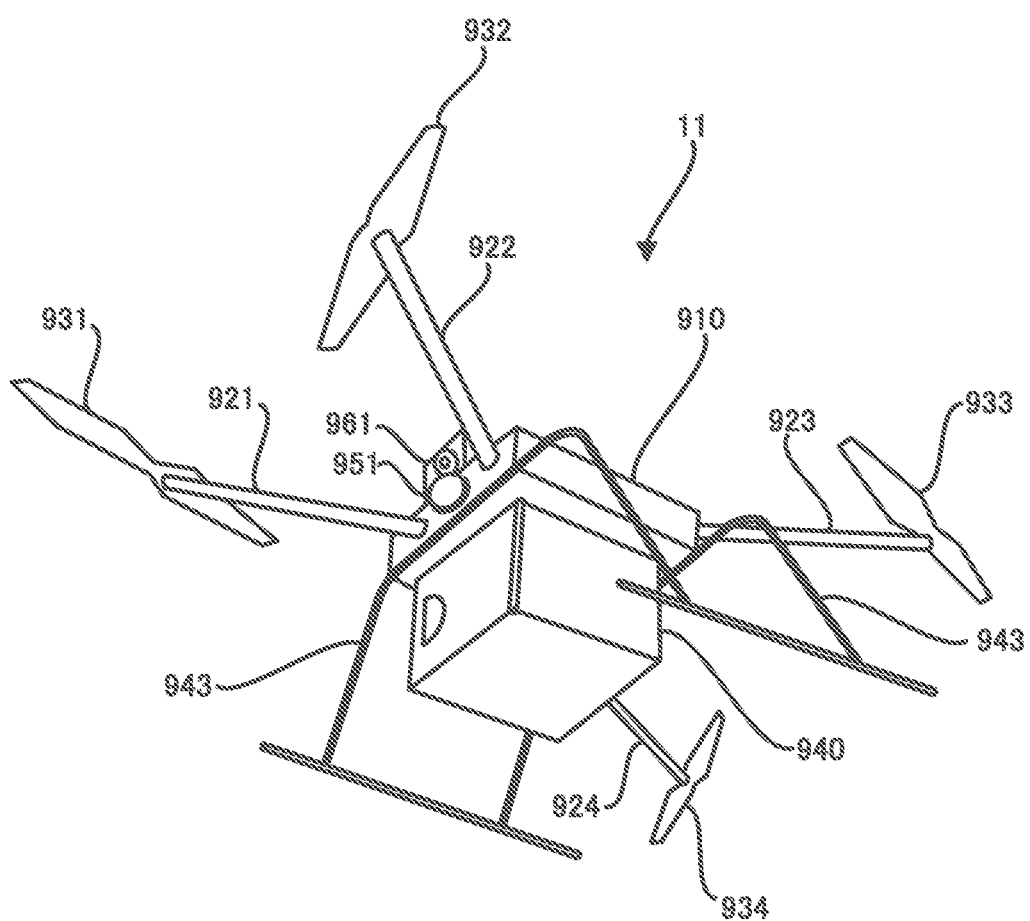
FIG. 26 is an appearance configuration drawing illustrating an example of the appearance of a first transporter according to Modified Example 16 of Embodiment 1.

In Embodiment 1, a description is given in which the distribution system 1 includes the first transporter 11 that is an unmanned ground vehicle that is provided with a non-illustrated robot arm, and a locker device 12 in which an article is stored by the first transporter 11. However, Embodiment 1 is not limited thereto, and the distribution system 1 according to the present modified example includes a first transporter 11 that is an unmanned aircraft such as illustrated in FIG. 26 such as a drone or the like and that is not provided with a robot arm, and a locker device 12 that is provided with a non-illustrated robot arm and that uses the robot arm to store an article transported by the first transporter 11.

The first transporter 11 includes a control device 910 that controls the attitude and flight of the first transporter 11. The first transporter 11 includes propeller arms 921, 922 and 923, 924 that respectively protrude forward to the right and forward to the left from the front face of the control device 910, and backward to the left and backward to the right from the back face of the control device 910. Furthermore, the first transporter 11 includes propellers 931 to 934 that are installed on tips of the propeller arms 921 to 924, and non-illustrated motors that rotate the propellers 931 to 934 in accordance with the control of the control device 910.

A storage cabinet 940 that stores an article is provided on the bottom surface of the control device 910 of the first transporter 11. The storage cabinet 940 includes a box body, a door, a door frame, a deadbolt, and a strike plate that are non-illustrated. The configurations and functions of the box body, the door, the door frame, the deadbolt, and the strike plate of the cabinet 940 are the same as the configurations and functions of the box body, the door 215*a*, the door frame 215*b*, the deadbolt 215*c*, and the strike plate 215*d* of the storage box 215 of the second transporter 21.

The first transporter 11 further includes a support leg 943 that protrudes downward from the bottom surface of the control device 910 and that supports the control device 910. Moreover, the first transporter 11 includes a LiDAR sensor 951 provided on the front surface of the control device 910, and a non-illustrated LiDAR sensor provided on the back surface of the control device 910. The configurations and functions of the LiDAR sensor 951 on the front surface and the LiDAR sensor on the back surface of the first transporter 11 are the same as the configurations and functions of the LiDAR sensor 216 on the front surface and the LiDAR sensor on the back surface of the second transporter 21, respectively.

The first transporter 11 further includes an imaging device 961 for which the optical axis and angle of view are adjusted such that space in front of the first transporter 11 can be imaged. The configuration and the functions of the imaging device 961 of the first transporter 11 are the same as the configuration and the functions of the imaging device 217 of the second transporter 21.

The control device 910 of the first transporter 11 includes, as hardware, a CPU, a RAM, a ROM, a flash memory, a data communication circuit, a video card, a display device, an input device, a position measurement circuit, an input/output port, and a drive circuit that are non-illustrated. The configurations and functions of these hardware of the control device 910 of the first transporter 11 are the same as the configurations and functions of the hardware of the control device 219 of the second transporter 21 illustrated in FIG. 3.

The drive circuit of the first transporter 11 is connected to non-illustrated cables that are respectively connected to the non-illustrated motors that rotate the propellers 931 to 934. The drive circuit drives, in accordance with signals output by the CPU, the non-illustrated motors that rotate the propellers 931 to 934.

When the data communication circuit of the first transporter 11 receives an execution command sent from the information processing device 100, the CPU of the first transporter 11 executes the delivery procedures in accordance with the execution command.

In the present modified example, a description is given in which the distribution system 1 includes the first transporter 11 that is an unmanned aircraft and that is not provided with a robot arm, and the locker device 12 that is provided with a robot arm. Additionally, in the present modified example, a description is given in which the locker device 12 uses the robot arm of the locker device 12 to move the article transported by the first transporter 11 from the first transporter 11 to the locker device 12. However, the present modified example is not limited thereto, and a configuration is possible in which the distribution system 1 includes a first transporter 11 that is an unmanned aircraft and that is provided with a robot arm, and a locker device 12 in which the article is stored by the robot arm of the first transporter 11.

In the present modified example, a description is given in which the distribution system 1 includes the first transporter 11 that is an unmanned aircraft, and the second transporter 21 that is an unmanned ground vehicle. However, the present modified example is not limited thereto. A configuration is possible in which the distribution system 1 includes a first transporter 11 and a second transporter 21 that are unmanned aircrafts.

In the present modified example, a description is given in which the first transporter 11 is implemented as an unmanned aircraft, but the present modified example is not limited thereto, and a configuration is possible in which the first transporter 11 is an unmanned flying object. Furthermore, in the present modified example, a description is given in which the first transporter 11 is implemented as a drone that obtains lift and thrust from the propellers 931 to 934, but the present modified example is not limited thereto. A configuration is possible in which the first transporter 11 includes wings and obtains lift by the wings, or includes an air sac filled with a gas having a lower specific gravity than air and obtains lift by the air sac. Additionally, a configuration is possible in which the first transporter 11 includes a jet engine or a rocket engine, and obtains thrust by the jet engine or the rocket engine.

In Embodiment 1, a description is given in which the locker device 12 is installed at the entrance of the apartment building where the recipient resides. However, Embodiment 1 is not limited thereto, and a configuration is possible in which the locker device 12 is installed on a veranda or a roof of a house, an apartment complex, an office building, a hotel, a commercial facility, or a public facility.

The present modified example and Modified Example 14 of Embodiment 1, in which the first transporter 11 stops at the destination or travels around or travels back and forth in the vicinity of the destination, can be combined. In such a case, a configuration is possible in which the location of the destination where the first transporter 11 lands or the vicinity of the location where the first transporter 11 travels around, travels back and forth, or hovers is the veranda or the roof of a house, an apartment complex, an office building, a hotel, a commercial facility, or a public facility.

Modified Example 17 of Embodiment 1

In Embodiment 1, a description is given in which the first transporter 11 is implemented as an unmanned ground vehicle. However, the first transporter 11 need not be unmanned and, provided that, with the exception of the control by the information processing device 100, the first transporter 11 is an autonomous moving object, a human may ride the first transporter 11.

Modified Example 18 of Embodiment 1

In Embodiment 1, a description is given in which the first transporter 11 is implemented as an unmanned ground vehicle. However, Embodiment 1 is not limited thereto. The first transporter 11 according to the present modified example is implemented as a manned ground vehicle that travels in accordance with the operations of a driver that rides the first transporter 11.

In the present modified example, in the hand over procedure in which an article is handed over from the second transporter 21 to the first transporter 11, the driver of the first transporter 11 touches the article to move that article from the second transporter 21 to the first transporter 11. As such, in the present modified example, a human is involved in the hand over procedure. Therefore, the first transporter 11 may or may not be provided with a robot arm, and may be implemented as an automobile such as a truck, for example.

Moreover, the present modified example is not limited thereto, and a configuration is possible in which, in the hand over procedure, instead of the driver of the first transporter 11, one or more of the robot arm 218 of the second transporter 21 and a non-illustrated robot arm of the first transporter 11 moves the article from the second transporter 21 to the first transporter 11. That is, a configuration is possible in which a human is not involved in the hand over procedure.

In the present modified example, in the transport to locker device procedure, the article is stored in the storage locker of the first transporter 11 and, as such, the driver of the first transporter 11 transports the article to the locker device 12 by driving the first transporter 11 without touching the article. As such, in the present modified example, a human is not involved in the transport to locker device procedure. However, the present modified example is not limited thereto, and a configuration is possible in which if the driver of the first transporter 11 must touch the article in the transport to locker device procedure, a human is involved in the transport to locker device procedure.

Furthermore, in the present modified example, as in Modified Example 14 of Embodiment 1, the distribution system 1 does not include the depository 22. As such, when the first transporter 11 according to the present modified example transports an article to a destination, the first transporter 11 stops at the destination and hands over the article to the recipient in accordance with an operation performed by the recipient, without executing the store in locker device procedure. The recipient receives the article from the storage locker of the first transporter 11.

However, the present modified example is not limited thereto, and a configuration is possible in which, as in Embodiment 1, the distribution system 1 includes the depository 22, and the first transporter 11 executes the store in locker device procedure when the first transporter 11 transports the article to the destination. In such a case, the driver of the first transporter 11 must touch the article to move the article from the first transporter 11 to the locker device 12, and a human may be involved in the store in locker device procedure. Additionally, in such a case, a configuration is possible in which the robot arm of the first transporter 11 moves the article from the first transporter 11 to the locker device 12 without the driver needing to touch the article to move the article from the first transporter 11 to the locker device 12 and, as such, a human is not involved in the store in locker device procedure. Furthermore, in such a case, a configuration is possible in which the locker device 12 is provided with a non-illustrated robot arm and, as such, the driver needs not touch the article, and the robot arm of the locker device 12 moves the article from the first transporter 11 to the locker device 12.

In Embodiment 1, a description is given in which the second transporter 21 is implemented as an unmanned ground vehicle, but Embodiment 1 is not limited thereto, and a configuration is possible in which the second transporter 21 is implemented as a manned ground vehicle that travels in accordance with the operations of a driver that rides the second transporter 21. Furthermore, a configuration is possible in which the driver needs not touch the article in the undertaking procedure in which the article is undertaken from the carrier, the transport to depository procedure, the store in depository procedure, the retrieval procedure in which the article is retrieved from the depository 22, and the transport to first transporter procedure, and a human is not involved in these procedures. In contrast, a configuration is possible in which the driver must touch the article in these procedures, and a human is involved in these procedures.

Modified Example 19 of Embodiment 1

In Embodiment 1, a description is given in which the target amount of elapsed time is preset to an amount of time from when the magnitude of infectivity of a predetermined virus or bacterium is less than or equal to a predetermined magnitude. The predetermined virus or bacterium may respectively be any virus or bacterium. For example, the predetermined virus or bacterium may be severe acute respiratory syndrome (SARS)-Coronavirus (Cov)-2. In such a case, the target amount of elapsed time may be 72 hours, which is when the magnitude of infectivity of SARS-Cov-2 is less than or equal to the predetermined magnitude, or may be shorter or longer than 72 hours.

Additionally, the predetermined virus may, for example, be influenza virus, norovirus, or rotavirus. The predetermined bacterium may be *Escherichia coli* or hemolytic *streptococcus*.

Modified Example 20 of Embodiment 1

The article transported by the first transporter 11 and the second transporter 21 may be any type of article, and may be luggage or cargo. Additionally, the article is not limited to objects and may be a living organism.

Modified Example 21 of Embodiment 1

In Embodiment 1, a description is given in which the first distribution mechanism 10 includes one first transporter 11 and one locker device 12. However, Embodiment 1 is not limited thereto. A configuration is possible in which the first distribution mechanism 10 includes N1 of the first transporter 11, and M1 of the locker device 12 (where N1 and M1 are natural number). Additionally, in Embodiment 1, a description is given in which the second distribution mechanism 20 includes one second transporter 21, and one depository 22. However, Embodiment 1 is not limited thereto. A configuration is possible in which the second distribution mechanism 20 includes N2 of the second transporter 21, and M2 of the depository 22 (where N2 and M2 are natural number).

Modified Example 22 of Embodiment 1

In Embodiment 1, a description is given in which the first transporter 11 transports one article, and stores the transported one article in one storage box of the locker device 12. Additionally, a description is given in which the notifier 140 of the information processing device 100 performs a notification that includes the first time and the recommended receiving start time of the one article stored in the one storage box of the locker device 12, informs that a human has not touched that one article later than the first time, and informs of the recommended receiving start time of that one article.

However, Embodiment 1 is not limited thereto, and a configuration is possible in which the first transporter 11 transports a plurality of articles, and stores the transported plurality of articles in one storage box of the locker device 12. Additionally, a configuration is possible in which the notifier 140 of the information processing device 100 performs a notification that includes the latest first time of the first times of the plurality of articles stored in the one storage box of the locker device 12, and the latest recommended receiving start time of the recommended receiving start times of the plurality of articles. The notification including the latest first time and the latest recommended receiving start time is a notification that informs that a human has not touched any of the plurality of articles later than the latest first time, and that the time at which the receiving is recommended to start for the plurality of articles is the latest recommended receiving start time.

In Embodiment 1, a description is given in which the second transporter 21 stores one article in one storage box 225 of the depository 22, but Embodiment 1 is not limited thereto. A configuration is possible in which the second transporter 21 stores a plurality of articles that have the same second time in the same storage box 225.

Modified Example 23 of Embodiment 1

In Embodiment 1, a description is given in which the information processing device 100 includes the information storage 190, but Embodiment 1 is not limited thereto. The information processing device 100 according to the present modified example does not include the information storage 190. In one example, the information processing device 100 according to the present modified example is connected, via the internet IN, to a non-illustrated information storage device that is a network attached storage (NAS), and that has the same functions as the functions of the information storage 190. The distribution system 1 according to the present modified example may include an information storage or may not include an information storage. The information processing device 100 according to the present modified example uses the information stored in the information storage to execute the pre-sale control processing illustrated in FIG. 12, the second time setting processing illustrated in FIG. 17, the second time updating processing illustrated in FIG. 18, the post-sale control processing illustrated in FIGS. 19A and 19B, the first time setting processing illustrated in FIG. 21, the first time updating processing illustrated in FIG. 22, and the notification processing illustrated in FIG. 23.

Modified Example 24 of Embodiment 1

In Embodiment 1, a description is given in which the terminal device 19 is implemented as a smartphone, but Embodiment 1 is not limited thereto, and a configuration is possible in which the terminal device 19 is implemented as a tablet-type personal computer or a notebook-type personal computer.

Embodiment 2

A description is given in which, when the information processing device 100 according to Embodiment 1 receives a sale request, the information processing device 100 performs control for causing the second transporter 21 to retrieve the sold article from the depository 22 and hand over the article to the first transporter 11 and, then, performs control for causing the first transporter 11 to transport the handed over article to the destination. However, Embodiment 1 is not limited thereto.

When the information processing device 100 according to the present embodiment receives a sale request, the information processing device 100 determines a hand over timing, at which the sold article is handed over from the second transporter 21 to the first transporter 11, such that the target amount of elapsed time elapses from the second time at which a human last contacts the article to the receiving time at which the recipient receives the article. Then, the information processing device 100 performs control of the second transporter 21 so that the hand over is performed at the determined hand over timing and, then, performs control for causing the first transporter 11 to transport the handed over article to the destination. In the following, the configurations that are the same as those in Embodiment 1 are denoted with the same reference numerals used in Embodiment 1, and the description focuses on the differences between the present embodiment and Embodiment 1.

Figure 27A:
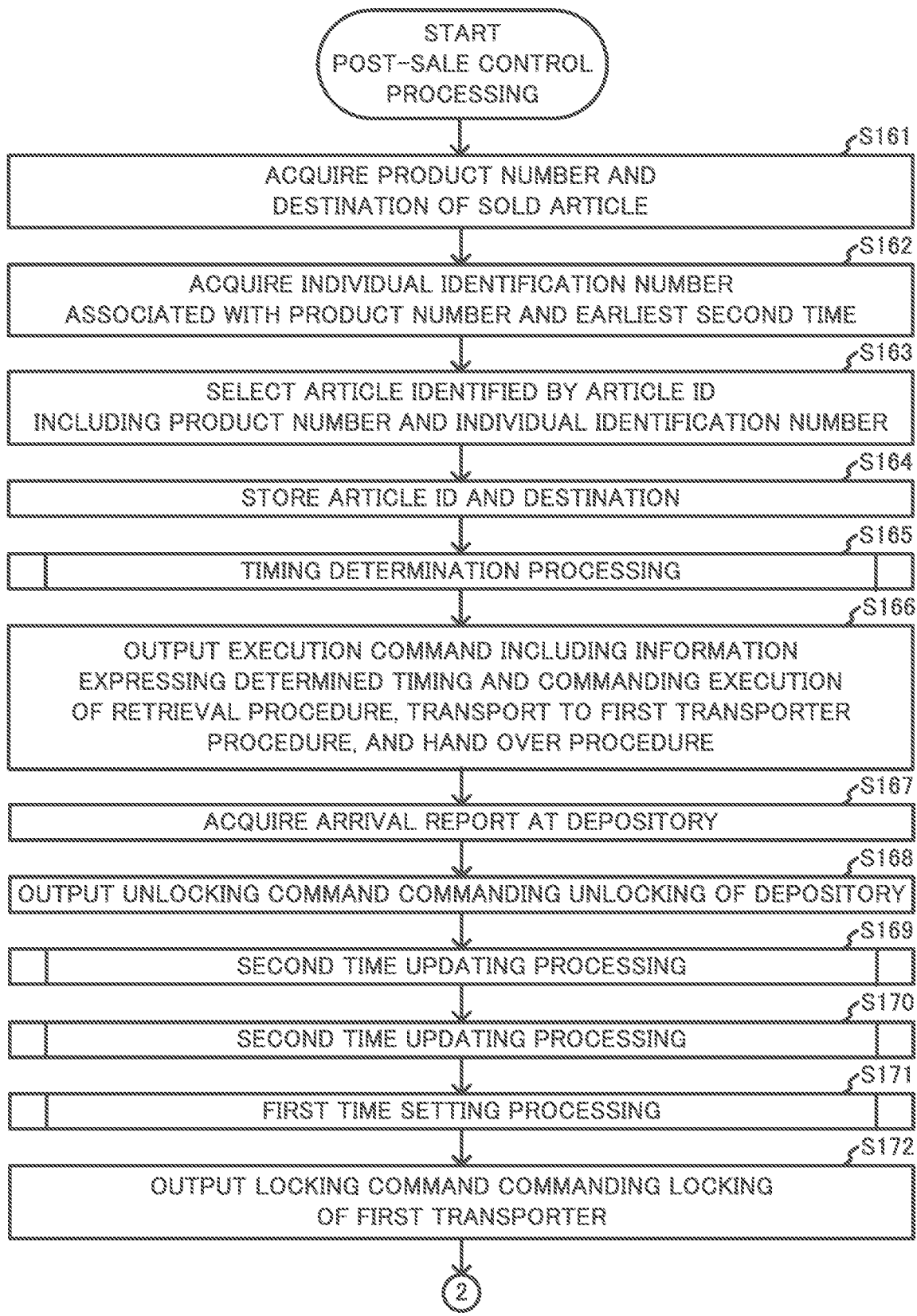
FIGS. 27A and 27B are each flowcharts illustrating an example of post-sale control processing executed by an information processing device according to Embodiment 2.
Figure 27B:
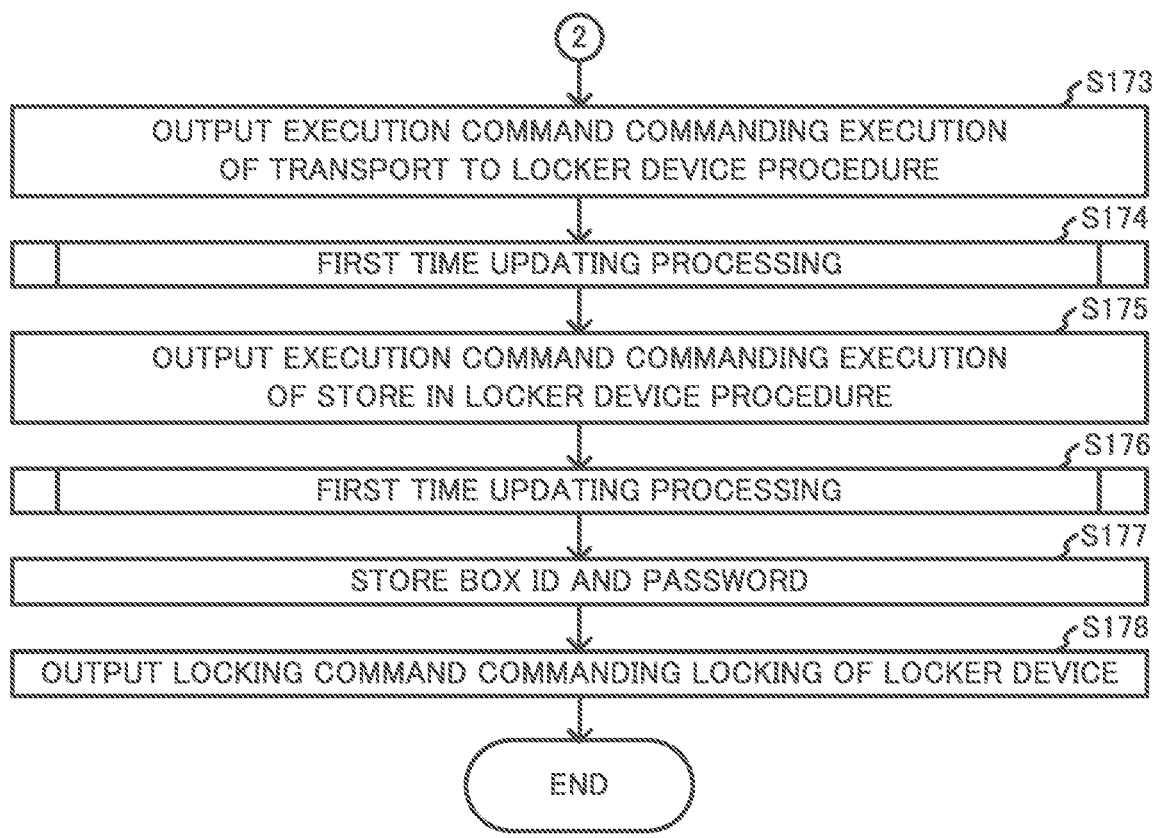
Figure 28:
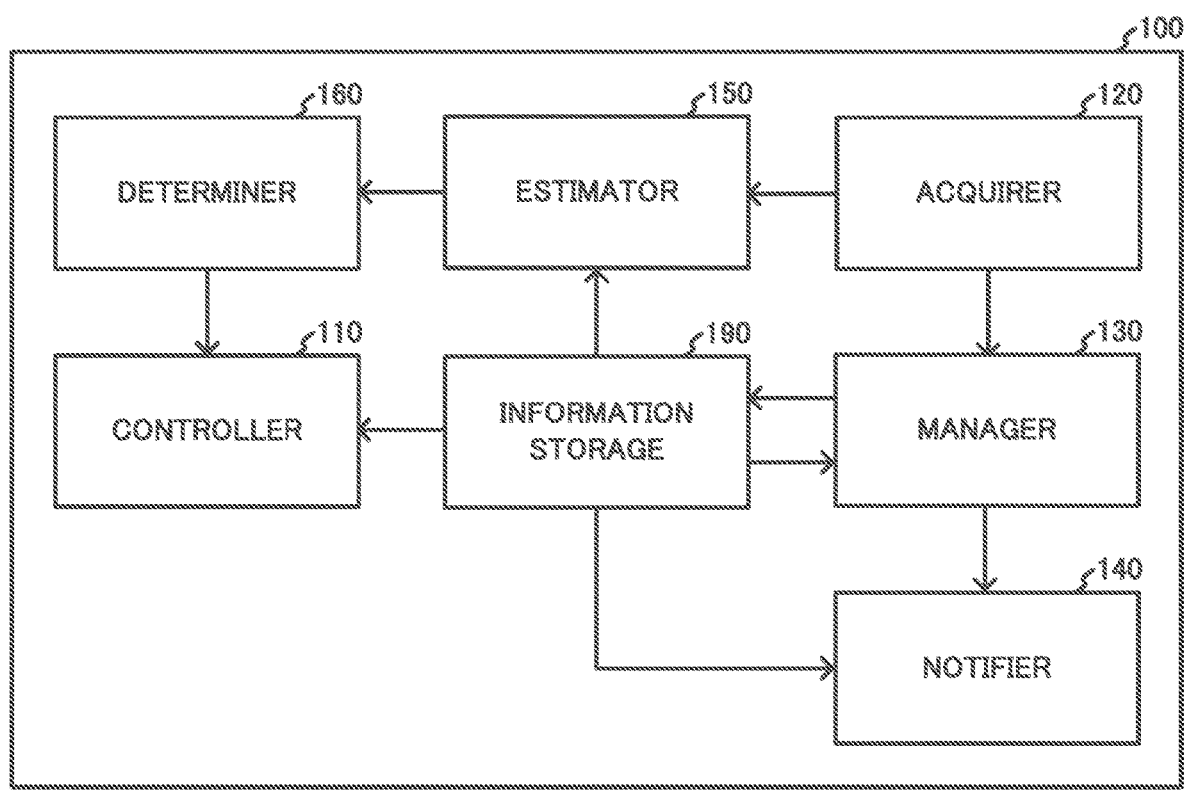
FIG. 28 is a functional block diagram illustrating an example of the functions of the information processing device according to Embodiment 2.

When the first data communication circuit 104a of the information processing device 100 according to the present embodiment receives a sale request, the CPU 101 of the information processing device 100 executes post-sale control processing such as illustrated in FIGS. 27A and 27B. As a result, the CPU 101 of the information processing device 100 functions as an estimator 150 such as illustrated in FIG. 28 that estimates an amount of transport time needed to transport the article from the hand over location, where the hand over of the article is performed, to the destination of that article, and a determiner 160 that determines the hand over timing on the basis of the estimated amount of transport time.

Figure 29:
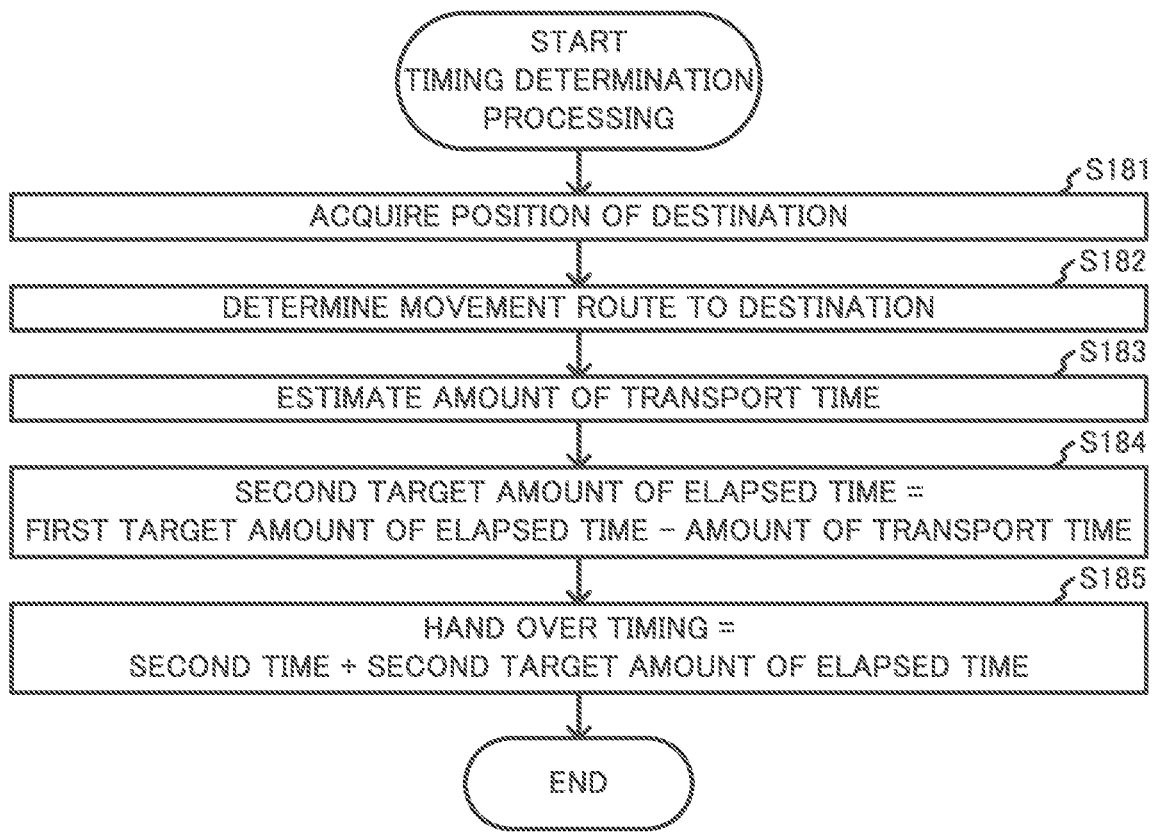
FIG. 29 is a flowchart illustrating an example of timing determination processing executed by the information processing device according to Embodiment 2.

When the execution of the post-sale control processing of FIGS. 27A and 27B starts, the information processing device 100 executes the same processing as steps S91 to S94 of FIG. 19A (steps S161 to S164), and selects an article to be sold. Then, the information processing device 100 executes timing determination processing such as illustrated in FIG. 29 for determining the hand over timing of the article to be sold, with the article ID of the selected article as an argument.

When the execution of the timing determination processing starts, the acquirer 120 of the information processing device 100 acquires the article ID from the argument, and acquires, from the article table of FIG. 20, the information expressing the destination associated with the acquired article ID (step S181). Then, the acquirer 120 acquires information expressing the latitude, longitude, and altitude stored in advance in the information storage 190 in association with the information expressing the address of the destination.

Thereafter, the controller 110 of the information processing device 100 executes the same processing as step S02 of FIG. 4 to determine a movement route from the hand over location where the article is handed over to the first transporter 11 to the destination of that article (step S182).

Next, the acquirer 120 of the information processing device 100 acquires information expressing a movement speed of the first transporter 11 that is stored in advance in the information storage 190. The movement speed of the first transporter 11 may be a predetermined speed, or may be an average speed of movement speeds of the first transporter 11 measured in the past.

Thereafter, the estimator 150 of the information processing device 100 calculates a distance of the determined movement route, and divides the calculated distance by the speed expressed in the acquired information. As a result, the estimator 150 estimates the amount of transport time needed for the first transporter 11 to travel on the movement route to transport the article from the hand over location to the destination (step S183).

Thereafter, the acquirer 120 of the information processing device 100 acquires information expressing the target amount of elapsed time stored in advance in the information storage 190. Next, the determiner 160 calculates, as a second target amount of elapsed time, a time obtained by subtracting the estimated amount of transport time from the first target amount of elapsed time that is the target amount of elapsed time (step S184). Then, the acquirer 120 acquires, from the article table of FIG. 20, the second time associated with the acquired article ID, and the determiner 160 determines, as a hand over time that is the hand over timing, a time obtained by adding the second target amount of elapsed time to the second time (step S185). Then, the determiner 160 ends the execution of the timing determination processing.

In step S165 of FIG. 27A, when the execution of the timing determination processing is ended, the controller 110 of the information processing device 100 generates an execution command that includes information expressing the determined hand over timing, and that commands the execution of the retrieval procedure in which the sold article is retrieved from the depository 22, the transport to first transporter procedure, and the hand over procedure. Then, the controller 110 outputs the generated execution command to the second data communication circuit 104b with the second transporter 21 as the destination (step S166).

The second transporter 21 that receives the execution command determines, on the basis of the hand over timing included in the execution command, a movement start timing at which the second transporter 21 starts movement to the position of the depository 22 in order to retrieve the article from the depository 22. Then, when the determined movement start timing arrives, the second transporter 21 starts moving to the depository 22.

When the information processing device 100 receives an arrival report notifying that the second transporter 21 has arrived at the depository 22, the information processing device 100 executes the same processing as steps S96 and S97 of FIG. 19A (steps S167 and S168) to unlock the depository 22.

Thereafter, the second transporter 21 that has completed the execution of the retrieval procedure sends a completion report notifying that the retrieval procedure is completed and, when the second data communication circuit 104b of the information processing device 100 receives the completion report, the second time updating processing illustrated in FIG. 18 is executed (step S169).

Next, the second transporter 21 sends a completion report after the execution of the transport to first transporter procedure and, when the information processing device 100 receives that completion report, the information processing device 100 executes the second time updating processing again (step S170).

Thereafter, the second transporter 21 executes, at the hand over timing, the hand over procedure in which the article is handed over to the first transporter 11 and, then, sends a completion report. When the information processing device 100 receives that completion report, the information processing device 100 executes the first time setting processing illustrated in FIG. 21 (step S171).

Next, the information processing device 100 executes the same processing as steps S103 to S109 of FIGS. 19A and 19B (steps S172 to S178) to perform control for causing the first transporter 11 to execute the transport to locker device procedure and the store in locker device procedure. As a result, the information processing device 100 performs control for causing the first transporter 11 to complete the transportation of the article to the locker device 12 at the recommended receiving start time that is a time that is the amount of transport time after the hand over timing and that is a time that is the target amount of elapsed time after the first time.

Figure 30:
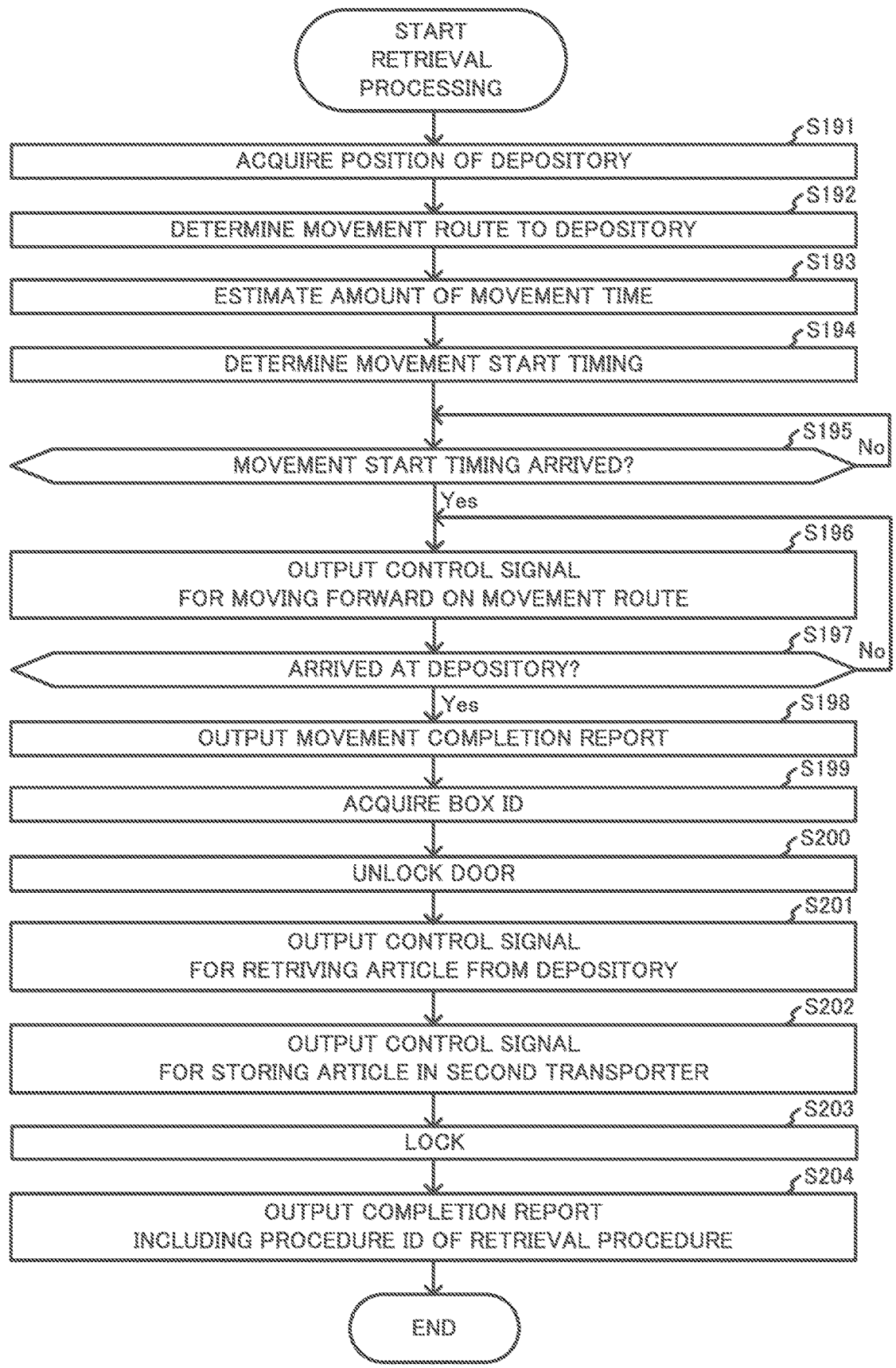
FIG. 30 is a flowchart illustrating an example of retrieval processing executed by a second transporter according to Embodiment 2.

When the data communication circuit of the second transporter 21 according to the present modified example receives the execution command outputted in step S166 of FIG. 27A, the CPU 219a of the second transporter 21 executes retrieval processing such as illustrated in FIG. 30.

When the execution of the retrieval processing starts, the CPU 219a of the second transporter 21 executes the same processing as steps S31 and S32 of FIG. 9 (steps S191 and S192). As a result, the second transporter 21 determines a movement route from the position of the second transporter 21 to the depository 22, and a movement route from the depository 22 to the hand over location.

Next, the CPU 219a of the second transporter 21 executes the same processing as step S183 of FIG. 29 to estimate an amount of movement time from the position of the second transporter 21 to the depository 22, and an amount of movement time from the depository 22 to the hand over location (step S193).

Thereafter, the CPU 219a of the second transporter 21 acquires the execution command from the data communication circuit 219e, and acquires information expressing the hand over timing from the acquired execution command. Then, the CPU 219a of the second transporter 21 acquires information that is stored in advance in the flash memory 219d and that expresses an amount of retrieval time needed to retrieve the article from the depository 22. The amount of retrieval time may, for example, be a predetermined time, or may be an average value of amounts of time that are measured in the past and that are amounts of time needed for the second transporter 21 to retrieve articles from the depository 22.

Additionally, the CPU 219a of the second transporter 21 acquires information that is stored in advance in the flash memory 219d and that expresses an amount of hand over time needed for the second transporter 21 to hand over the article to the first transporter 11. The amount of hand over time may, for example, be a predetermined time, or may be an average value of amounts of time that are measured in the past and that are amounts of time needed for the second transporter 21 to hand over articles.

Next, the CPU 219a of the second transporter 21 calculates the total amount of time of the amount of movement time from the position of the second transporter 21 to the depository 22, the amount of retrieval time, the amount of movement time from the depository 22 to the hand over location, and the amount of hand over time. Then, the CPU 219a of the second transporter 21 determines, as the movement start timing at which the second transporter 21 starts moving to the depository 22, a time that is the calculated total amount of time earlier than the hand over timing expressed in the acquired information (step S194).

The movement start timing is determined on the basis of the total amount of time in this manner because, in the present embodiment, the "hand over timing at which the article is handed over" means the timing at which the hand over is completed. However, the hand over timing is not limited thereto, and a configuration is possible in which the hand over timing means the timing at which the handing over starts, and the CPU 219a of the second transporter 21 calculates the movement start timing on the basis of the total amount of time of the amount of movement time to the depository 22, the amount of retrieval time, and the amount of movement time from the depository 22 to the hand over location. Additionally, a configuration is possible in which the hand over timing means a point in time included in a period in which the hand over is performed.

Thereafter, the CPU 219a of the second transporter 21 acquires the system time from the OS, for example, and determines whether or not the acquired time is a time that is the determined movement start timing, or later (step S195). Here, when the CPU 219a determines that the system time is a time earlier than the movement start timing (step S195; No), the CPU 219a sleeps for a predetermined amount of time such as one minute, for example, and then repeats the processing described above from step S195.

In contrast, when the CPU 219a of the second transporter 21 determines that the system time is the time of the movement start timing, or later (step S195; Yes), the CPU 219a executes the same processing as the processing of steps S33 to S41 of FIG. 9 (steps S196 to S204). As a result, the second transporter 21 starts moving to the depository 22, executes the retrieval procedure and, then, ends the execution of the retrieval processing.

When the execution of the retrieval processing ends, the second transporter 21 executes the non-illustrated transport to first transporter processing described in Embodiment 1 to perform the transport to first transporter procedure. Then, when the execution of the transport to first transporter processing ends, the second transporter 21 executes the hand over processing illustrated in FIG. 10. As a result, the second transporter 21 hands over the article to the first transporter 11 at the hand over timing determined by the information processing device 100. In the present embodiment, the phrase "hands over the article at the hand over timing" means completing the hand over of the article at the hand over timing. However, the present embodiment is not limited thereto, and a configuration is possible in which "hands over the article at the hand over timing" means starting the hand over of the article at the hand over timing, or that the hand over of the article is being performed at the hand over timing.

According to these configurations, the distribution system 1 further includes the determiner 160 that determines, on the basis of the second time, the hand over timing of the article from the second distribution mechanism 20 to the first transporter 11 of the first distribution mechanism 10, such that the target amount of elapsed time elapses from the second time at which a human last contacts the article to the receiving time at which the recipient receives the article. Additionally, according to these configurations, the target amount of elapsed time is an amount of time from when a predetermined virus or bacterium is discharged from the body of a human to when the magnitude of infectivity of that virus or bacterium is less than or equal to a predetermined magnitude. Moreover, the distribution system 1 further includes the controller 110 that performs control for causing the first transporter 11 of the first distribution mechanism 10 to transport the article to the destination at a time that is the target amount of elapsed time after the first time. As such, even if a virus or bacterium is adhered to the article due to contact with a human, since the article is transported to the destination after the target amount of elapsed time has elapsed from when the article was last contacted by a human, the distribution system 1 can reliably suppress the recipient that receives the article at the destination from becoming infected with that virus or bacterium.

Furthermore, according to these configurations, the distribution system 1 further includes the estimator 150 that estimates, on the basis of the destination, the amount of transport time needed for the first transporter 11 of the first distribution mechanism 10 to transport the article to the destination. Additionally, the determiner 160 calculates the second target amount of elapsed time that is the estimated amount of transport time shorter than the first target amount of elapsed time that is the target amount of elapsed time, and determines, as the hand over timing, the timing of a time that is the second target amount of elapsed time after the second time. As such, the distribution system 1 can determine the hand over timing such that the article is delivered to the destination at a time that is the target amount of elapsed time after the second time. Therefore, when the recipient receives the article from the first transporter 11, even if a virus or bacterium is adhered to the article due to contact with a human, the distribution system 1 can suppress the recipient from becoming infected with that virus or bacterium and, also, can shorten the amount of time that the first transporter 11 is stopped at the destination, thereby improving the transport efficiency of the article by the first transporter 11. In one example, the transport efficiency by the first transporter 11 is expressed by the number of articles that the first transporter 11 transports per unit time, but is not limited thereto. Furthermore, in a case in which the first transporter 11 moves the article to the locker device 12 and the recipient receives the article from the locker device 12, the distribution system 1 can suppress infection and, also shorten the amount of time that the locker device 12 stores the article, thereby improving the storage efficiency of the locker device 12. In one example, the storage efficiency of the locker device 12 is expressed as the number of articles that the locker device 12 stores per unit time, but is not limited thereto.

Modified Example 1 of Embodiment 2

In Embodiment 2, a description is given in which the determiner 160 of the information processing device 100 determines, as the hand over timing, a time obtained by adding the second target amount of elapsed time to the second time. However, Embodiment 2 is not limited thereto. A configuration is possible in which the determiner 160 of the information processing device 100 determines, as the hand over timing, a time at or after the time obtained by adding the second target amount of elapsed time to the second time.

Modified Example 2 of Embodiment 2

In Embodiment 2, a description is given in which the determiner 160 of the information processing device 100 determines the hand over timing, but Embodiment 2 is not limited thereto. The determiner 160 according to the present modified example determines a movement start timing at which the second transporter 21 starts moving to the depository 22 to retrieve the article.

When the execution of the post-sale control processing of FIGS. 27A and 27B starts, the information processing device 100 according to the present modified example executes the processing of steps S161 to S164 (steps S161 to S164), and selects an article to be sold.

Thereafter, the information processing device 100 executes the same processing as the processing of steps S191 to S194 of FIG. 30 to determine the movement start timing (step S165).

Thereafter, the acquirer 120 of the information processing device 100 acquires the system time from the OS, for example, and the controller 110 executes processing for determining whether or not the acquired system time is the movement start timing or later. Here, when the controller 110 determines that the system time is a time earlier than the movement start timing, the controller 110 sleeps for a predetermined amount of time and, then, repeats the processing described above from the processing for determining whether or not the system time is the movement start timing or later.

In contrast, when the controller 110 of the information processing device 100 determines that the system time is a time that is the movement start timing or later, the controller 110 outputs, to the second data communication circuit 104b with the second transporter 21 as the destination, execution commands commanding the execution of the retrieval procedure, the transport to first transporter procedure, and the hand over procedure.

Thereafter, the information processing device 100 executes the processing of steps S167 to S178 of FIGS. 27A and 27B (steps S167 to S178). As a result, as in Embodiment 2, the information processing device 100 performs control for causing the first transporter 11 to complete the transportation of the article to the locker device 12 at the recommended receiving start time that is a time that is the amount of transport time after the hand over timing and that is a time that is the target amount of elapsed time after the first time. Then, the information processing device 100 ends the execution of the post-sale control processing.

Modified Example 3 of Embodiment 2

In Embodiment 2, a description is given in which the determiner 160 of the information processing device 100 determines the hand over timing on the basis of the second time, but Embodiment 2 is not limited thereto. The determiner 160 of the information processing device 100 according to the present modified example determines the hand over timing on the basis of the second time of the sold article and a type of the article.

A product number table such as illustrated in FIG. 31 is stored in advance in the information storage 190 according to the present modified example. Information related to the product number of the article is stored in the product number table. A plurality of records is stored in the product number table. A product number, and a type ID identifying the type of the article to which that product number is assigned are associated and stored in advance in each record. In the present modified example, the type of the article is a type determined by the material of a surface member of the article, but is not limited thereto. Examples of the material of the surface member include glass, plastic, paper, and metal, but are not limited thereto. Examples of the type determined by the material of the surface member include glass product, plastic product, paper product, and metal product, but are not limited thereto.

Additionally, a type table such as illustrated in FIG. 32 is stored in advance in the information storage 190 according to the present modified example. Information related to the type of the article is stored in the type table. A plurality of records is stored in the type table. The type ID identifying the type, and a correction coefficient for the target amount of elapsed time that is used to determine the recommended receiving start time of articles of that type are associated and stored in advance in each record. The type ID and the correction coefficient are associated in advance because the rate at which the infectivity of a virus or bacterium decreases is dependent on the type of material to which that virus or bacterium is adhered.

Figure 33:
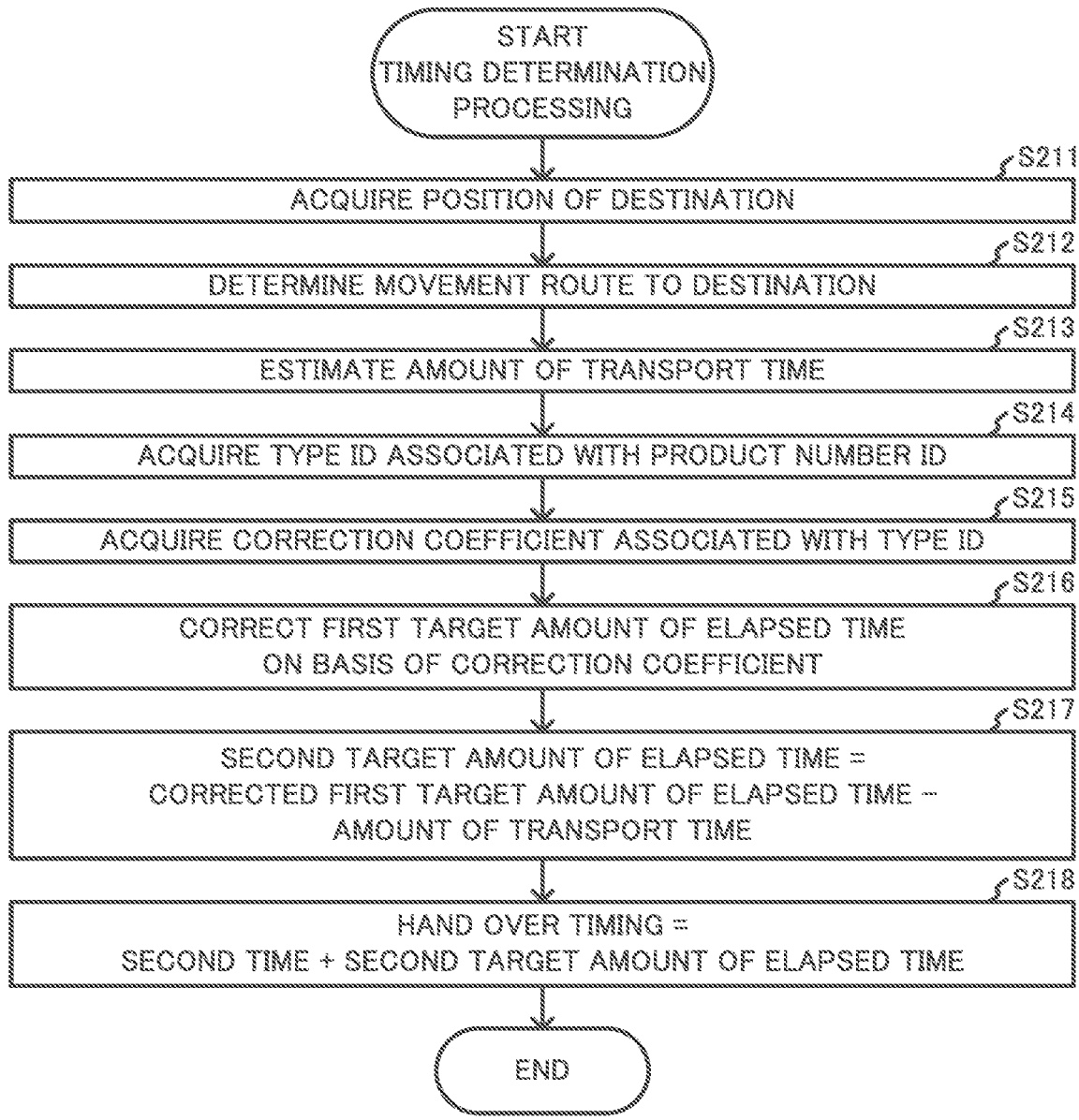
FIG. 33 is a flowchart illustrating an example of timing determination processing executed by the information processing device according to Modified Example 3 of Embodiment 2.

The information processing device 100 according to the present modified example uses the tables illustrated in FIGS. 31 and 32 to execute timing determination processing such as illustrated in FIG. 33. When the execution of the timing determination processing starts, the information processing device 100 executes the same processing as the processing of steps S181 to S183 of FIG. 29 (steps S211 to S213) to estimate the amount of transport time needed to transport the article from the hand over location to the destination.

Thereafter, the acquirer 120 of the information processing device 100 acquires, from the product number table of FIG. 31, the type ID associated with the product number included in the article ID of the sold article (step S214). Next, the acquirer 120 acquires, from the type table of FIG. 32, the correction coefficient associated with the acquired type ID (step S215). As a result, the acquirer 120 acquires the correction coefficient corresponding to the type of the surface member of the sold article.

Thereafter, the acquirer 120 of the information processing device 100 acquires information expressing the first target amount of elapsed time stored in advance in the information storage 190. Next, the determiner 160 multiplies the first target amount of elapsed time by the correction coefficient acquired in step S215 to correct the first target amount of elapsed time (step S216).

Thereafter, the determiner 160 of the information processing device 100 calculates, as the second target amount of elapsed time, an amount of time obtained by subtracting the amount of transport time estimated in step S213 from the corrected first target amount of elapsed time (step S217).

Next, the acquirer 120 of the information processing device 100 acquires, from the article table of FIG. 20, the second time associated with the article ID of the sold article, and the determiner 160 adds the second target amount of elapsed time calculated in step S217 to the second time to determine the hand over timing (step S218). Then, the determiner 160 ends the execution of the timing determination processing.

According to these configurations, the determiner 160 of the distribution system 1 determines the hand over timing on the basis of the second time and the type of the article. Since the rate at which the infectivity of a virus or bacterium decreases is dependent on the type of material to which that virus or bacterium is adhered, even if a virus or bacterium is adhered to the article due to contact with a human, it is possible to more reliably suppress the recipient of the article from becoming infected with that virus or bacterium than in cases in which the hand over timing is determined on the basis of the second time only, for example.

Modified Example 4 of Embodiment 2

In Modified Example 3 of Embodiment 2, a description is given in which the determiner 160 of the information processing device 100 determines the hand over timing on the basis of the second time of the sold article and the type of the article. However, Embodiment 2 is not limited thereto, and the determiner 160 of the information processing device 100 according to the present modified example determines the hand over timing on the basis of the second time of the sold article, and a type of packaging member in which the article is packaged.

To realize this, the product number and a type ID identifying a type of the packaging member of the article to which that product number is assigned are associated and stored in advance in each record of the product number table according to the present modified example. Examples of the packaging member include a glass case, a plastic case, cardboard, and a vinyl bag, but are not limited thereto. Additionally, in the present modified example, the type of the packaging member is a type determined by the material of the packaging member, but is not limited thereto. Examples of the material of the packaging member include glass, plastic, paper or cardboard, vinyl, and metal, but are not limited thereto. Examples of the type determined by the material of the packaging member include glass packaging, plastic packaging, paper packaging, vinyl packaging, and metal packaging, but are not limited thereto.

Modified Example 5 of Embodiment 2

Modified Example 3 of Embodiment 2 in which the hand over timing is determined on the basis of the second time of a sold article and the type of that article, and Modified Example 4 of Embodiment 2 in which the hand over timing is determined on the basis of the second time of the sold article and the type of the packaging member of that article can be combined. The determiner 160 of the information processing device 100 according to the present modified example that is a combination of Modified Example 3 of Embodiment 2 and Modified Example 4 of Embodiment 2 determines a first candidate for the hand over timing on the basis of the second time of the article and the type of that article, and determines a second candidate for the hand over timing on the basis of the second time of the article and the type of the packaging member of that article. Then, the determiner 160 adopts the later candidate of the first candidate and the second candidate, and determines the adopted candidate as the hand over timing.

Modified Example 6 of Embodiment 2

In Modified Example 3 of Embodiment 2, a description is given in which the determiner 160 of the information processing device 100 determines the hand over timing on the basis of the second time and the type of the article, but Embodiment 2 is not limited thereto. The determiner 160 of the information processing device 100 according to the present modified example determines the hand over timing on the basis of the second time of the sold article, and an environment of that article from the second time to when the article is handed over to the first transporter 11.

To realize this, the distribution system 1 according to the present modified example includes a non-illustrated environment sensor that, from the second time until when the article is handed over to the first transporter 11, measures the environment of the second distribution mechanism 20 that stores or transports the article. In the present modified example, the second distribution mechanism 20 is installed at a warehouse of the carrier, and the environment of the second distribution mechanism 20 includes the air temperature of the second distribution mechanism 20. As such, the environment sensor is installed at a position where it is possible to measure the air temperature of the warehouse.

Additionally, the article is stored and kept inside the storage box 225 of the depository 22 from after being undertaken from the carrier until being sold. As such, in the present modified example, the environment sensor is installed inside the storage box 225 of the depository 22 that is installed in the warehouse, and measures the air temperature inside the storage box 225. To realize this, in one example, the environment sensor is implemented as an integrated circuit (IC) temperature sensor, is connected to the information processing device 100, and outputs, to the information processing device 100, a signal expressing the measured temperature inside the storage box 225.

An environment table such as illustrated in FIG. 34 is stored in advance in the information storage 190 according to the present modified example. Information related to the environment is stored in the environment table. A plurality of records is stored in advance in the environment table. Information expressing a predetermined temperature range, and a correction coefficient for the target amount of elapsed time that is used to determine the recommended receiving start time of articles stored at the location of the temperature included in that temperature range are associated and stored in advance in each record. The information expressing the temperature range and the correction coefficient are associated in advance because the rate at which the infectivity of a virus or bacterium decreases is dependent on the temperature at the location where that virus or bacterium is adhered.

The information processing device 100 according to the present modified example uses the table illustrated in FIG. 34 to execute timing determination processing such as illustrated in FIG. 35. When the execution of the timing determination processing starts, the information processing device 100 executes the same processing as the processing of steps S211 to S213 of FIG. 33 (steps S221 to S223) to estimate the amount of transport time.

Next, the acquirer 120 of the information processing device 100 acquires the information expressing the first target amount of elapsed time that is stored in advance in the information storage 190, and the determiner 160 calculates, as the second target amount of elapsed time, an amount of time obtained by subtracting the amount of transport time estimated in step S223 from the first target amount of elapsed time expressed in the acquired information (step S224).

Thereafter, the acquirer 120 of the information processing device 100 acquires, on the basis of a signal output from the non-illustrated environment sensor, information expressing the air temperature inside the depository 22 (step S225). Next, the acquirer 120 acquires the correction coefficient on the basis of the acquired air temperature. To realize this, the acquirer 120 acquires, from the environment table of FIG. 34, the correction coefficient associated with the information expressing the range that includes the temperature expressed in the acquired information (step S226).

Thereafter, the acquirer 120 of the information processing device 100 multiplies the calculated second target amount of elapsed time by the correction coefficient acquired in step S226 to correct the second target amount of elapsed time on the basis of the correction coefficient (step S227).

Next, the determiner 160 of the information processing device 100 executes the same processing as the processing of step S218 of FIG. 33 to determine the hand over timing on the basis of the second time and the corrected second target amount of elapsed time (step S228) and, then, ends the execution of the timing determination processing.

According to these configurations, the determiner 160 of the distribution system 1 determines the hand over timing on the basis of the environment of the article from the second time at which a human last contacted the article to when the article is handed over to the first transporter 11, and the second time. Since the rate at which the infectivity of a virus or bacterium decreases is dependent on the environment of the location where the virus or bacterium is adhered, even if a virus or bacterium is adhered to the article due to contact with a human, it is possible to more reliably suppress the recipient of the article from becoming infected with that virus or bacterium than in cases in which the hand over timing is determined on the basis of the second time only, for example.

Modified Example 7 of Embodiment 2

In Modified Example 6 of Embodiment 2, a description is given in which the determiner 160 of the information processing device 100 determines the hand over timing on the basis of the second time of the sold article, and the air temperature inside the depository 22 in which that article is stored from the second time to when that article is handed over to the first transporter 11. However, Embodiment 2 is not limited thereto. The determiner 160 of the information processing device 100 according to the present modified example determines the hand over timing on the basis of the second time of the article, and the humidity or illuminance inside the depository 22 in which that article is stored from the second time until when that article is handed over to the first transporter 11.

The environment sensor according to the present embodiment is an electric hygrometer that measures the humidity or an electric illuminance meter that measures the illuminance inside the storage box 225 of the depository 22.

Information expressing a predetermined range of the humidity or the illuminance, and a correction coefficient for articles stored at locations of the humidity or the illuminance included in that range are associated and stored in advance in each record of the environment table according to the present modified example. The correction coefficient for the articles is a correction coefficient for the target amount of elapsed time that is used to determine the recommended receiving start time of such articles. The information expressing the range of the humidity or the illuminance, and the correction coefficient are associated in advance because the rate at which the infectivity of a virus or bacterium decreases is dependent on the humidity or the illuminance at the location where that virus or bacterium is adhered.

Modified Example 8 of Embodiment 2

Each of Modified Examples 3 to 7 of Embodiment 2 can be combined. As such, the determiner 160 of the information processing device 100 according to the present modified example that is a combination of Modified Examples 3 to 7 of Embodiment 2 determines the hand over timing on the basis of at least one of the second time of a sold article, the type of that article, the type of the packaging member of that article, or the environment of that article that includes at least one of the air temperature, the humidity or the illuminance from the second time at which a human last contacted the article to the receiving time at which the recipient receives the article.

Modified Example 9 of Embodiment 2

Modified Example 7 of Embodiment 1 in which the first amount of elapsed time and the second amount of elapsed time are managed, and Embodiment 2 can be combined. The determiner 160 of the information processing device 100 according to the present modified example that is a combination of Modified Example 7 of Embodiment 1 and Embodiment 2 determines the hand over timing on the basis of the second amount of elapsed time of the sold article.

To realize this, in step S185 of FIG. 29, the acquirer 120 of the information processing device 100 according to the present modified example acquires, from the non-illustrated second amount of elapsed time table, the thread ID associated with the article ID of the sold article. Next, the acquirer 120 acquires the second amount of elapsed time by referencing the value of the counter used in the timekeeping program executed in the thread identified by the thread ID.

Thereafter, the acquirer 120 of the information processing device 100 acquires the system time from the OS, for example. Next, the determiner 160 of the information processing device 100 determines, as the hand over time that is the hand over timing, a time that is the amount of elapsed time, obtained by subtracting the acquired second amount of elapsed time from the second target amount of elapsed time, after the system time. That is, the determiner 160 determines, as the hand over timing, the time at which the second amount of elapsed time is the second target amount of elapsed time.

Modified Example 10 of Embodiment 2

In Modified Example 9 of Embodiment 2, a description is given in which the determiner 160 of the information processing device 100 determines, as the hand over timing, the time at which the second amount of elapsed time is the second target amount of elapsed time. However, Embodiment 2 is not limited thereto. A configuration is possible in which the determiner 160 of the information processing device 100 determines, as the hand over timing, a time at which the second amount of elapsed time is the second target amount of elapsed time, or later.

Embodiment 1, Modified Examples 1 to 24 of Embodiment 1, Embodiment 2, and Modified Examples 1 to 10 of Embodiment 2 can each be combined with each other. It is possible to provide an information processing device 100 that includes configurations for realizing the functions according to any of Embodiment 1, Modified Examples 1 to 24 of Embodiment 1, Embodiment 2, and Modified Examples 1 to 10 of Embodiment 2. Moreover, it is possible to provide a system that includes a plurality of devices that includes, as an overall system, configurations for realizing the functions according to any of Embodiment 1, Modified Examples 1 to 24 of Embodiment 1, Embodiment 2, and Modified Examples 1 to 10 of Embodiment 2.

Additionally, by applying a program, an existing control device can be made to function as the information processing device 100 according to any of Embodiment 1, Modified Examples 1 to 24 of Embodiment 1, Embodiment 2, and Modified Examples 1 to 10 of Embodiment 2. That is, by applying a program for realizing the various functional configurations of the information processing device 100 described in any of Embodiment 1, Modified Examples 1 to 24 of Embodiment 1, Embodiment 2, and Modified Examples 1 to 10 of Embodiment 2 so as to be executable by a computer (CPU or the like) that controls an existing control device, that existing control device can be caused to function as the information processing device 100 according to any of Embodiment 1, Modified Examples 1 to 24 of Embodiment 1, Embodiment 2, and Modified Examples 1 to 10 of Embodiment 2.

Any distribution method of such a program can be used. For example, the program can be stored and distributed on a recording medium such as a memory card, a compact disc read-only memory (CD-ROM), or a digital versatile disk read-only memory (DVD-ROM), or can be distributed via a communication medium such as the internet. Additionally, the method according to the present disclosure can be implemented using the information processing device 100 according to any of Embodiment 1, Modified Examples 1 to 24 of Embodiment 1, Embodiment 2, and Modified Examples 1 to 10 of Embodiment 2, and the distribution system 1 according to any of Embodiment 1, Modified Examples 1 to 24 of Embodiment 1, Embodiment 2, and Modified Examples 1 to 10 of Embodiment 2.

Preferred embodiments of the present disclosure have been described, but the present disclosure should not be construed as being limited to these specific embodiments. Various modifications and changes may be made within the broader spirit and scope of the invention as set forth in the claims.

APPENDICES

Appendix 1

A distribution system characterized by including:
a first distribution mechanism that includes a transporter that transports an article to a destination of the article; and
a manager that manages a first time that is a time earlier than a receiving time at which the article transported by the transporter is received and that is a last time at which a human contacted the article, or manages a first amount of elapsed time that is an amount of elapsed time from the first time.

Appendix 2

The distribution system according to appendix 1, characterized in that when a human is involved in a hand over of the article to the transporter, the manager manages, as the first time, a time at which the hand over is performed, or manages, as the first amount of elapsed time, an amount of elapsed time from the time at which the hand over is performed.

Appendix 3

The distribution system according to appendix 2, characterized in that when a human is not involved in the hand over of the article to the transporter, the manager manages, as the first time, a time at which a human last contacted the article prior to the hand over being performed, or manages, as the first amount of elapsed time, an amount of elapsed time from the time at which a human last contacted the article prior to the hand over being performed.

Appendix 4

The distribution system according to any one of appendices 1 to 3, characterized by further including:
a notifier that performs, based on the first time or the first amount of elapsed time, a notification to a recipient of the article.

Appendix 5

The distribution system according to appendix 4, characterized in that the notification informs that a human has not contacted the article later than the first time, or a human has not contacted the article throughout the first amount of elapsed time.

Appendix 6

The distribution system according to appendix 4 or 5, characterized in that the notifier further performs, at a time that is a target amount of elapsed time after the first time, or later, or at a time at which the first amount of elapsed time is the target amount of elapsed time, or later, a notification informing that the target amount of elapsed time has elapsed since a human last contacted the article.

Appendix 7

The distribution system according to any one of appendices 1 to 6, characterized in that
the first distribution mechanism further includes a locker device that stores the article, and
at least one of the transporter or the locker device moves the article from the transporter to the locker device.

Appendix 8

The distribution system according to any one of appendices 1 to 7, characterized by further including:

a second distribution mechanism that is a mechanism different than the first distribution mechanism and that transports or stores the article, wherein the manager further manages a second time that is a time earlier than a hand over time at which the second distribution mechanism hands over the article to the first distribution mechanism, and is a last time at which a human contacted the article that is transported or stored by the second distribution mechanism, or manages a second amount of elapsed time that is an amount of elapsed time from the second time.

Appendix 9

The distribution system according to appendix 8, characterized in that when a human is not involved in the hand over of the article from the second distribution mechanism to the first distribution mechanism, the manager manages the second time as the first time, or manages the second amount of elapsed time as the first amount of elapsed time.

Appendix 10

The distribution system according to appendix 9, characterized by further including:
a determiner that determines, based on the second time or the second amount of elapsed time, a hand over timing of the article from the second distribution mechanism to the transporter of the first distribution mechanism such that a target amount of elapsed time elapses from the second time at which a human last contacted the article to the receiving time at which the article is received.

Appendix 11

The distribution system according to appendix 10, characterized by further including:
an estimator that estimates, based on the destination, an amount of transport time needed for the transporter of the first distribution mechanism to transport the article to the destination, wherein
the determiner
calculates a second target amount of elapsed time that is the estimated amount of transport time shorter than a first target amount of elapsed time that is the target amount of elapsed time, and
determines, as the hand over timing, a timing at or later than a time that is the second amount of elapsed time later than the second time, or a time at which the second target amount of elapsed time is the second target amount of elapsed time.

Appendix 12

The distribution system according to appendix 10 or 11, characterized in that the determiner determines the hand over timing based further on at least one of a type of the article, a type of a packaging member in which the article is packaged, or an environment of the article from the second time at which a human last contacted the article to when the article is handed over to the transporter.

Appendix 13

The distribution system according to appendix 6, characterized in that the target amount of elapsed time is an amount of time from when a predetermined virus or a predetermined bacterium is discharged from a body of a human to when a magnitude of infectivity of the virus or the bacterium is less than or equal to a predetermined magnitude, and the notifier performs the notification informing of a recommended receiving start time at which receiving of the article is recommended to start, the recommended receiving start time being a time the target amount of elapsed time later than the first time or a time later than the time.

Appendix 14

The distribution system according to appendix 6, characterized in that the target amount of elapsed time is an amount of time from when a predetermined virus or a predetermined bacterium is discharged from a body of a human to when a magnitude of infectivity of the virus or the bacterium is less than or equal to a predetermined magnitude, and the distribution system further includes a controller that performs control for causing the transporter of the first distribution mechanism to complete transportation of the article to the destination at a time that is the target amount of elapsed time after the first time, or later, or at a time at which the first amount of elapsed time is the target amount of elapsed time, or later.

Appendix 15

The distribution system according to appendix 6, characterized in that the target amount of elapsed time is an amount of time from when a predetermined virus or a predetermined bacterium is discharged from a body of a human to when a magnitude of infectivity of the virus or the bacterium is less than or equal to a predetermined magnitude, and the distribution system further includes the controller that performs control for causing the transporter of the first distribution mechanism to transport the article to a locker device installed at the destination and, then control for unlocking the locked locker device storing the transported article at a time that is the target amount of elapsed time after the first time, or later, or at a time at which the first amount of elapsed time is the target amount of elapsed time, or later.

Appendix 16

The distribution system according to any one of appendices 1 to 15, characterized by further including:
an acquirer that acquires procedure identification information identifying a procedure that is a procedure related to a delivery of the article and that is performed on the article, wherein
when, in a storage in which the procedure identification information identifying the procedure and information expressing whether or not a human is involved in the procedure are associated and stored in plurality, the information associated with the acquired procedure identification information expresses that a human is involved, the manager manages, as the first time, an acquisition time at which the procedure identification information is acquired, or manages, as the first amount of elapsed time, an amount of elapsed time from the acquisition time.

Appendix 17

An information processing device characterized by including:
a controller that performs control for causing a first distribution mechanism including a transporter to transport an article to a destination of the article; and
a manager that manages a first time that is a time earlier than a receiving time at which the article transported by the transporter is received and that is a last time at which a human contacted the article, or manages a first amount of elapsed time that is an amount of elapsed time from the first time.

Appendix 18

A method characterized by including:
managing, by a distribution system including a first distribution mechanism that includes a transporter that transports an article to a destination of the article, a first time that is a time earlier than a receiving time at which the article transported by the transporter is received and that is a last time at which a human contacted the article, or managing a first amount of elapsed time that is an amount of elapsed time from the first time.

Appendix 19

A distribution system characterized by including:
an acquirer that acquires a first time that is a time earlier than a receiving time at which an article is received and that is a last time when a human contacted the article, or acquires a first amount of elapsed time that is an amount of elapsed time from the first time; and
a transporter that transports the article to a destination at a time is a target amount of elapsed time after the acquired first time, or later, or at a time at which the first amount of elapsed time is the target amount of elapsed time, or later.

REFERENCE SIGNS LIST

1 Distribution system
10 First distribution mechanism
11 First transporter
12 Locker device
19 Terminal device
20 Second distribution mechanism
21 Second transporter
22 Depository
100 Information processing device
101, 191, 219a CPU
102, 192, 219b RAM
103a, 193a, 219c ROM
103b, 193b, 219d Flash memory
104a First data communication circuit
104b Second data communication circuit
105a, 195a, 219f Video card
105b, 195b, 219g Display device
105c, 195c, 219h Input device
110 Controller
120 Acquirer
130 Manager
140 Notifier
150 Estimator
160 Determiner
190 Information storage
196, 219i Position measurement circuit
199a Speaker
199b Microphone
194a, 219e Data communication circuit
194b Voice communication circuit
211, 212 Wheel
213 Chassis
214, 940 Storage cabinet
215, 225 Storage box
215a Door
215b Door frame
215c Deadbolt
215d Strike plate
216, 951 LiDAR sensor
217, 218b, 961 Imaging device
218 Robot arm
218a Gripper
218c Arm
219, 229, 910 Control device
219j Input/output port
219k Drive circuit
921 to 924 Propeller arm
931 to 934 Propeller
943 Support leg
LN Local area network
IN Internet

The invention claimed is:
1. A distribution system characterized by comprising:
a first distribution mechanism that includes a transporter that transports an article to a destination of the article; and
a manager that manages a first time that is a time earlier than a receiving time at which the article transported by the transporter is received and that is a last time at which a human contacted the article, or manages a first amount of elapsed time that is an amount of elapsed time from the first time.
2. The distribution system according to claim 1, characterized in that when a human is involved in a hand over of the article to the transporter, the manager manages, as the first time, a time at which the hand over is performed, or manages, as the first amount of elapsed time, an amount of elapsed time from the time at which the hand over is performed.
3. The distribution system according to claim 2, characterized in that when a human is not involved in the hand over of the article to the transporter, the manager manages, as the first time, a time at which a human last contacted the article prior to the hand over being performed, or manages, as the first amount of elapsed time, an amount of elapsed time from the time at which a human last contacted the article prior to the hand over being performed.
4. The distribution system according to claim 1, characterized by further comprising:
a notifier that performs, based on the first time or the first amount of elapsed time, a notification to a recipient of the article.
5. The distribution system according to claim 4, characterized in that the notification informs that a human has not contacted the article later than the first time, or a human has not contacted the article throughout the first amount of elapsed time.

6. The distribution system according to claim 4, characterized in that the notifier further performs, at a time that is a target amount of elapsed time after the first time, or later, or at a time at which the first amount of elapsed time is the target amount of elapsed time, or later, a notification informing that the target amount of elapsed time has elapsed since a human last contacted the article.

7. The distribution system according to claim 1, characterized in that
the first distribution mechanism further includes a locker device that stores the article, and
at least one of the transporter or the locker device moves the article from the transporter to the locker device.

8. The distribution system according to claim 1, characterized by further comprising:
a second distribution mechanism that is a mechanism different than the first distribution mechanism and that transports or stores the article, wherein
the manager further manages a second time that is a time earlier than a hand over time at which the second distribution mechanism hands over the article to the first distribution mechanism and is a last time at which a human contacted the article that is transported or stored by the second distribution mechanism, or manages a second amount of elapsed time that is an amount of elapsed time from the second time.

9. The distribution system according to claim 8, characterized in that when a human is not involved in the hand over of the article from the second distribution mechanism to the first distribution mechanism, the manager manages the second time as the first time, or manages the second amount of elapsed time as the first amount of elapsed time.

10. The distribution system according to claim 9, characterized by further comprising:
a determiner that determines, based on the second time or the second amount of elapsed time, a hand over timing of the article from the second distribution mechanism to the transporter of the first distribution mechanism such that a target amount of elapsed time elapses from the second time at which a human last contacted the article to the receiving time at which the article is received.

11. The distribution system according to claim 10, characterized by further comprising:
an estimator that estimates, based on the destination, an amount of transport time needed for the transporter of the first distribution mechanism to transport the article to the destination, wherein
the determiner
calculates a second target amount of elapsed time that is the estimated amount of transport time shorter than a first target amount of elapsed time that is the target amount of elapsed time, and
determines, as the hand over timing, a timing at or later than a time that is the second target amount of elapsed time later than the second time, or a time at which the second amount of elapsed time is the second target amount of elapsed time.

12. The distribution system according to claim 10, characterized in that the determiner determines the hand over timing based further on at least one of a type of the article, a type of a packaging member in which the article is packaged, or an environment of the article from the second time at which a human last contacted the article to when the article is handed over to the transporter.

13. The distribution system according to claim 6, characterized in that the target amount of elapsed time is an amount of time from when a predetermined virus or a predetermined bacterium is discharged from a body of a human to when a magnitude of infectivity of the virus or the bacterium is less than or equal to a predetermined magnitude, and
the notifier performs the notification informing of a recommended receiving start time at which receiving of the article is recommended to start, the recommended receiving start time being a time the target amount of elapsed time later than the first time or a time later than the time.

14. The distribution system according to claim 6, characterized in that
the target amount of elapsed time is an amount of time from when a predetermined virus or a predetermined bacterium is discharged from a body of a human to when a magnitude of infectivity of the virus or the bacterium is less than or equal to a predetermined magnitude, and
the distribution system further includes a controller that performs control for causing the transporter of the first distribution mechanism to complete transportation of the article to the destination at a time that is the target amount of elapsed time after the first time, or later, or at a time at which the first amount of elapsed time is the target amount of elapsed time, or later.

15. The distribution system according to claim 6, characterized in that
the target amount of elapsed time is an amount of time from when a predetermined virus or a predetermined bacterium is discharged from a body of a human to when a magnitude of infectivity of the virus or the bacterium is less than or equal to a predetermined magnitude, and
the distribution system further includes the controller that performs control for causing the transporter of the first distribution mechanism to transport the article to a locker device installed at the destination and, then control for unlocking the locked locker device storing the transported article at a time that is the target amount of elapsed time after the first time, or later, or at a time at which the first amount of elapsed time is the target amount of elapsed time, or later.

16. The distribution system according to claim 1, characterized by further comprising:
an acquirer that acquires procedure identification information identifying a procedure that is a procedure related to a delivery of the article and that is performed on the article, wherein
when, in a storage in which the procedure identification information identifying the procedure and information expressing whether or not a human is involved in the procedure are associated and stored in plurality, the information associated with the acquired procedure identification information expresses that a human is involved, the manager manages, as the first time, an acquisition time at which the procedure identification information is acquired, or manages, as the first amount of elapsed time, an amount of elapsed time from the acquisition time.

17. An information processing device characterized by comprising:
a controller that performs control for causing a first distribution mechanism including a transporter to transport an article to a destination of the article; and a manager that manages a first time that is a time earlier than a receiving time at which the article transported by the transporter is received and that is a last time at which a human contacted the article, or manages a first amount of elapsed time that is an amount of elapsed time from the first time.

18. A method characterized by comprising:

managing, by a distribution system including a first distribution mechanism that includes a transporter that transports an article to a destination of the article, a first time that is a time earlier than a receiving time at which the article transported by the transporter is received and that is a last time at which a human contacted the article, or managing a first amount of elapsed time that is an amount of elapsed time from the first time.

* * * * *